(12) United States Patent
Coetzee et al.

(10) Patent No.: US 8,791,105 B2
(45) Date of Patent: Jul. 29, 2014

(54) METHODS FOR ALLEVIATING CHRONIC PAIN AND IMPROVING PERFORMANCE OF CATTLE UNDERGOING DEHORNING OR CASTRATION

(75) Inventors: Johann F. Coetzee, Cambridge, IA (US); Stanley P. Kukanich, Manhattan, KS (US)

(73) Assignee: Kansas State University Research Foundation, Manhatten, KS (US)

( * ) Notice: Subject to any disclaimer, the term of this patent is extended or adjusted under 35 U.S.C. 154(b) by 0 days.

(21) Appl. No.: 13/810,117

(22) PCT Filed: Jul. 14, 2011

(86) PCT No.: PCT/US2011/044017
§ 371 (c)(1),
(2), (4) Date: Jan. 14, 2013

(87) PCT Pub. No.: WO2012/009542
PCT Pub. Date: Jan. 19, 2012

(65) Prior Publication Data
US 2013/0123245 A1  May 16, 2013

Related U.S. Application Data

(60) Provisional application No. 61/364,314, filed on Jul. 14, 2010.

(51) Int. Cl.
| | | |
|---|---|---|
| *A61K 31/54* | (2006.01) | |
| *A61K 31/19* | (2006.01) | |
| *A23K 1/165* | (2006.01) | |
| *A23K 1/18* | (2006.01) | |
| *A01K 17/00* | (2006.01) | |
| *A23K 1/16* | (2006.01) | |
| *A61K 31/5415* | (2006.01) | |
| *A61K 31/197* | (2006.01) | |

(52) U.S. Cl.
CPC ............. *A61K 31/5415* (2013.01); *A23K 1/165* (2013.01); *A61K 31/19* (2013.01); *A23K 1/1813* (2013.01); *A23K 1/1893* (2013.01); *A01K 17/00* (2013.01); *A23K 1/1646* (2013.01); *A61K 31/197* (2013.01)
USPC ....................... 514/226.5; 514/567

(58) Field of Classification Search
CPC ....... A61K 31/54; A61K 31/19; A61K 31/20; A61K 8/365; A61K 31/195; A61K 31/44; C07D 417/12; C07D 279/02; C07D 513/04; A61Q 19/00
USPC ............................................. 514/226.5, 557
See application file for complete search history.

(56) References Cited

U.S. PATENT DOCUMENTS

| | | |
|---|---|---|
| 6,869,948 B1 | 3/2005 | Bock et al. |
| 2005/0187213 A1 | 8/2005 | Lang et al. |
| 2005/0245510 A1 | 11/2005 | Friton et al. |
| 2005/0288280 A1 * | 12/2005 | Friton et al. ............... 514/226.5 |
| 2006/0122105 A1 | 6/2006 | Strom et al. |
| 2006/0154863 A1 | 7/2006 | Skubatch |
| 2007/0009502 A1 | 1/2007 | Lall et al. |
| 2007/0149465 A1 | 6/2007 | Kenley et al. |
| 2007/0232647 A1 * | 10/2007 | Goetze et al. ................. 514/310 |
| 2008/0096916 A1 | 4/2008 | Kehrli |
| 2009/0148502 A1 | 6/2009 | Pronovost |

FOREIGN PATENT DOCUMENTS

| | | |
|---|---|---|
| CA | 2261319 | 11/2000 |
| WO | 02096216 A1 | 12/2002 |

OTHER PUBLICATIONS

Coetzee et al (Veterinary Therapeutic vol. 10(4) 2009).*
Sprecher et al. (Theriogenology 47:1179-1187 (1997).*
Stewart et al. J. Dairy Sci. 92 :1512-1519.*
International Search Report and Written Opinion for PCT/US2011/044017, dated Dec. 6, 2011, 18 pages.
Written Opinion of the International Preliminary Examining Authority, dated Jul. 18, 2012 for PCT/US2011/044017, 8 pages.
International Preliminary Report on Patentability for PCT/US2011/044017, dated Nov. 5, 2012, 20 pages.
FDA. Clinical 6, "Guidance for Industry. Providing Clinical Evidence of Effectiveness for Human Drug and Biological Products," Center for Drug Evaluation and Research, Center for Biologics Evaluation and Research, May 1998.
Heinrich, A., The impact of meloxicam on postsurgical stress associated with cautery dehorning, America Dairy Science Association, J. Dairy Sci. 92, 2009, pp. 540-547.
Friton, G.M., Long-term effects of meloxicam in the treatment of respiratory disease in fattening cattle, The Veterinary Record, 2005, 156:809-811.
Fulwider, W.K., Survey of dairy management practices on one hundred thirteen North Central and northeastern United States Dairies, 2008, pp. 1686-1692, J. Dairy Sci. 91(4).
Hoe, F.G.H, Opinions and practices of Wisconsin dairy producers about biosecurity and animal well-being, 2006, pp. 2297-2308, J. Dairy Sci. 89.
Faulkner, P.M., Reducing pain after dehorning in dairy calves, D.M. 2000, pp. 2037-2041, J. Dairy Sci. 83.
USDA. (2009). Dairy 2007, Part IV: Reference of dairy cattle health and Management practices in the United States, 2007. USDA:APHIS:VS, CEAH. Fort Collins, CO #N494.0209. Available at http://www.aphis.usda.gov/vs/ceah/ncahs/nahms/dairy/dairy07/Dairy2007 artJV.pdf. Accessed Nov. 12, 2009.
Jim, G.K. "A Field Investigation of the Economic Impact of Respiratory Disease in Feedlot Calves," Can Vet J. vol. 34, Nov. 1993.

* cited by examiner

*Primary Examiner* — Shirley V Gembeh
(74) *Attorney, Agent, or Firm* — Hovey Williams LLP

(57) ABSTRACT

Methods of improving performance, increasing weight gain, and decreasing incidence of disease in ruminant and pre-ruminant animals, such as cattle, after undergoing painful processing procedures, such as castration and dehorning, are provided. Veterinary formulations for use in methods of the invention are also provided. The formulations comprise a compound selected from the group consisting of meloxicam, gabapentin, the pharmaceutically acceptable salts thereof, and combinations thereof. Methods of treating pathological pain in cattle are also provided.

24 Claims, 13 Drawing Sheets

METHODS FOR ALLEVIATING CHRONIC PAIN AND IMPROVING PERFORMANCE OF CATTLE UNDERGOING DEHORNING OR CASTRATION

CROSS-REFERENCE TO RELATED APPLICATIONS

The present application is the National Stage of International Application No. PCT/US2011/044017, filed Jul. 14, 2011, which claims the priority benefit of U.S. Provisional Patent Application Ser. No. 61/364,314, filed Jul. 14, 2010, entitled MELOXICAM TREATMENT OF CATTLE UNDERGOING DEHORNING OR CASTRATION, incorporated by reference in its entirety herein.

FEDERALLY SPONSORED RESEARCH OR DEVELOPMENT

This invention was made with government support under NRI Grant #2008-35204-19238 awarded by the United States Department of Agriculture. The United States government has certain rights in the invention.

BACKGROUND OF THE INVENTION

1. Field of the Invention

The present invention relates to methods and veterinary formulations for alleviating and treating chronic pain and improving the performance of ruminant and pre-ruminant animals following painful processing procedures, such as dehorning and castration.

2. Description of Related Art

Cattle processing includes vaccination, castration, dehorning, branding, and identification tagging or implanting prior to, or upon arrival of the cattle at a feedlot or farm. Some of these procedures are viewed as being painful or stressful for the animal. Societal concern about the moral and ethical treatment of animals, including livestock, is becoming more prevalent. Castration is a common procedure in the U.S. beef industry performed on at least 8 million calves per year in the United States alone. However, in addition to acute pain from the procedure castration soon after receipt of long-hauled, highly-stressed bull calves is associated with increased morbidity and mortality and decreased weight gain as compared to steers. Dehorning is another standard cattle management procedure involving the removal of the horns or horn buds of cattle (usually young calves) to prevent injury to other members of the herd, as well as handlers. Negative public perception of pain associated with livestock management procedures such as these has increased, highlighting the need to develop practices to alleviate pain associated with dehorning and castration procedures. Several organizations, including the American Veterinary Medical Association, have stated that pain and physiologic stress of the animals should be minimized (AVMA, 2007). Pain and distress is commonly associated with behavioral, physiological and neuroendocrine changes such as increases in plasma cortisol concentrations. Although it has been reported that non-steroidal anti-inflammatory drug (NSAID) administration attenuates plasma cortisol response, there are currently no drugs specifically approved for pain relief in livestock in the United States (Coetzee et al., 2007; FDA, 2006).

Pain is defined as an aversive sensory or emotional experience representing awareness by the animal of actual or potential tissue damage. Pain is associated with physiological, behavioral and neuroendocrine changes aimed at reducing or avoiding tissue damage, limiting pain reoccurrence and promoting recovery. Pain perception (e.g., nociception) involves the transduction of chemical signals at the site of injury into electrical energy. This is followed by transmission of the electrical signal via nerve fibers up the spinothalamic tracts to the brain where pain perception occurs. The initial response to a noxious stimulus is typically brief, well-localized and somewhat proportional to the intensity of the insult. The second phase of the response is prolonged, diffuse and often associated with hypersensitivity around the point where the initial stimulus was applied. This effect may lead to persistent post-injury changes in the central nervous system resulting in pain hypersensitivity or central sensitization ("wind-up").

Surgery-induced pain and central sensitization consist of two phases: an immediate incisional phase and a prolonged inflammatory phase that arises primarily due to tissue damage. Several methods have been developed to directly or indirectly assess pain associated with dehorning and castration in calves. Measurements of physiological changes include assessment of heart rate (Heinrich et al., 2009) and heart rate variability (Stewart et al., 2009) and changes in peripheral vascular perfusion determined by thermography (Stewart et al., 2009). Physiological effects of dehorning have also been evaluated by assessing changes in body weight and performance (Faulkner and Weary, 2000). Neuroendocrine effects have been studied using circulating biomarkers such as cortisol (Stafford and Mellor, 2005) and substance P (Coetzee et al., 2008). Behavioral responses to painful events have been assessed using constant video surveillance, chute exit speed determination (Burrows and Dillon, 1997), step counts and stride length (Currah et al, 2009). Remote accelerometer sensors have also been used to objectively monitor cattle behavior, and this system has been validated with high accuracy, compared to video observation, in predicting cattle activity (Robert et al, 2009). Accelerometers have even been used to illustrate behavioral changes in cattle after castration (White et al., 2008), but this technology has not been evaluated in calves after dehorning or in calves given pre-emptive analgesia.

Studies demonstrating the adequacy of preemptive analgesia must meet two basic requirements (Kissin, 2000). The first is to verify the effectiveness of a treatment by demonstrating a direct pharmacological effect. This can be accomplished by comparing differences in acute biomarkers of pain and distress, such as cortisol response and heart rate, between treated and control subjects. It is noteworthy that plasma concentrations of NSAIDs and their actions at the molecular level are not in phase (Lees et al, 2004). This may lead to hysteresis in the relationship between drug concentration and effect and may explain why drug effects do not correspond with peak drug concentration. The second requirement is to demonstrate extension of the anti-nociceptive effect into the postoperative period when pain due to inflammation becomes the dominant process (Kissin, 2000). In practical terms, two approaches have been used to demonstrate the efficacy of preemptive analgesic regimens. The first is to demonstrate a reduction in pain intensity beyond the presence of the drug in the biophase in treated and untreated control subjects. The second approach is to demonstrate that a treatment applied before surgery is more effective than the treatment applied at the end of surgery (Kissin, 2000).

Several compounds including opioids (eg. butorphanol), local anesthetics (eg. lidocaine), α2-adrenergic receptor agonists (eg. xylazine) and NMDA receptor antagonists (eg. ketamine) exert direct analgesic effects by targeting specific receptors in the central and peripheral nervous system. In contrast, NSAIDs produce analgesia and reduce inflammation by inhibiting the enzyme cyclooxygenase (COX) and subsequent prostaglandin production in the peripheral tissues and central nervous system. However, NSAIDs are generally not recognized as having a preventative effect.

Meloxicam (4-hydroxy-2-methyl-N-(5-methyl-2-thiazolyl)-2H-1,2-benzothiazine-3-carboxamide-1,1-dioxide) is an NSAID of the oxicam class that is approved in the European Union for adjunctive treatment of acute respiratory disease; diarrhea and acute mastitis when administered at 0.5 mg/kg intravenously (IV) or subcutaneously (SC) (EMEA, 2009) to sick animals. Meloxicam is believed to bind preferentially to cyclooxygenase-2 (COX-2), thereby inhibiting prostaglandin synthesis, although definitive evidence of COX-selectivity in calves is deficient in the published literature (Lees, 2009).

With respect to painful processing events, it was recently reported in a survey of North-central and Northeastern United States dairy producers that only 12.4% of dairy owners use local anesthetic nerve blocks and only 1.8% provide systemic analgesia at the time of dehorning (Fulwider et al., 2008). Similarly, only 18% of Wisconsin dairy producers report using local anesthetics prior to dehorning (Hoe et al., 2006). These data are consistent with the results of the recent National Animal Health Monitoring System (NAHMS) survey that reported that only 17.7% of U.S. operations report using analgesics or anesthetics during the dehorning procedure (NAHMS, 2009). In addition, such drugs must be administered almost exclusively intravenously, further decreasing their likelihood of use. That is, due to the unique nature of ruminant digestion, few drugs are available for oral administration. More specifically, for use in cattle and other ruminants, orally administered drugs must be able to withstand the fermentation and alkaline pH of the rumen, but also survive in the highly acidic environment of the fourth stomach. Many drugs are ionized during ruminant digestion decreasing their bioavailability below effective levels. Few studies have been done on the bioavailability of orally administered analgesics in cattle.

The effects of meloxicam administration without local anesthesia on post-surgical behavior and performance in older calves (>16 weeks of age) have also not been described. In addition, the compartmental pharmacokinetics of meloxicam administered intravenously to calves has not been reported. The oral pharmacokinetics of meloxicam have also not been described. If meloxicam administration alone mitigates pain and distress and produces quantifiable performance benefits when administered prior to a painful cattle management procedure, such as dehorning or castration, this would provide producers and veterinarians with a much-needed practical and cost-effective way to reduce pain and distress after dehorning and/or castration. Meloxicam may also have other benefits for the animal's health following painful processing procedures.

For example, bovine respiratory disease (BRD) is the most common and costly disease of feedlot cattle in the United States (Smith, 1998; NAHMS, 2000a). In 1999, most feedlots (97.4%) within 12 states reported an overall BRD incidence of 14.4% (NAHMS, 2000a). Treatment costs for BRD averaged $15.57 per sick animal. Costs are significantly greater when labor, isolation, increased time on feed, mortality, prophylaxis, and meta-phylaxis treatments are considered (NAHMS, 2000a). Current BRD prevention strategies include mass medication of cattle at higher risk of developing BRD with antimicrobials and the use of vaccination. Neither strategy has been very effective at preventing the incidence of BRD cases especially in high risk groups of cattle, such as bulls castrated upon arrival at feedlots. Furthermore, the mass medication of cattle with antimicrobials is under increasing scrutiny due to the risk of development of antimicrobial resistance. The use of an NSAID to mitigate the negative effects of castration may therefore, provide producers with an effective alternative to antimicrobial use. In addition, if such NSAIDs could be administered orally, this would simplify the administration process, making it more likely that producers will use them when processing their cattle.

Pathological (i.e., chronic) pain states which occur in cattle as a result of tissue damage, nerve damage, and inflammation are also frequently associated with pain hypersensitivity. Pain hypersensitivity manifests as hyperalgesia (exaggerated responses to painful stimuli) and allodynia (pain resulting from normally innocuous stimuli). Hyperalgesia has been reported to persist in dairy cattle and lame sheep for at least 28 days after the initial causal lesion has resolved (Ley et al. 1996; Whay et al., 1998). Consequently, chronic pain associated with lameness is considered one of the most significant welfare concerns in dairy cows. Inflammatory pain associated with lameness responds modestly to treatment with NSAIDs, but neuropathic pain is considered to be refractory to the effects of NSAIDs and many opioid analgesics. Therefore, there is a need to identify drugs and drug targets for alleviating chronic pain of neuropathic origin in animals. Gabapentin (1-(aminomethyl) cyclohexane acetic acid) is a drug originally developed for the treatment of spastic disorders and epilepsy in humans (Cheng and Chiou, 2006). The effectiveness of oral gabapentin alone or co-administered with meloxicam for alleviating pain in ruminants has not been reported.

SUMMARY OF THE INVENTION

The present invention is broadly concerned with methods of improving performance, health, and well-being in ruminant or pre-ruminant animals (e.g., cattle, sheep, goats, llamas, etc.) undergoing painful processing procedures or suffering from pathological pain. In one aspect, the invention provides a method of improving the performance of a ruminant or pre-ruminant animal following processing. The method comprises administering to the animal an effective amount of meloxicam or a pharmaceutically acceptable salt thereof, and subjecting the animal to processing without the use of a local anesthetic. Advantageously, the animal has improved performance (such as weight gain and overall health and well-being) after processing.

In another aspect, a further method of improving the performance of a ruminant or pre-ruminant animal following processing is provided. The method comprises orally administering to the animal an effective amount of meloxicam or a pharmaceutically acceptable salt thereof, and subjecting the animal to processing. Advantageously, the animal has improved performance after processing.

The invention also provides a method of increasing weight gain in a ruminant or pre-ruminant animal having horns or horn buds following dehorning. The method comprises administering to the animal an effective amount of meloxicam or a pharmaceutically acceptable salt thereof, and dehorning the animal. Advantageously, the animal has increased weight gain after dehorning, as compared to an animal not receiving meloxicam or a pharmaceutically acceptable salt thereof prior to dehorning.

A method of preventing respiratory illness in a ruminant or pre-ruminant male animal following castration is also provided. The method comprises administering to a ruminant or pre-ruminant animal an effective amount of meloxicam or a pharmaceutically acceptable salt thereof, and castrating the animal, wherein the animal remains free of respiratory illness.

The invention also provides a veterinary formulation for increasing weight gain in a ruminant or pre-ruminant animal following dehorning. The formulation comprises meloxicam or a pharmaceutically acceptable salt thereof.

A veterinary formulation for preventing respiratory illness in a ruminant or pre-ruminant male animal following castration is also provided. The formulation comprises meloxicam or a pharmaceutically acceptable salt thereof.

In a further aspect, the invention is concerned with a method of treating pathological/chronic pain in a ruminant or pre-ruminant animal. The method comprises administering, preferably orally, an effective amount of meloxicam and/or gabapentin or the pharmaceutically acceptable salts thereof (e.g., a compound selected from the group consisting of meloxicam or the pharmaceutically acceptable salts thereof, gabapentin or the pharmaceutically acceptable salts thereof, and combinations thereof) to a ruminant or pre-ruminant animal having pathological pain. A veterinary formulation for treating pathological pain in a ruminant or pre-ruminant animal suffering from lameness is also provided. The formulation comprises an effective amount of a compound selected from the group consisting of meloxicam or the pharmaceutically acceptable salts thereof, gabapentin or the pharmaceutically acceptable salts thereof, and combinations thereof.

BRIEF DESCRIPTION OF THE DRAWINGS

Figure (FIG. 1 is a graph of the mean (±SD) plasma meloxicam concentrations following single IV administration at 0.5 mg/kg body weight or single oral administration at 1 mg/kg body weight from Example 1.

DETAILED DESCRIPTION

Figure 1:
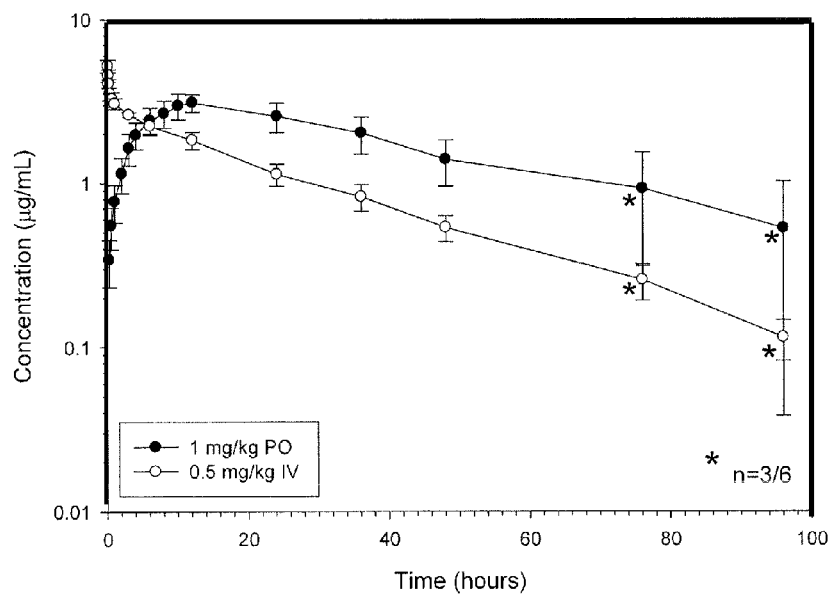

In more detail, the present invention is concerned with methods of mitigating behavioral and performance effects, as well as reducing the incidence of disease in ruminant and pre-ruminant animals undergoing processing procedures that would cause pain. Such processing procedures include those typically carried out as part of livestock management such as those selected from the group consisting of dehorning, castration, branding, and docking (tail or ears). More specifically, the invention relates to the use of meloxicam or a pharmaceutically acceptable salt thereof, to improve the performance of a ruminant or pre-ruminant animal following such painful processing procedures. Advantageously, the present invention is effective for improving performance without the use of a local anesthetic (e.g., cornual nerve block, lidocaine, procaine, or systemic sedative analgesia) or other adjunctive therapy (e.g., antibiotic, hormonal implant, ionophore, other growth promotants, or vaccine). In preferred embodiments, the invention relates to cattle and specifically improving the performance of ruminant and pre-ruminant bovines. The term "pre-ruminant" refers to young animals before development of a functional ruminant stomach compartment. The term "bovine" is used herein to refer generally to all types of domesticated cattle (bovines), including heifers (young females), bulls (uncastrated males), steers (castrated males), calves (young cattle of both sexes), and cows (adult females), unless otherwise specified. The phrase "improving performance," as used herein encompasses any suitable marker of performance and well-being of the animal, including weight gain, incidence of disease, time spent lying down, and time spent standing or walking, etc., with weight gain and incidence of disease being the preferred markers of performance.

In the invention, an effective amount of meloxicam or a pharmaceutically acceptable salt thereof is administered to a ruminant or pre-ruminant animal prior to subjecting the animal to the painful processing event. As used herein, an "effective amount" refers to an amount capable of providing bioavailable levels of the active compound (i.e., meloxicam) sufficient to achieve the desired performance improvement. In a preferred embodiment, the meloxicam or pharmaceutically acceptable salt thereof will be administered to the animal in an amount sufficient to provide meloxicam levels (independent of salt, if any) of from about 0.1 mg to about 5 mg of meloxicam per kg of body weight of the animal, preferably from about 0.25 mg/kg to about 2 mg/kg of body weight of the animal, and more preferably from about 0.5 mg/kg to about 1 mg/kg of body weight of the animal. Thus, it will be appreciated that in the case of meloxicam salts, for example, the formulation may be administered in amounts greater than the above ranges to provide sufficient levels of the active meloxicam (e.g., 4.1 mg/kg meloxicam tartrate is equivalent to 2.8 mg/kg meloxicam base).

The meloxicam or pharmaceutically acceptable salt thereof is preferably in a form suitable for oral or parenteral administration, including without limitation, tablets, granules, capsules, liquids, top-dress preparations, suspensions, bolus, drenches, solutions, topical pour-ons, pre-mixes, or sustained-release implants. Rectal suppositories may also be used.

The meloxicam or pharmaceutically acceptable salt thereof can be administered directly or as part of a veterinary formulation comprising meloxicam or a pharmaceutically acceptable salt thereof and a carrier. The term "carrier," as used herein, means one or more compatible base compositions with which the active ingredient (e.g., meloxicam) is combined to facilitate the administration of ingredient, and which is suitable for administration to an animal. Such preparations may also routinely contain salts, buffering agents, preservatives, and optionally other therapeutic ingredients. The carrier would naturally be selected to minimize any degradation of the active ingredient and to minimize any adverse side effects in the subject, as would be well known to one of ordinary skill in the art. For example, the veterinary formulation can be a liquid system for oral or parenteral administration comprising meloxicam or a pharmaceutically acceptable salt thereof dispersed or dissolved in a carrier. Exemplary carriers for this embodiment, depending upon the method of administration, would include water, oil, water-in-oil or oil-in-water emulsion, milk, milk replacer, propylene glycol, polyethylene glycol, n-methyl-2-pyrrolidone, feed top-dress, pre-mix, or bolus. The veterinary formulation can also be a solid system for oral administration comprising meloxi cam or a pharmaceutically acceptable salt thereof dispersed in a carrier. Exemplary carriers in this embodiment can include binders (e.g. gelatin, cellulose, talc, hydroxyethylcellulose, carboxyethylcellulose, silicon dioxide, hypromellose, magnesium stearate, polydextrose, titanium dioxide), sweeteners (e.g., glucose, sucrose), and/or flavoring agents. It will also be appreciated that a solid veterinary formulation containing meloxicam or a pharmaceutically acceptable salt thereof can be first dissolved in a liquid medium to create a solution or suspension, which is then administered to the animal.

A pharmaceutically acceptable "salt" of the invention includes acid addition salts, such as the meglumine, sodium, potassium, tartrate, or ammonium salts of meloxicam. Meloxicam and suitable salts are disclosed in U.S. Pat. No. 4,233,299, incorporated by reference herein to the extent not inconsistent with the present invention. The term "pharmaceutically acceptable," as used herein, is meant to include compounds that are not biologically or otherwise undesirable, i.e., the compound may be administered without causing any undesirable biological effects or interacting in a deleterious manner or interfering with any of the other components of the composition in which it is contained.

In the method, meloxicam or a pharmaceutically acceptable salt thereof is administered to an animal via a route of administration selected from the group consisting of oral and parenteral.

That is, according to the present invention, the meloxicam or pharmaceutically acceptable salt thereof is administered systemically as opposed to being injected directly into a site of infection or pain. Parenteral administration in the present invention includes subcutaneous, intramuscular, transdermal, or intravenous injection/administration. Oral administration can include separate administration of the formulation (e.g., hand feeding of tablets, etc., or administration of suspension via gavage tube) or inclusion of the meloxicam or pharmaceutically acceptable salt thereof in the feed, water, or milk/milk replacer to be fed to the animal. According to the present invention, the meloxicam or pharmaceutically acceptable salt thereof advantageously does not need to be used in a daily dosing regimen to be effective. Rather, the meloxicam or pharmaceutically acceptable salt thereof is preferably administered as a single dose prior to the painful processing event. More specifically, meloxicam or a pharmaceutically acceptable salt thereof is generally administered to the animal any time up to about 72 hours before processing, preferably from about 0 to about 48 hours before processing, more preferably from about 0.5 to about 24 hours before processing, and most preferably from about 8 to about 12 hours before processing. In some embodiments, where the animal has been administered meloxicam or a pharmaceutically acceptable salt thereof prior to processing, meloxicam or a pharmaceutically acceptable salt thereof is preferably not administered to the animal after processing. That is, the initial dose is preferably not followed up with a subsequent (or daily) administration of meloxicam or a pharmaceutically acceptable salt thereof. In another embodiment, meloxicam or a pharmaceutically acceptable salt thereof can be administered as a single dose or multiple doses at any time up to and including the time of processing (from about 0 to about 1 hour before processing) or any time after processing (preferably within about 8 hours).

According to a preferred aspect, the invention is effective for increasing weight gain of a ruminant or pre-ruminant animal (such as a bovine) following dehorning. In one method of the invention, an effective amount of meloxicam or a pharmaceutically acceptable salt thereof is administered to the animal. The animal is then subjected to dehorning. Depending on the age of the animal, dehorning can be accomplished by hot iron, knife, or the use of spoon, scoop, cup, or tube dehorning tools, or any other acceptable method suitable for removing or destroying the horn bud and horn-producing cells of the horn bud. Preferably, meloxicam or pharmaceutically acceptable salt thereof is administered to the animal any time up to about 72 hours before dehorning, preferably from about 0 to about 48 hours before dehorning, more preferably from about 0.5 to about 24 hours before dehorning, and most preferably from about 8 to about 12 hours before dehorning. In another embodiment, meloxicam or a pharmaceutically acceptable salt thereof can be administered as a single dose or multiple doses at any time up to and including the time of dehorning (from about 0 to about 1 hour before dehorning) or any time after dehorning (preferably within about 8 hours). After dehorning, the wound may be heat cauterized to minimize bleeding. Advantageously, the average daily weight gain of the animal will be at least about 0.75 kg/day, more preferably at least about 0.9 kg/day, and even more preferably at least about 1 kg/day, as calculated over a 10-day period post-dehorning. This aspect of the invention is preferably carried out on young calves (<8 weeks) before the horn becomes attached to the frontal bone of the skull; however, it is also effective in older calves or adult cattle whose horns have attached to the skull.

In another preferred aspect, the invention is effective for preventing respiratory illness in a ruminant or pre-ruminant male animal (such as a bull calf) following physical/surgical castration. An effective amount of meloxicam or a pharmaceutically acceptable salt thereof is administered to the animal. The animal is then subjected to castration. Castration can be carried out using any acceptable method, including surgical removal of the testicles Icing a scalpel or Newberry knife. Preferably, meloxicam or pharmaceutically acceptable salt thereof is administered to the animal at any time up to about 72 hours before castration, preferably from about 0 to about 48 hours before castration, more preferably from about 0.5 to about 24 hours before castration, and most preferably from about 8 to about 12 hours before castration. In another embodiment, meloxicam or a pharmaceutically acceptable salt thereof can be administered as a single dose or multiple doses at any time up to and including the time of castration (from about 0 to about 1 hour before castration) or any time after castration (preferably within about 8 hours). Regardless of the embodiment, the animals advantageously remain free of respiratory illness for at least about 28 days post-castration, more preferably at least about 21 days post-castration, and even more preferably at least about 14 days post-castration. Importantly, this aspect of the invention is concerned specifically with prevention of respiratory illness, such as Bovine Respiratory Disease in cattle, and not treatment of animals that already have a respiratory illness. Thus, the meloxicam or pharmaceutically acceptable salt thereof is administered to an otherwise healthy animal (i.e., an animal that does not have a respiratory illness), and is not administered to an animal that is already suffering from a respiratory illness. Likewise, the meloxicam or pharmaceutically acceptable salt thereof in this embodiment is not used to treat any other acute infection (such as mastitis) or as part of an adjunctive therapy, but only for prevention of illness.

According to a further aspect, the invention provides an effective method of treating pathological or chronic pain in ruminant and pre-ruminant animals, comprising administering an effective amount of meloxicam or a pharmaceutically acceptable salt thereof to an animal suffering from pathological pain. Alternatively, the invention provides an effective method of treating pathological pain in ruminant and pre-ruminant animals, comprising administering an effective amount of gabapentin or a pharmaceutically acceptable salt thereof to an animal suffering from pathological pain. The invention also provides a further method of treating pathological pain in ruminant and pre-ruminant animals comprising co-administering an effective amount of meloxicam and gabapentin or the pharmaceutically acceptable salts thereof to an animal suffering from pathological pain. The phrase "co-administration" is intended to embrace administration of each agent in a sequential manner as well as co-administration of these agents in a substantially simultaneous manner, such as in a single veterinary formulation or in doses given separately, but nonetheless administered substantially simultaneously. When used (alone or in combination with meloxicam), the gabapentin or pharmaceutically acceptable salt thereof will be administered to the animal in an amount sufficient to provide gabapentin levels (independent of salt, if any) of from about 2 mg to about 50 mg of gabapentin per kg of body weight of the animal, preferably from about 10 mg/kg to about 30 mg/kg of body weight of the animal, and more preferably from about 15 mg/kg to about 20 mg/kg of body weight of the animal. Animals treated with the inventive methods have decreased clinical lameness scores as scored according to the Sprecher lameness scoring system described herein. These animals also have increased ground contact force on the lame leg, increased stride length, and increased number of steps (activity) taken over a 96-hour period after treatment. Administration of meloxicam and/or gabapentin according to the invention can be repeated on a daily basis until the animal recovers from the pathological pain. Preferably, meloxicam and/or gabapentin is provided as a single or multiple doses once daily from about 1 to about 28 days, preferably from about 1 to about 14 days, and more preferably from about 1 to about 7 days.

EXAMPLES

The following examples set forth methods in accordance with the invention. It is to be understood, however, that these examples are provided by way of illustration and nothing therein should be taken as a limitation upon the overall scope of the invention.

Example 1

Pharmacokinetics of Intravenous and Oral Meloxicam in Ruminant Calves

1. Introduction

The purpose of this study was to investigate the pharmacokinetics and oral bioavailability of meloxicam in ruminant calves. Six Holstein calves (145 to 170 kg) received meloxicam at 0.5 mg/kg IV or 1 mg/kg PO in a randomized crossover design with a 10-day washout period. Plasma samples collected up to 96 hours after administration were analyzed by liquid chromatography/mass spectrometry followed by non-compaitmental pharmacokinetic analysis. A mean peak plasma concentration of 3.10 µg/mL (range, 2.64 to 3.79

μg/mL) was recorded at 11.64 hours (range, 10 to 12 hours) with a half-life of 27.54 hours (range, 19.97 to 43.29 hours) after oral meloxicam administration. The bioavailability of oral meloxicam corrected for dose was 1.00 (range, 0.64 to 1.66). These findings indicate that oral meloxicam administration might be an effective and convenient means of providing long-lasting analgesia to ruminant calves.

2. Materials and Methods a. Experimental Cattle

Six male Holstein calves approximately 3 months of age were obtained from a commercial diary in southwest Kansas. Mean (±standard deviation (SD)) weights at first and second treatment administrations were 159.1±5.26 kg and 172.3±9.63 kg, respectively. Weights for dose calculation were determining by weighing the calves 24 hours before treatment administration. Study animals were acclimated in group housing comprising six calves/pen for about 3 weeks before study commencement. Housing consisted of an outdoor concrete pad (9.75×18.29 m) with straw bedding and a partial roof. Cattle were fed on a typical receiving diet composed of cracked corn, oats, soybean meal, molasses, and a protein-vitamin-mineral supplement at 8 kg/head/day throughout the experiment. Prairie hay and water were offered ad libitum. Feed was not withheld before study commencement.

All experimental procedures in this study were approved by the Kansas State University Institutional Animal Care and Use Committee (IACUC) under the supervision of the University Veterinarian (Protocol #2694).

b. Experimental Design

A crossover study design was used, with calves randomly assigned to one of two dosing regimens. The observed washout period between treatment and administration was 10 days. Approximately 12 hours before each phase of the study began, the calves were restrained for IV catheter placement. After restraint, the area over the jugular vein was clipped and disinfected with 70% isopropyl alcohol and povidone-iodine scrub swabs. The catheter site was infiltrated with 2% lidocaine injection (Hospira; 1 mL SC) before placement of a 14-gauge, 130 mm extended-use catheter (Milacath, MILA International, Florence, Ky.), which was sutured to the skin with #3 nylon suture. Calves assigned to the IV meloxicam group were fitted with two catheters, one designated for drug administration and the other for blood sample collection. Catheter patency was maintained with a heparin-saline flush containing 3 USP units of heparin sodium/1 mL saline (Heparin Sodium Injection, Baxter Healthcare). Each calf was subjected to one of the following two treatments in each treatment period (n=3 calves/treatment/period).

1) IV injection of 0.5 mg/kg of meloxicam (METACAM® 5 mg/mL Solution for Injection [NADA 141-219]; Boehringer Ingelheim Vetmedica; lot #118ZN15) administered as a bolus in the jugular vein with a designated catheter. The catheter was then flushed with 5 mL of heparin-saline and removed immediately after administration.

2) Oral meloxicam administered at 1 mg/kg (meloxicam, 15-mg tablets [NDC 60505-2554-1]; Apotex Corp., Weston, Fla.; lot # JD9485). Tablets were dissolved in 50 mL of water within 5 minutes of administration by stomach tube. The stomach tube was flushed with 1 L of water before removal.

The IV dose was rounded to the nearest 0.5 mL and administered with a 20 mL syringe. The oral dose was rounded to the nearest whole tablet.

Calves were manually restrained with a rope halter for blood collection. In the calves receiving IV meloxicam, about 10 mL of blood was collected as 0, 3, 6, 10, 20, and 40 minutes, and 1, 3, 6, 12, 24, 36, and 48 hours after dosing. In the calves receiving oral meloxicam, blood samples were collected at 0, 15, and 30 minutes, and at 1, 2, 3, 4, 6, 8, 10, 12, 24, 36, and 48 hours after dosing. Based on the results of the first phase, an additional sample was collected from the calves (n=3/treatment) at 72 and 96 hours after administration in the second treatment period of the study. For each collection, blood was drawn into a collection syringe and immediately transferred to lithium-heparin Vacutainer tubes (BD Diagnostics). Samples were stored on ice. Within 30 minutes of collection, the samples were each centrifuged for 10 minutes at 1,500×g. Plasma was then pipetted into cryovials and frozen at −70° C. until analysis.

c. Plasma Drug Analysis

Plasma concentrations of meloxicam (mass:charge ratio [m/z] 352.09→119.90) were determined with high-pressure liquid chromatography (Shimadzu Prominence, Shimadzu Scientific Instruments, Columbia, Md.) and mass spectrometry (API 2000, Applied Biosystems, Foster City, Calif.). Plasma samples or standards (100 μl) were added to 100 μl of internal standard (piroxicam 0.5 μg/mL in methanol, m/z 332.12→95.10) and 300 μl of methanol with 0.1% formic acid to precipitate the proteins. The samples were vortexed for 5 seconds and centrifuged for 10 minutes at 10,000×g. The supernatant, 200 μl, was transferred to an injection vial with the injection volume set to 10 μl. The mobile phase consisted of A: acetonitrile and B: 0.1% formic acid at a flow rate of 0.4 mL/min. The mobile phase consisted of 85% B from 0 to 0.5 minutes with a linear gradient to 50% B at 2.5 minutes, which was maintained until 3 minutes, followed by a linear gradient to 85% B at 4 minutes, with a total run time of 5 minutes. Separation was achieved with a C8 column (Supelco Discovery C8, 50 mm×2.1 mm×5 μm; Sigma Aldrich, St. Louis, Mo.) maintained at 40° C. The standard curve was linear from 0.01 to 10 μg/mL and was accepted if the correlation coefficient exceeded 0.99 and predicted values were within 15% of the actual values. The accuracy of the assay was 103%±7% of the actual value, and the coefficient of variation was 7%, determined on replicates of 5 each at 0.025, 0.5, and 5 μg/mL.

d. Pharmacokinetics Analysis

Pharmacokinetics analyses were performed with computer software (WinNonlin 5.2, Pharsight Corp., Mountain View, Calif.). The variables calculated included the area under the curve from time 0 to infinity ($AUC_{INF}$) using the linear trapezoidal rule, area under the first moment curve from time 0 to infinity ($AUMC_{INF}$), plasma clearance (Cl), plasma clearance per fraction of the dose absorbed (Cl/F), apparent volume of distribution at steady state (Vss), apparent volume of distribution of the area (Vz), apparent volume of distribution of the area per fraction of the dose absorbed (Vz/F), first-order rate constant ($\lambda_z$), terminal half-life ($T_{1/2}, \lambda_z$), and mean residence time extrapolated to infinity (MRT). The maximum serum concentration (Cmax) and time to maximum serum concentration (Tmax) were determined directly from the data. The concentration at time 0 (C0) was calculated by log-linear regression using the first two time points after IV administration. The mean absorption time (MAT) was calculated by subtracting the intravenous from the oral MRT. The fraction of the dose absorbed (F [i.e., bioavailbility]) for oral meloxicam was determined by dividing the $AUC_{INF}$ per dose after oral administration by the $AUC_{INF}$ per dose after IV administration.

3. Results

No adverse effects were noted after IV or oral meloxicam administration. The mean time-concentration profile for meloxicam in calves after IV administration of 0.5 mg/kg body weight is presented in FIG. 1. The calculated noncompartmental pharmacokinetic parameters for each animal are summarized in Table 1 below. After IV administration, meloxicam demonstrated a relatively small mean Vss of 0.171 L/kg (range, 0.15 to 0.19 L/kg) and a slow Cl from the central compartment of 0.1 mL/min/kg (range, 0.08 to 0.12 mL/min/kg). This resulted in a relatively long mean plasma $T_{1/2}, \lambda_z$ of 20.35 hours (range, 17.84 to 22.76 hours).

The compartmental pharmacokinetic parameters for meloxicam following oral administration at 1 mg/kg body weight are presented in Table 2 below. Based on these data, a mean peak plasma meloxicam concentration of 3.10 μg/mL (range, 2.64 to 3.79 μg/mL) was recorded about 12 hours (range, 10 to 12 hours) after oral administration. The AUC following oral administration was similar to that of IV administration, with a calculated bioavailability of 1.00 (range, 0.64 to 1.66). One calf (#16) eliminated meloxicam more slowly than the other calves in the study after oral administration, which resulted in a higher AUC and therefore an inflated bioavailability estimate. The reason for this outlier is not known.

The studies results indicate that a mean Cmax of 3.10 μg/mL occurred approximately 12 hours after oral administration of meloxicam. The combination of a small volume of distribution and a slow clearance resulted in a mean $T_{1/2} \lambda_z$ of 27.54 hours. Oral meloxicam demonstrated excellent bioavailability when corrected for dose. These finding suggest that oral administration of meloxicam might be an effective and convenient means of providing long-lasting analgesia to ruminant calves.

To better characterize the elimination profile of oral and IV meloxicam in cattle, the sampling times were increased in the second period to include 72 and 96 hours after administration. The plasma profile was similar in both periods for both routes of administration, suggesting the true terminal phase of the plasma profile was identified in both periods. Therefore, despite the large extrapolated AUC in the first period, the estimated pharmacokinetic parameters appear accurate. The pharmacokinetic profile of meloxicam described here suggests that oral preemptive analgesia should be administered 12 hours before surgery so that surgery coincides with peak plasma drug concentrations. Further, oral meloxicam may provide effective analgesic concentrations for several days after surgery, based on the calculated mean plasma half-life of about 28 hours. Given that the plasma half-life of meloxicam is longer than the half-lives previously reported for ketoprofen (0.42 hours), salicylate (0.5 hours), and flunixin (4 to 8 hours), this suggests that meloxicam may provide extended duration of activity compared with other NSAIDs currently available.

Example 2

Meloxicam and Post-Dehorning Activity of Cattle
1. Introduction
This study was conducted to determine the pharmacokinetics of meloxicam and its effect on serum cortisol, heart rate, behavior, and weight gain in calves after scoop dehorning without local anesthesia. The pharmacokinetics and effect of intravenous (IV) meloxicam administration without accompanying cornual block on post-surgical activity and

TABLE 1

Meloxicam pharmacokinetic parameters following single intravenous administration at 0.5 mg/kg.

| Parameter | Units | 16 | 18 | 23 | 31 | 40 | 44 | Geometric Mean | Min | Median | Max |
|---|---|---|---|---|---|---|---|---|---|---|---|
| $AUC_{EXTRAPOLATED}$ | % | 17.07 | 4.90 | 3.79 | 15.26 | 20.06 | 3.63 | 8.40 | 3.63 | 10.08 | 20.06 |
| $AUC_{INF}$ | hr * ug/mL | 89.19 | 100.62 | 83.70 | 72.19 | 79.43 | 72.35 | 82.34 | 72.19 | 81.57 | 100.62 |
| $AUMC_{INF}$ | hr * hr * ug/mL | 2400.61 | 3177.29 | 2472.52 | 1779.60 | 2351.43 | 1982.72 | 2321.34 | 1779.60 | 2376.02 | 3177.29 |
| C0 | ug/mL | 6.56 | 6.36 | 6.66 | 5.48 | 5.08 | 5.62 | 5.93 | 5.08 | 5.99 | 6.66 |
| Cl | mL/min/kg | 0.09 | 0.08 | 0.10 | 0.12 | 0.10 | 0.12 | 0.10 | 0.08 | 0.10 | 0.12 |
| $T½ \lambda z$ | hr | 19.16 | 22.76 | 21.53 | 17.84 | 21.08 | 20.10 | 20.35 | 17.84 | 20.59 | 22.76 |
| $\lambda z$ | 1/hr | 0.036 | 0.031 | 0.032 | 0.039 | 0.033 | 0.035 | 0.034 | 0.031 | 0.034 | 0.039 |
| MRT | hr | 26.92 | 31.58 | 29.54 | 24.65 | 29.60 | 27.40 | 28.19 | 24.65 | 28.47 | 31.58 |
| Vss | L/kg | 0.151 | 0.157 | 0.177 | 0.171 | 0.186 | 0.189 | 0.171 | 0.151 | 0.174 | 0.189 |
| Vz | L/kg | 0.155 | 0.163 | 0.186 | 0.178 | 0.192 | 0.200 | 0.178 | 0.155 | 0.182 | 0.200 |

TABLE 2

Meloxicam pharmacokinetic parameters following single oral administration at 1 mg/kg.

| Parameter | Units | 16 | 18 | 23 | 31 | 40 | 44 | Geometric Mean | Min | Median | Max |
|---|---|---|---|---|---|---|---|---|---|---|---|
| $AUC_{EXTRAPOLATED}$ | % | 23.01 | 30.01 | 39.43 | 4.14 | 5.85 | 33.02 | 16.71 | 4.14 | 26.51 | 39.43 |
| $AUC_{INF}$ | hr * ug/mL | 295.80 | 129.03 | 153.46 | 140.60 | 153.18 | 156.84 | 164.46 | 129.03 | 153.32 | 295.80 |
| $AUMC_{INF}$ | hr * hr * ug/mL | 19736.82 | 5205.64 | 8017.42 | 4730.72 | 6087.68 | 6837.34 | 7384.86 | 4730.72 | 6462.51 | 19736.82 |
| Cl/F | mL/min/kg | 0.06 | 0.13 | 0.11 | 0.12 | 0.11 | 0.11 | 0.10 | 0.06 | 0.11 | 0.13 |
| $C_{MAX}$ | ug/mL | 3.79 | 2.93 | 2.64 | 3.33 | 2.83 | 3.19 | 3.10 | 2.64 | 3.06 | 3.79 |
| $T½ \lambda z$ | hr | 43.29 | 24.85 | 34.10 | 19.97 | 21.41 | 27.83 | 27.54 | 19.97 | 26.34 | 43.29 |
| $\lambda z$ | 1/hr | 0.016 | 0.028 | 0.020 | 0.035 | 0.032 | 0.025 | 0.025 | 0.016 | 0.026 | 0.035 |
| MRT | hr | 66.72 | 40.35 | 52.24 | 33.65 | 39.74 | 43.59 | 44.90 | 33.65 | 41.97 | 66.72 |
| $T_{MAX}$ | hr | 10.00 | 12.00 | 12.00 | 12.00 | 12.00 | 12.00 | 11.64 | 10.00 | 12.00 | 12.00 |
| Vz/F | L/kg | 0.211 | 0.278 | 0.321 | 0.205 | 0.202 | 0.256 | 0.242 | 0.202 | 0.234 | 0.321 |
| MAT | hr | 39.81 | 8.77 | 22.70 | 8.99 | 10.14 | 16.19 | 15.07 | 8.77 | 13.17 | 39.81 |
| F | | 1.66 | 0.64 | 0.92 | 0.97 | 0.96 | 1.08 | 1.00 | 0.64 | 0.97 | 1.66 | weight gain in post-weaning calves was analyzed. The primary objectives of this trial were to (1) describe the compartmental pharmacokinetics of meloxicam in calves after IV administration at 0.5 mg/kg and (2) to determine the effect of meloxicam alone on cortisol response, heart rate, activity and weight gain in calves after scoop dehorning and thermocautery.

Twelve Holstein calves (16 wks of age; 140-205 kg) were randomly assigned to receive either meloxicam at 0.5 mg/kg (n=6) or a placebo IV immediately (<30 s) prior to scoop dehorning with a Barnes deborner and thermocautery. Behavioral assessment was conducted from 48 h before to 120 h after dehorning using 3-dimensional accelerometers. Heart rate was recorded continuously 48 h before and after dehorning with telemetric heart rate monitors. Body weight was determined prior to dehorning and at 6 and 10 days post-dehoming. Blood samples for cortisol and meloxicam determination were collected prior to dehorning and at 5, 10, 15, 20, 30, 60 minutes and 6, 22, 30, 45 and 52 h thereafter. Samples were analyzed by LC-MS for meloxicam concentrations and chemiluminescent immunoassay for cortisol concentrations. Data were analyzed with a random effects-mixed model using a univariate split-plot approach. Pharmacokinetic data were analyzed using compartmental modeling.

All experimental procedures in this study were approved by the Kansas State University Institutional Animal Care and Use Committee (IACUC) under the supervision of the University Veterinarian (Protocol #2694). Given that an untreated, dehorned control group was enrolled in the study, calves were assessed hourly for behavioral signs of excessive pain over a period of 10 hours after surgery. This was followed by twice daily monitoring for 7 days. Calves demonstrating postural changes, prolonged recumbency, anorexia and depression were scheduled to receive rescue analgesia with flunixin meglumine at 2.2 mg kg$^{-1}$ IV, BID. No calves were determined to require rescue analgesia during the course of the study.

2. Materials and Methods a. Experimental Cattle

Twelve Holstein bull calves approximately 16 wks of age and weighing between 140-205 kg were acquired from a commercial dairy located in Southwest Kansas. Upon arrival, the calves were given an eight-way clostridial vaccine (Covexin 8, Schering Plough, Summit, N.J.), a single SQ injection of tulathromycin (Draxxin, Pfizer, New York, N.Y.) at 2.5 mg/kg body weight, and doramectin (Dectomax Pour-on, Pfizer, New York, N.Y.) administered topically at 500 mcg/kg body weight. Amprolium (Corid, Duluth, Ga.) was added to the drinking water to provide 10 mg/kg PO for 5 days. Calves were surgically castrated by 6 days post-arrival and were acclimated for a further 14 days prior to study commencement.

b. Randomization and Group Assignment

The study design was a randomized, complete block parallel design with 2 treatment groups. Calves were blocked in pairs according to their weights determined approximately 14 days prior to study commencement. Calves were ranked by ascending weight in kilograms and assigned a computer-generated random number (Microsoft Excel 2007, Microsoft Corporation). In each pair, the calf with the highest random number was assigned to the meloxicam-treated group, while the calf with the lowest random number was designated as a placebo-treated control (n=6 calves/group).

Horn base diameter measured using calipers prior to study commencement ranged from 27 mm to 63 mm and horn length ranged from 29 mm to 115 mm. The mean (+standard error of the means (SEM)) diameter at the base of the horn was 39.4±5.0 mm in the placebo treated group (control) and 39.2±4.4 mm in the meloxicam treated group. The mean horn length was 64.0±16.9 mm in the control group and 58.6±15.1 mm in the meloxicam treated group. The mean (±SEM) pre-study weight of the calves was 168.8±8.3 kg in the control group and 162.3±7.2 kg in the meloxicam treated group.

c. Housing and Husbandry

Calves were housed in groups of 6 animals (n=3 steers from each treatment group in each pen) in a dry lot confinement facility at a Kansas State University Animal Resource Facility for the duration of the study. Housing consisted of straw bedding on an outdoor concrete pad (9.75 m×18.29 m) with a partial roof. During the adaptation period, each calf was tied with a rope halter to the pole fence within their pen for at least 10 minutes/day. Calves had free access to water and brome hay for the entire housing period with water provided ad libitum using self-filling water troughs. A balanced feedlot receiving ration composed of cracked corn, wheat middlings, oats, soymeal and a protein/vitamin/mineral supplement was fed at 3.6 kg/head/day. A complete analysis of the nutrient composition of the ration is presented in Table 3 below.

TABLE 3

Ration nutrient composition on an as fed and dry matter basis

| NUTRIENT | COMPOSITION | |
|---|---|---|
| | AS FED | DRY |
| NEm Megcal/CWT. | 83.10 | 95.23 |
| NEg Megcal/CWT. | 54.62 | 62.59 |
| TDN % | 76.46 | 87.62 |
| Fat | 4.61 | 5.29 |
| Crude Fiber | 4.18 | 4.79 |
| ADF | 5.61 | 6.43 |
| NDF | 12.84 | 14.71 |
| eNDF | 26.56 | 30.43 |
| Crude Protein % | 13.65 | 15.64 |
| Potassium % | 0.60 | 0.69 |
| Calcium % | 0.33 | 0.38 |
| Phosphorus % | 0.35 | 0.40 |
| Magnesium % | 0.14 | 0.16 |
| Sulfur % | 0.24 | 0.28 |
| Cobalt ppm | 0.06 | 0.07 |
| Copper ppm | 5.94 | 6.8 |
| Iron ppm | 50.64 | 58.0 |
| Manganese ppm | 20.75 | 23.8 |
| Selenium ppm | 0.14 | 0.17 |
| Zinc ppm | 309.55 | 354.7 |

NEm Megcal/CWT—Megcal of Net Energy for Maintenance (NEm) available per 100 pounds (CWT) of feed;
NEm Megcal/CWT—Megcal of Net Energy for Maintenance (NEm) available per 100 pounds of feed;
TDN—Total Digestible Nutrients;
ADF—Acid Detergent Fiber;
NDF—Neutral Detergent Fiber;
eNDF—Effective NDF;
ppm—parts per million d. Catheterization and Acclimatization Approximately 48 hours prior to study commencement, calves were restrained for intravenous catheter placement. Following restraint, the area over both the left and right jugular veins was clipped and disinfected using 70% isopropyl alcohol and povidone iodine scrub swabs.

The catheter sites was infiltrated with 2% lidocaine injection, I mL s.c., (Hospira Inc, Lake Forest, Ill.) prior to placement of 14 G×130 mm extended use catheters (MILA-CATH®, MILA International, Florence, Ky.) into each jugular, which were sutured to the skin using #3 nylon suture. Catheter plugs were fit to all catheters after insertion (Surflo Injection Plug, Terumo Medical Corp. Elkton, Md.). All study animals were fit with two catheters. One catheter was designated for drug or placebo administration and the other for blood sample collection. Catheter patency was maintained using a heparin saline flush containing 3 USP units heparin sodium/mL saline (Heparin Sodium Injection, Baxter Healthcare, Deerfield, Ill.).

Following catheter placement, calves were restrained twice daily using a rope halter to simulate study sampling procedures. Further more, calves were run through the chute handling facilities once daily and manipulated in the same manner as the proposed study procedures. Cattle were also fitted with commercially manufactured 3-dimensional accelerometers (GP 1 SENSR, Reference LLC, Elkader, Iowa) at the time of catheter placement in a similar manner as described in previous studies (Robert et al, 2009). Each device was placed in padded neoprene housing and affixed on the lateral aspect of the right rear limb just proximal to the fetlock. The accelerometers were left on the calves until study completion (approximately 7 days after placement). The entire apparatus and housing weighed less than 0.5 kg and did not impact mobility of the calves.

e. Treatment Administration

Calves were subjected to either meloxicam or placebo treatment as outlined below (n=6 steers/treatment). Doses were calculated based on individual animal bodyweight determined 14 hours prior to study commencement. The mean (+SEM) bodyweight used for dose calculation in the meloxicam-treated group was 162.33±7.15 kg and the control group was 168.83±8.34 kg. The IV dose was rounded to the nearest 0.5 mL and administered using a 20 mL syringe. Meloxicam or the placebo was administered immediately (<30 seconds) prior to commencement of the dehorning procedure.

1) Intravenous (IV) injection of 0.5 mg of meloxicam/kg body weight (METACAM® 5 mg/mL solution for injection (NADA 141-219), Boehringer Ingelheim Vetmedica, Inc. St Joseph, Mo.; Lot #118ZN12) was administered as a single bolus in the jugular vein using a designated catheter. The catheter was then flushed with 5 mL of heparin-saline and removed immediately after administration.

2) Intravenous sodium chloride injection (0.9% Sodium Chloride Injection USP, Baxter Healthcare Corp, Deerfield, Ill.) was administered at a volume based on a hypothetical dose of 0.5 mg/kg meloxicam injection.

Observers and analytical chemists in the study were masked to treatment group allocation.

f. Dehorning

Dehorning procedures commenced at 0800 h CST with calves dehorned at 25-minute intervals to facilitate intensive blood sampling during the immediate post-dehorning period. All dehorning procedures were performed by a single experienced veterinary student (CRP). Prior to dehorning, all calves were restrained in a chute with a head gate. Each calf was additionally restrained using a rope halter. The base of the horn was then clipped and the horn removed using a Barnes dehorning instrument (Stone Manufacturing & Supply Company, Kansas City, Mo.). Briefly, the opposing blades of the instrument were aligned with the base of each horn at the skin-horn junction. The handles of the instrument were then closed slowly to ensure proper placement of the instrument. Once optimal positioning was achieved, the handles were spread quickly apart to engage the blades and cut off the horn. Hemostasis was achieved through thermocautery using a preheated electric dehorning iron (Stone Manufacturing & Supply Company, Kansas City, Mo.). After dehorning, calves remained standing but unrestrained in the chute for 20 minutes to facilitate intensive blood sampling. Subsequent samples were collected in housing pens with calves restrained using a rope halter.

g. Blood Sample Collection

Twelve milliliters of whole blood for cortisol determination in all study calves and meloxicam determination in treated calves were collected into syringes using the preplaced jugular catheter immediately prior to drug or placebo administration, and at 5, 10, 15, 20, 30, 60 minutes and again at 6, 22, 30, 45 and 52 hours thereafter. Catheters were removed after final blood collection. Immediately after obtaining each blood sample, 3 mL of heparin saline flush was used to maintain patency of the catheter as previously described. Blood was immediately transferred to 6 mL, serum and lithium heparin vacutainer tubes (BD Diagnostics, Franklin Lakes, N.J.) for cortisol and drug determination, respectively. The vacutainer tubes were stored on ice for no more than 60 minutes pending sample processing. Thereafter, blood samples were centrifuged at 1,600×g for 15 minutes at 4° C. Serum and plasma were pipetted from their respective tubes and placed in cryovials identified with calf ID, date, timepoint sample, and treatment group. The samples were stored at −80° C. prior to sample analysis. All samples were analyzed within 60 days of sample collection.

h. Cortisol Determination

Serum cortisol concentrations were determined using a solid-phase competitive chemiluminescent enzyme immunoassay and an automated analyzer system (Immulite 1000 Cortisol, Siemens Medical Solutions Diagnostics, Los Angeles, Calif.) as previously described using an assay validated in bovine plasma (Coetzee et al., 2007). A sample volume of 100 μL, was used in each assay well. The reported calibration range for the assay is 28 to 1,380 nmol/L with an analytical sensitivity of 5.5 nmol/L.

Accelerometers

The accelerometers sampled at 100 Hz and summarized values for the selected variables every 5 seconds. Five variables were recorded by the accelerometers for each 5-second interval: average acceleration in each of the three axes (X, Y, and Z), the combined average magnitude for all three axes, and the maximum combined vector magnitude. At trial completion, data were downloaded from each device for analysis using previously validated and described methods (White et al, 2008; Robert et al, 2009).

j. Heart rate determination

Heart rate (HR) data were recorded 48 hours before and after dehorning for each calf. HR was recorded and analyzed using a commercially-available heart rate monitor and software (RS800 and Polar Pro Trainer Equine Edition, Polar Electro, Inc, Lake Success, N.Y.), as previously described (Kotschwar et al, 2009). The HR monitor consisted of a transmitter placed over the heart in the left foreflank attached to a girth strap placed around the heart girth of the calves, and a wrist unit attached to the elastic strap which received and recorded the signal from the transmitter. Girth straps were kept in position using a cohesive flexible bandage (Oasis Bandage, Fisher Healthcare, Houston, Tex.). Appropriate conductance for the electrodes on the strap, one positioned on the sternum and one over the right scapula, was facilitated by use of ultrasound gel (Medline Industries Inc. Mundeline, Ill.). The transmitter measured the electric signal (ECG) of the heart every 15 seconds. Prior to study commencement, the HR wrist unit time was synchronized with the stopwatches used for all other sample collection. The corresponding HR within 15 seconds of each time point was used for analysis.

k. Average Daily Weight Gain

Calves were weighed individually at approximately the same time of day prior to dehorning and at 6- and 10-days after dehorning using a commercial livestock scale (For-Most Livestock Equipment, Hawarden, Iowa). Food and water was not withheld prior to each weighing, which also occurred at approximately the same time each day. Average daily gain (ADG) was calculated by subtracting the pre-dehorning weight from the post-dehorning weight and dividing this by the number of days that passed between weigh dates.

1. Plasma Meloxicam Determination

Plasma concentrations of meloxicam (m/z 352.09→114.90) were determined with HPLC (Shimadzu Prominence, Shimadzu Scientific Instruments, Columbia, Md., USA) and mass spectrometry (API 2000, Applied Biosystems, Foster City, Calif., USA). Plasma samples or standards (100 µL) were added to 100 µL of internal standard (piroxicam 0.5 µg/mL in methanol, m/z 332.12→95.10) and 300 µL of methanol with 0.1% formic acid to precipitate the proteins. The samples were vortexed for 5 seconds and centrifuged for 10 minutes at 10,000×g. The supernatant, 200 µL, was transferred to an injection vial with the injection volume set to 10 µL. The mobile phase consisted of A: acetonitrile and B: 0.1% formic acid at a flow rate of 0.4 mL/min. The mobile phase consisted of 85% B from 0-0.5 minutes with a linear gradient to 50% B at 2.5 minutes which was maintained until 3 minutes, followed by a linear gradient to 85% B at 4 minutes with a total run time of 5 minutes. Separation was achieved with a C8 column (Supelco Discovery C8, 50 mm×2.1 mm×5 µm, Sigma-Aldrich, St. Louis, Mo., USA) maintained at 40° C. The standard curve was linear from 0.01 µg/mL to 10 µg/mL and was accepted if the correlation coefficient exceeded 0.99 and predicted values were within 15% of the actual values. The accuracy of the assay was 103±7% of the actual value and the coefficient of variation was 7% determined on replicates of 5 each at 0.025, 0.5, and 5 µg/mL.

m. Pharmacokinetic Analysis

Compartmental pharmacokinetic analysis of the meloxicam time concentration data was performed using a commercially-available software program (WinNonlin, Pharsight Corporation, Cary, N.C.). A two-compartment model with first order elimination was judged to fit the data best, based on visual inspection of predicted versus observed data plots and two measures of goodness of fit (Aikaike Information Criterion and Schwarz Bayesian Criterion). The weighted data $(1/C(t)^2)$ were therefore fitted to exponential equation 1 by nonlinear regression analysis.

$$C(t) = A^* e^{-\alpha^* t} + B^* e^{-\beta^* t} \quad (1)$$

Where: C is the predicted plasma drug concentration at any given time t; B ($\beta$) and A ($\alpha$) are the intercepts (slopes) obtained by extrapolating the terminal linear phase and the linear segment obtained by the method of residuals, respectively, to t=0.

Primary and secondary pharmacokinetic parameters were calculated from these intercepts and slopes according to standard equations as described by Gibaldi and Perrier (1982). These included the volume of the central and peripheral compartments as well as the apparent volume of distribution at steady-state ($V_c$, $V_2$ and $T_{ss}$); total body clearance and clearance from the central compartment due to distribution into the peripheral compartment (CL and $CLD_2$), micro-rate constants for the drug's movement between the central and peripheral compartments ($k_{12}$ and $k_{21}$); elimination rate constant and half-life ($k_{10}$ and $T_{1/2el}$); and half-lives for the distribution and elimination phases ($T_{1/2\alpha}$ and $T_{1/2\beta}$). Descriptive parameters were also calculated, including the back-extrapolated maximum plasma concentration ($C_0$), area under the time-concentration curve and its first moment (AUC and AUMC) and the drug's mean residence time in the body (MRT).

n. Data Analysis and Statistics

Hypothesis tests for cortisol, heart rate and ADG were conducted using JMP 5.1.2 analytical software (SAS Institute, INC, Cary, N.C., USA) (Sall et al., 2004). For statistical analysis, the calf was considered the experimental unit. The mean (±SEM) and the mean difference, where appropriate, were calculated for each outcome variable at each time point.

Repeated measures data (heart rate and cortisol concentrations at each time point) were analyzed using a univariate split-plot approach. A random effects-mixed model was constructed with treatment, time and time*treatment interaction designated as fixed effects. In this model, animal nested in treatment was designated as a random effect to account for the between subject effects. Statistical significance was designated a priori as $p<0.05$. Where significant time*treatment interactions were detected, planned comparisons between different time*treatment combinations were conducted using two-sided Student t-tests (Ramsey and Schafer, 2002). Individual confidence levels were controlled for all planned comparisons.

Peak cortisol concentrations (Cmax), time to peak cortisol concentration (Tmax) and area under the time-effect curve (AUEC) was determined for cortisol as previously described (Coetzee et al, 2008) with the commercially available software program WinNonlin (Pharsight Corporation, Cary, N.C.) using the linear trapezoidal rule. Analysis of variance (ANOVA) was employed to evaluate differences in single measurement, normally distributed data (ADG, Cmax, and AUEC) and the Kruskal-Wallis Test was used to analyze non-parametric data (Tmax). Statistical significance was designated a priori at $p<0.05$.

Accelerometer data were imported into a commercial data mining software program (insightful Miner, Insightful Corporation, Seattle, Wash.), and a previously validated decision tree (Robert et al 2009, White et al 2008) was used to classify the behavior as lying, standing, or walking for each 5-second interval. Following classification, data were aggregated on an hourly basis by the summing of the counts of 5-second intervals spent in each behavior. Hours with known periods of human intervention (feeding, sample collection, animal processing, and treatment administration) were removed equally from calves in both treatment groups. The remaining hourly behavioral data from both replicates of the trial were imported into a statistical program (SAS 9.1, SAS Institute, Cary, N.C.) for analysis. The proportion of time calves spent in each activity was modeled using logistic regression (PROC GLIMMIX) to evaluate potential associations between lying behavior and time relative to dehorning (pre- or post-), treatment (Meloxicam or control), and the interaction between these variables. Random effects were included in the model to account for a lack of independence in each sampling due to multiple calves housed within the same pen and repeated measures on individual calves.

3. Results a. Meloxicam Pharmacokinetics

Figure 2:
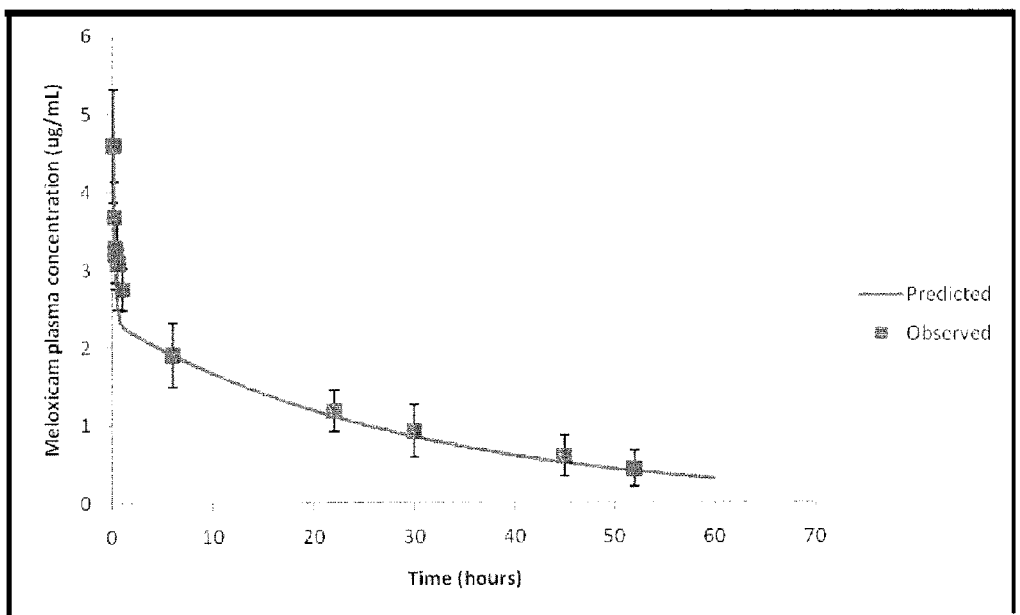
FIG. 2 is a graph of the average predicted time-concentration curve compared to observed data (+SD; n=6 calves) after administration of meloxicam at 0.5 mg/kg IV from Example 2.

The average observed and predicted plasma time-concentration curve of meloxicam following IV administration at 0.5 mg/kg bodyweight in calves is presented in FIG. 2. The mean pharmacokinetic parameters calculated after fitting this model to the data are summarized in Table 4, below.

TABLE 4

Mean plasma pharmacokinetic parameters for meloxicam after IV administration at 0.5 mg/kg body weight determined using a two-compartment model

| Parameter | Units | Mean | Standard error | Median | Minimum | Maximum |
|---|---|---|---|---|---|---|
| $V_c$ | mL/kg | 94.88 | 9.04 | 101.46 | 63.51 | 115.67 |
| $K_{10}$ | 1/hr | 0.075 | 0.012 | 0.075 | 0.034 | 0.11 |
| $K_{12}$ | 1/hr | 2.70 | 0.78 | 2.33 | 0.44 | 5.90 |
| $K_{21}$ | 1/hr | 2.20 | 0.39 | 2.25 | 0.61 | 3.56 |
| $T_{1/2}el$ | hr | 10.91 | 2.19 | 9.43 | 6.47 | 20.70 |
| A | 1/hr | 4.94 | 1.56 | 4.59 | 1.07 | 9.53 |
| B | 1/hr | 0.034 | 0.0034 | 0.036 | 0.019 | 0.042 |
| $T_{1/2}\alpha$ | hr | 0.22 | 0.087 | 0.15 | 0.073 | 0.65 |
| $T_{1/2}\beta$ | hr | 21.86 | 3.03 | 19.22 | 16.56 | 36.37 |
| A | ug/mL | 6.17 | 1.51 | 6.50 | 1.00 | 11.00 |
| B | ug/mL | 2.57 | 0.15 | 2.45 | 2.16 | 3.08 |
| $C_0$ | ug/mL | 5.55 | 0.60 | 4.97 | 4.32 | 7.87 |
| AUC | hr * ug/mL | 81.02 | 10.58 | 77.21 | 52.22 | 129.11 |
| AUMC | hr * hr * ug/mL | 2748.34 | 819.56 | 2058.62 | 1234.83 | 6748.92 |
| MRT | hr | 31.24 | 4.37 | 27.49 | 23.64 | 52.27 |
| CL | mL/hr/kg | 6.64 | 0.76 | 6.49 | 3.87 | 9.57 |
| $V_{SS}$ | mL/kg | 193.94 | 10.34 | 199.16 | 159.67 | 226.38 |
| $V_2$ | mL/kg | 99.07 | 7.85 | 93.46 | 82.47 | 133.81 |
| $CLD_2$ | mL/hr/kg | 225.18 | 47.43 | 205.52 | 50.13 | 375.01 |

$V_c$—volume of the central compartment;
$V_2$—volume of the peripheral compartment;
$V_{SS}$: apparent volume of distribution at steady-state;
CL—total body clearance;
$CLD_2$—clearance from the central compartment;
$k_{12}$ and $k_{21}$ - micro-rate constants for the drug's movement between the central and peripheral compartments;
$k_{10}$ - elimination rate constant;
$T_{1/2}el$ - half-life;
$T_{1/2}\alpha$ - half-life for the distribution phases;
$T_{1/2}\beta$ - half-life for the elimination phase;
C0 - extrapolated maximum plasma concentration;
AUC—area under the time-concentration curve;
AUMC—area under the first moment time-concentration curve;
MRT—mean residence time of the drug in the body.

The data fit a 2-compartment model characterized by rapid distribution of meloxicam from the central to the peripheral compartments after IV administration (mean. $T_{1/2\alpha}=0.22\pm0.087$ hours), This was followed by a slower decline in mean plasma meloxicam concentrations governed by metabolism and excretion processes (mean $T_{1/2\beta}=21.86\pm3.03$ hours). Collectively this resulted in an elimination half-life ($T_{1/2el}$) of 10.91±2.91 hours. The extrapolated mean (±SEM) plasma meloxicam concentration ($C_o$) immediately following IV administration was 5.55±0.60 µg/mL with a mean (±SEM) volume of distribution ($V_{ss}$) of 193.94±10.34 mL/kg and a plasma clearance (CL) of 6.64±0.76 mL/h/kg. The mean (±SEM) area under the plasma meloxicam concentration time curve (AUC) was 81.02±10.58 hr·ug/mL.

b. Cortisol

Mean non-compartmental analysis parameters for cortisol are summarized in Table 5 below.

TABLE 5

Mean peak serum cortisol concentrations (Cmax), time to peak concentration (Tmax) and area under the time-effect curve (AUEC) for cortisol determined using non-compartmental analysis

| Cortisol parameters | Control | Meloxicam | P value |
|---|---|---|---|
| Tmax (min) | 15.83 ± 4.92 | 19.17 ± 9.17 | 0.68 |
| Cmax (nmol/L) | 159.17 ± 11.032 | 165.00 ± 14.84 | 0.76 |
| AUEC minute · nmol/L | 133,584 ± 18,039 | 122,961 ± 20,441 | 0.70 |

Cmax: Peak cortisol concentrations,
Tmax: time to peak cortisol concentration,
AUEC: area under the time-effect curve for cortisol determined using non-compartmental analysis.

Figure 3:
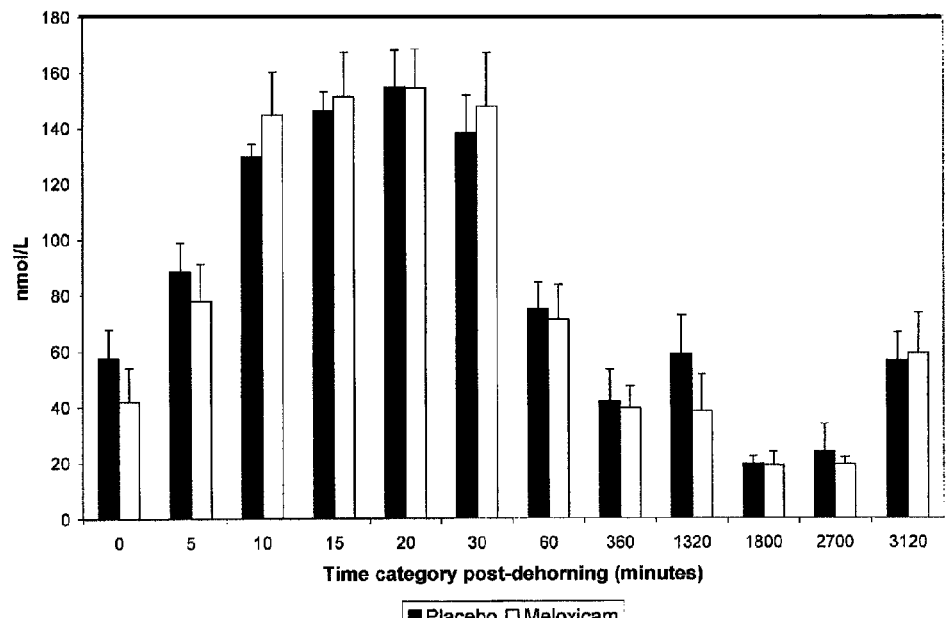
FIG. 3 is a graph of the mean (±SEM) serum cortisol concentrations (nmol/L) in calves receiving 0.5 mg/kg meloxicam or placebo IV immediately (<30 s) prior to dehorning from Example 2.

Mean serum cortisol concentrations over time for the meloxicam and placebo treated groups are presented in FIG. 3. A mean (±SEM) peak serum cortisol concentration of 165.00±14.84 nmol/L was observed at 19.17±2.00 minutes after dehorning in the meloxicam treated group. This was similar to the mean peak cortisol concentration of 159.17±11.03 nmol/L (p=0.76) observed at 15.83±2.00 minutes (p=0.68) in the placebo-treated control group. The integrated cortisol response as represented by the area under the effect curve (AUEC) for cortisol was numerically lower in the meloxicam treated calves (122,961±20,441 minute·nmol/L) compared with the placebo-treated control calves (133,584±18,039 minute·nmol/L) however, this difference was also not significant (p=0.70).

c. Activity and Behavior

Figure 4:
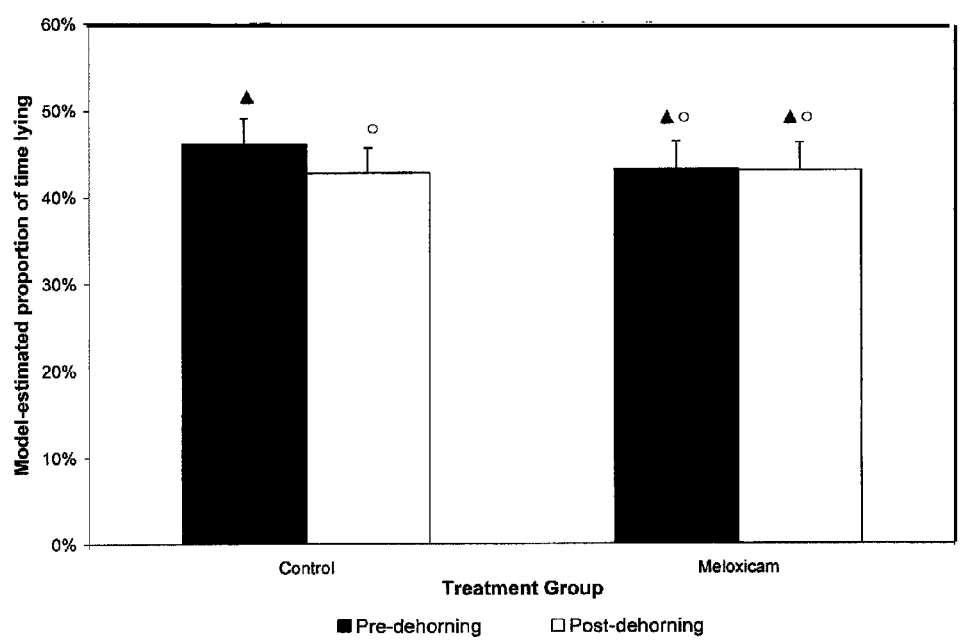
FIG. 4 is a chart of the model estimated proportion of time calves spent lying by treatment group and time relative to dehorning (pre=48 hr, post=168 h) from Example 2. Model included random effects for calf identification and trial replicate. Unique symbols above columns denote statistical differences (p<0.05) between proportions.

Data from one calf (calf number 7, meloxicam group) was not available for analysis due to accelerometer malfunction resulting in loss of data. After removal of processing time-periods and known times of human intervention, data were available for analysis on five calves in the meloxicam group, representing 136 hours in the pre-dehorning period and 495 hours in the post-dehorning period. There were 162 and 597 hours available for analysis in the six control calves for the pre- and post-dehorning periods, respectively. The effect of dehorning on lying behavior was modified by meloxicam administration, as evidenced by the significant (p<0.01) interaction between time relative to dehoming (pre vs. post) and treatment group (meloxicam vs. control). Calves in the control group spent a lower proportion (42.7%) of time lying post-dehorning compared to pre-dehoming (46.1%); however, there were no significant differences (p=0.40) in the proportion of time the meloxicam calves spent lying pre- or post-dehorning (43.1%, 43.0%, respectively) (FIG. 4).

d. Heart Rate (HR)

Figure 5:
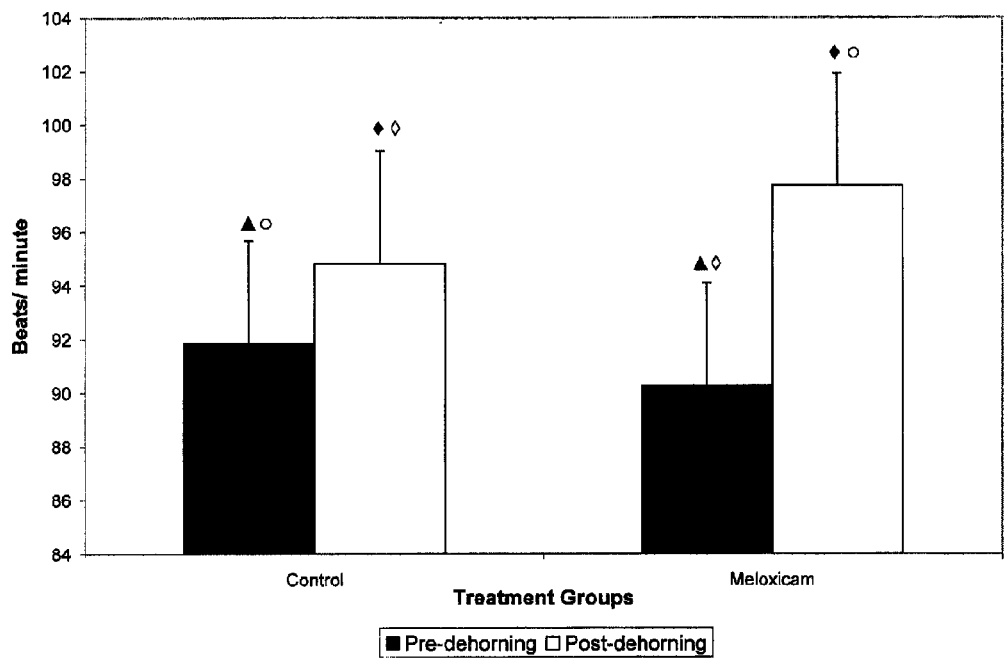
FIG. 5 is a chart of the mean (±SEM) heart rate (beats/minute) in calves receiving 0.5 mg/kg meloxicam or placebo IV immediately (<30 s) prior to dehorning (pre=48 h, post=48 h). Unique symbols above columns denote statistical differences (p<0.05) between proportions.

The mean HR in meloxicam and placebo treated calves in the period before and after dehorning, is presented in FIG. 5. There was a 5 beat/minute increase in mean HR after dehorning across treatment groups (p<0.0001) but there was no difference between treatment groups across periods (1±6 beats/minute; p=0.9). However, there was also evidence of a significant treatment group*period interaction (p<0.0001).

The mean HR was not significantly different between calves assigned to the control group (92±4 beats/minute) and the meloxicam treated group (90±4 beats/minute) prior to dehorning (p=0.79). After dehorning, the mean HR increased by 3 beats/minute (p<0.0001) in the placebo treated calves and 7 beats/minute (p<0.0001) in the meloxicam treated calves. However, the difference between treatment groups post-dehorning was not statistically significant (Mean Difference: 3±6 beats/minute; p=0.62).

e. Average Daily Gain (ADG) in Body Weight

Figure 6:
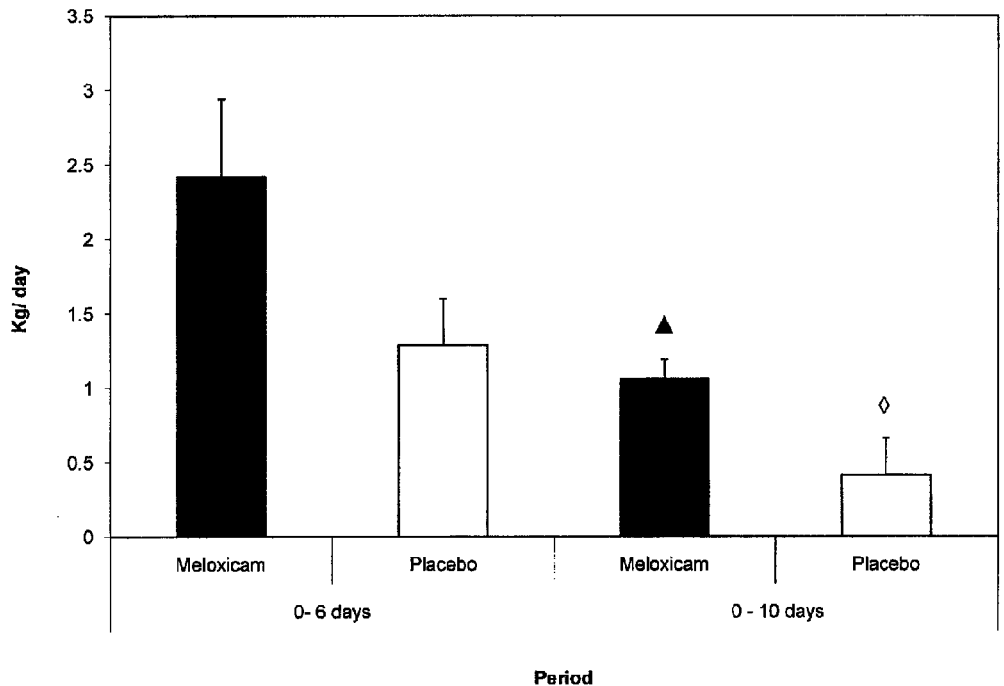
FIG. 6 is a chart of the mean Average Daily Gain (ADG) (kg) (±SEM) at 6- and 10-days post-dehorning after placebo or meloxicam administration at 0.5 mg/kg IV prior to dehorning in Example 2. Unique symbols above columns denote statistical differences (p<0.05) between proportions.

The mean ADG in calves in the placebo or meloxicam treated groups at 6 and 10 days after dehoming is presented in FIG. 6. Calves receiving meloxicam prior to dehoming gained an average of 2.42±0.52 kg/day over 6 days post dehorning. This was not statistically different from the mean average daily gain in body weight of 1.29±0.31 kg/day in the placebo treated (control) group over the same period (p=0.091). However, calves receiving meloxicam prior to dehorning gained an average of 1.05±0.13 kg/day over 10 days post-dehorning. This was significantly greater than the mean average daily gain in body weight of 0.40±0.25 kg/day in the placebo treated (control) group over the same period (p=0.0418).

f. Summary

Plasma meloxicam concentrations were detectable for 50 hours post-administration and fit a 2-compartment model with a rapid distribution phase (mean $T_{1/2\gamma}$=0.22±0.087 h) and a slower elimination phase (mean $T_{1/2\beta}$=21.86±3.03 h). Calves in the control group spent a lower proportion of time lying post-dehoming (42.7%) compared to pre-dehoming (46.1%). However, there were no significant differences in the lying time in the meloxicam-treated calves pre- or post-dehorning (43.1%, 43.0%, respectively). Calves receiving meloxicam prior to dehoming gained on average 1.05±0.13 kg body weight/day compared with 0.40±0.25 kg body weight/day in the placebo-treated calves over 10 days post dehorning (p=0.0418). Although dehorning was associated with a significant increase in serum cortisol concentrations and heart rate, there was no significant difference between the meloxicam- and placebo-treated groups. These findings suggest that administration of meloxicam without local anesthesia immediately prior to dehorning may not mitigate signs of acute distress (cortisol and heart rate), but appears to have long term behavioral and performance benefits.

Example 3

Oral Meloxicam reduces the incidence of BRD in bulls following castration

In this study, 149 bull calves were randomly assigned to receive either meloxicam (n=71) delivered orally at a dosage of 1 mg/kg body weight or a placebo (n=74) prior to castration. The incidence of Bovine Respiratory Disease (BRD): pneumonia) in bulls receiving meloxicam prior to castration was 10.3% compared with 20.69% in the placebo-treated control group. The probability of developing BRD was therefore significantly greater in the placebo treated bulls compared with the meloxicam treated bulls (p=0.0092). Therefore the odds of developing BRD are 2.5 times greater in bulls not receiving meloxicam than bulls that did receive meloxicam prior to castration. We found a significant reduction in cases of BRD in bulls receiving meloxicam prior to castration compared with cases in bulls receiving a placebo. The benefits of this are reduced morbidity, reduced drug costs and improved performance.

Example 4

Meloxicam and Post-Castration Activity of Cattle

1. Introduction

Castration in weaned calves is stressful and affects profitability by reducing ADG and increasing susceptibility to disease. The objective of this study was to examine the effect of castration on performance, health, and temperament of bulls following surgical castration upon arrival at a stocker unit, as compared to previously castrated steers. The study involved 258 cross-bred male beef calves (145 bulls and 113 steers) that were purchased from a livestock commission company in the southeastern United States.

Figure 7:
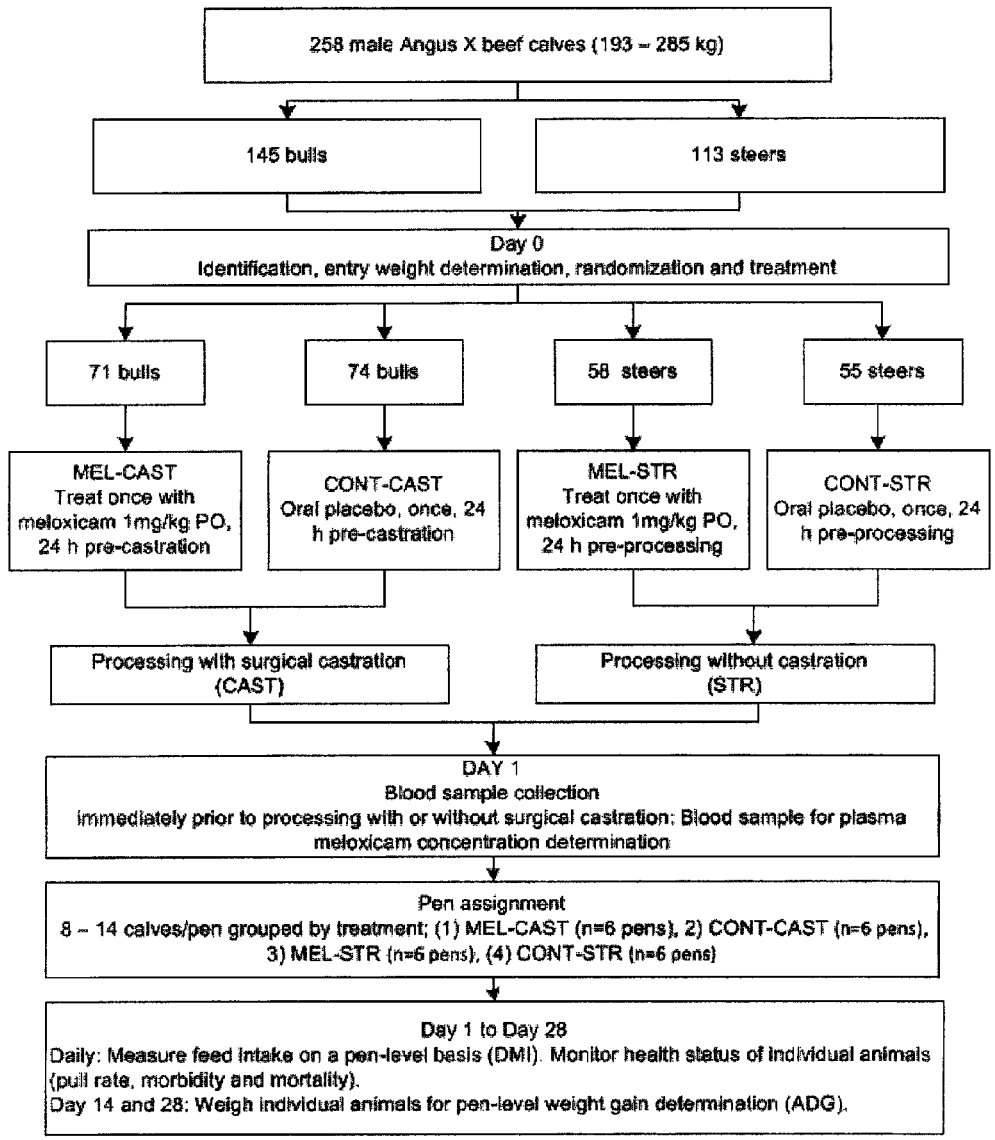
FIG. 7 is a flowchart of the study carried out in Example 4. On day 1, bulls were surgically castrated (CAST) and steers were submitted to processing without castration (STR)

2. Materials and Methods a. Animals, Housing, Treatment Allocation, and Processing This study was designed as a stratified 2-arm parallel trial. The strata were calves received as steers (STR) vs. calves castrated on arrival (CAST), and the treatment was meloxicam (MEL) or placebo (CONT) (FIG. 7). Two hundred fifty eight medium-large frame, polled, Continental x British or British crossbred bull (n=145) and steer (n=113) calves ages 8-10 months and weighing 193 to 285 kg were procured from sale barns in southeastern Tennessee. Calves were shipped approximately 1,086 km to the Kansas State University Beef Stocker Unit outside Manhattan, Kans., where they were housed for the duration of the study. Calves were maintained on open pens that consisted of a combination of concrete aprons and dirt pens. Each pen was 192 $m^2$ with an allowance of approximately 14-24 $m^2$/head. A maximum of 14 head/pen was allowed, Calves arrived in March 2010 in 3 loads (Lots) of mixed gonadal status carrying 83, 87, and 88 calves, respectively. Upon arrival, calves were unloaded and sorted (d 0).

During sorting, calves were individually weighed and given an individual identification tag in the right ear. A tissue sample for bovine viral diarrhea (BVD) analysis was taken from the left ear using a specialized ear notch device (Caisley International GmbH, Bocholt, Germany). Calves were determined to be bulls or steers by palpation and were then randomly assigned to either a meloxicam- or placebo-treated group by a randomization table generated using Excel (Microsoft Corp., Redmond, Wash.).

After randomization, 71 bulls (MEL-CAST) and 58 steers (MEL-STR) were scheduled to receive meloxicam. Meloxicam tablets (Meloxicam Tablets USP 15 mg [NDC 29300-125-01], Unichem Pharmaceuticals USA Inc. Rochelle Park, N.J.; Lot # GMMH09021) were orally administered at 1 mg meloxicam/kg body weight (BW). The dose was rounded down to the nearest whole tablet so that no animal received a dose exceeding 1mg/kg. After randomization, 74 bulls (CONT-CAST) and 55 steers (CONT-STR) were scheduled to receive treatment with the placebo. Calves in the placebo-treated control group received an equivalent oral dose of D(+)-lactose monohydrate (Fluka Analytical, Buchs, Germany), a pharmacologically inactive excipient used in the manufacture of meloxicam tablets. Both doses were calculated using arrival weights and were administered by suspending crushed meloxicam tablets or placebo in approximately 50 ml of water and delivering this orally with a dosing syringe within 30 seconds of suspension. All steers were allotted to the uncastrated control treatment and all bulls were allotted to the surgical castration treatment. After processing, calves were housed in 6 staging pens of 15 to 16 calves, where they remained overnight and were given prairie hay and water.

Approximately 24 h after the dosing (d 1), calves were processed. Specifically, the calves were brought back through the processing chute and given a commercial modified-live, viral respiratory vaccine containing infectious bovine rhinotracheitis virus; parinfluenzavirus-3; bovine viral diarrhea virus; bovine respiratory syncytial virus; Mannheimia haemolytica (Pyramid 5+ Presponse SQ, Fort Dodge Animal Health, Wyeth, Madison, N.J.); a multivalent clostridial vaccine (Calvary 9, Intervet/Schering-Plough Animal Health, Boxmeer, Netherlands); injectable ivermectin at 200 µg/kg BW (Ivomec, Merial Limited, Duluth, Ga.); and a metaphylactic antimicrobial, ceftiofur crystalline free acid at 6.6 mg/kg BW (Excede, Pfizer Animal Health, New York, N.Y.). Products were administered according to label instructions.

Processing and surgical castration was performed by the same operator to minimize variation in procedure. Castration was performed using open surgical technique without administration of a local anesthetic, consistent with standard industry practice in the United States (Coetzee et al, 2010a). Briefly, the scrotum of each calf was cleaned with dilute chlorohexidine disinfectant and incised longitudinally with a Newberry knife (Jorgensen Lab, Loveland, Colo.). The testes and spermatic cords were exteriorized by blunt dissection and the cremaster was broken using manual traction. The spermatic cords were cut using a White's Double Crush emasculator (Jorgensen Lab, Loveland, Colo.) applied for approximately 30 seconds. Steers were subjected to the same handling procedures apart from knife cutting and castration.

After processing, calves were sorted into study pens. Calves from each load were ranked by BW and systematically allocated to pens based upon weight, gonadal status, and treatment group. For each of the 3 loads, 2 pens were assigned to each of the 4 treatment groups for a total of 24 pens. After allocation each pen contained 8 to 14 calves of the same treatment subclass: 6 pens of 10 to 14 calves in the CONT-CAST group, 6 pens of 10 to 14 calves in the MEL-CAST group, 6 pens of 8 to 10 calves in the MEL-CAST group and 6 pens of 8 to 11 calves in the MEL-STR group. All pens were 12 m×16 m with 12 m of bunk space and one water source per pen. Calves were reweighed on day 14. Additionally, calves were revaccinated with the viral respiratory vaccine (Pyramid 5+ Presponse SQ, Fort Dodge Animal Health, Wyeth, Madison, N.J.) and given a pour-on eprinomectin at 500 µg/kg BW (Eprinex, Merial Limited, Duluth, Ga.) at this time. Final BW was obtained at the end of the study on day 28.

b. Collection of Samples

Blood samples to confirm meloxicam dosage were obtained on day 1 via jugular venipuncture immediately following both surgical and sham castration. Blood also was collected from the placebo-treated calves to maintain equality between study groups and to ensure that personnel remained masked to drug treatment group. Blood samples were collected in 6 mL evacuated tubes that contained lithium heparin (Vacuette plasma tubes, Greiner Bio-One, Monroe, N.C.) and stored on ice for up to 2 hours before processing. Blood samples were centrifuged for 10 min. at 1,500×g. Plasma was then harvested, placed in cryovials, and frozen at −70° C. until analysis. All samples were analyzed within 60 days after sample collection.

c. Plasma meloxicam analysis

Plasma concentrations of in eloxicam (m/z 352.09-114.90) were determined with high-pressure liquid chromatography (Shimadzu Prominence, Shimadzu Scientific Instruments, Columbia, Md.) and mass spectrometry (API 2000, Applied Biosystems, Foster City, Calif.). Plasma samples or standards (100 µl) were added to 100 µL of internal standard (piroxicam 0.5 µg/ml in methanol, m/z 332.12-95.10) and 300 µL of methanol with 0.1% formic acid to precipitate the proteins. The samples were vortexed for 5 seconds and centrifuged for 10 min at 10,000×g. The supernatant, 200 µL, was transferred to an injection vial with the injection volume set to 10 µL. The mobile phase consisted of A: acetonitrile and B: 0.1% formic acid at a flow rate of 0.4 mL/min. The mobile phase consisted of 85% B from 0 to 0.5 min with a linear gradient to 50% B at 2.5 min, which was maintained until 3 min, followed by a linear gradient to 85% B at 4 min, with a total run time of 5 min. Separation was achieved with a C8 column (Supelco Discovery C8, 50 mm×2.1 mm×5 µm; Sigma-Aldrich, St. Louis, Mo.) maintained at 40° C. The standard curve was linear from 0.01 to 10 µg/mL and was accepted if the correlation coefficient exceeded 0.99 and predicted values were within 15% of the actual values. The accuracy of the assay was 103%±7% of the actual value, and the coefficient of variation was 7%, determined on replicates of 5 each at 0.025, 0.5, and 5 µg/mL.

d. Temperament score

During processing on days 0, 1, and 14, animal temperament in the hydraulic squeeze chute was evaluated by a single observer masked to drug treatment group using a 4-point scale (1=calm, no movement; 2=restless shifting; 3=squirming, occasional shaking of the chute; 4=continuous vigorous movement and shaking of the chute, rearing, twisting, and struggling) (Voisinet et al., 1997).

e. Nutrition Program

All ingredients are reported on a DM basis. The arrival diet consisted of prairie hay containing 7.0% crude protein (CP) 0.44 mcal/kg net energy gain (NEg). Beginning 1 day after arrival, the calves were fed a total mixed ration (TMR) consisting of prairie hay, alfalfa hay, dry rolled corn, wet corn gluten feed, and a commercial premix pellet (Cargill Animal Nutrition, Minneapolis, Minn.). The percentage of each ingredient in the diets is presented in Table 6. This ration was formulated to contain 15.2% CP and 1.09 meal/kg NEg. Beginning 8 days post-arrival and continuing through day 18, calves were fed a TMR incorporating the same ingredients as above, but containing 15.2% CP and 1.14 mcal/kg NEg. On day 19 and continuing through the study endpoint, calves were fed a TMR utilizing the same ingredients formulated to contain 14.4% CP and 1.20 meal/kg NEg. Daily feed allowances to each pen were recorded. Water was provided ad libitum. Feed bunks were evaluated twice daily, and the weight of feed not consumed was used as a basis for the amount delivered at the next feeding.

TABLE 6

Dietary components of the rations fed in the study (as-fed).

| DOF | Supplement[1] | Dry rolled corn | WCGF[2] | Prairie hay | Alfalfa hay |
|---|---|---|---|---|---|
| 1 to 7 | 3% | 28% | 30% | 16% | 23% |
| 8 to 18 | 3% | 29% | 37% | 16% | 15% |
| 19 to 28 | 3% | 36% | 37% | 15% | 9% |

DOF: Days on Feed.
[1]Supplement contains 600 g/to monensin: Crude Protein - 15%
[2]Wet Gluten Feed (Sweetbran, Cargill Animal Nutrition, Minneapolis, MN)

f. Health Program

Kansas State University Beef Stocker Unit personnel conducted twice daily evaluations of the cattle and were masked to drug treatment assignment throughout the study. Animals were deemed "sick" based on subjective criteria including general appearance and attitude, gauntness, and reluctance to move. If a sick calf was identified it was removed from the pen, brought to the processing unit, and its rectal temperature was obtained.

To be considered a case of BRD, calves had to demonstrate an absence of abnormal clinical signs attributable to organ systems other than the respiratory system and had to meet the following case definition based on presenting clinical signs:

1) Observed clinical signs of BRD evaluated using a visual depression scoring system (Table 7) (Perino and Apley, 1998). A minimum depression score of 2 was required for a diagnosis of BRD.
2) A rectal temperature of >103.6° F. (39.78° C.) (Duff and Galyean, 2007).

TABLE 7

Depression scoring system used to determine sickness and diagnose Bovine Respiratory Disease (BRD) in calves (adapted from Perino and Apley, 1998)

| Depression score | Clinical signs |
|---|---|
| 0 | Normal, no signs of depression |
| 1 | Noticeable depression without apparent signs of weakness. Slower than pen mates but still raises head when approached and does not appear weak, actively follows your movements with a raised head. |
| 2 | Marked depression with moderate signs of weakness without a significantly altered gait. Stands with head lowered, will perk up when approached but will return to depressed stance, moves slowly and falls towards back of group, may display signs of weakness such as uncoordination. |
| 3 | Severe depression with signs of weakness such as a significantly altered gait. Obviously weak, difficulty in moving with group, raises head only when approached closely. |
| 4 | Moribund, unable to rise. |

Calves with visual clinical signs of BRD and a temperature of <103.6° F. (39.78° C.) were not treated. Animals not treated for BRD on initial evaluation that continued to display clear visual signs of BRD for 2 consecutive days were treated with an antimicrobial regardless of temperature. All calves that met the treatment criteria for BRD were treated with a single subcutaneous (SC) dose of 12.5 mg/kg enrofloxacin (Baytril, Bayer Animal Health, Shawnee Mission, Kans.). If the calf met the temperature criteria for a second time 72 hours post-initial treatment, the calf was treated with 40 mg/kg florfenicol SC (Nuflor, Intervet/Schering-Plough Animal Health, Boxmeer, Netherlands). If a calf met the treatment criteria for a third time 72 h post-secondary treatment, it received 22 mg/kg oxytetracycline (Biomycin 200, Boehringer Ingelheim Vetmedica, Inc., St Joseph, Mo.). After treatments, cattle were returned to their home pens.

In addition to BRD, other health outcomes that were considered included lameness, scrotal infection, and coccidiosis. A diagnosis of lameness was based on signs of limping and reduced weight bearing on one or more limbs during standing and walking. A diagnosis of scrotal infection was based on signs of anorexia, fever, and the presence of swelling and purulent discharge from the castration site. A diagnosis of coccidiosis was based on signs of diarrhea, anorexia, and depression and the presence of coccidia oocysts on microscopic examination of the feces. Calves with lameness and scrotal infections received 22 mg/kg oxytetracycline (Biomycin 200, Boehringer Ingelheim Vetmedica, Inc., St Joseph, Mo.) and calves with coccidiosis received 10 mg/kg amprolium (Corid 9.6% oral solution, Merial Ltd, Duluth, Ga.).

The removal of an animal from the study was permitted only for significant illness or injury that compromised the welfare of the animal. All calves that became severely injured or moribund were humanely euthanized. Animals that died or were euthanized during the study were transferred to the KSU Veterinary Diagnostic Laboratory for necropsy and disposal.

g. Data Collection and Management

All animals were individually weighed on arrival (day 0), prior to feeding at revaccination on day 14, and at the end of the study on day 28. Conditions were standardized for all animals at each time point. Feed consumption for each pen was determined on a daily basis by subtracting the weight of feed remaining at the next feeding from the total feed weight assigned to the pen. When animals were removed for health reasons, the amount of feed delivered to the pen and the corresponding animal gain in the pen were adjusted accordingly so that calculations for ADG, DMI and corresponding G:F were based on the number of calves remaining in the pen. Animal health data recorded for each calf identified as sick included the pull date, the individual animal identification number, body temperature, clinical score, a presumptive diagnosis, BW, and treatment. All data were recorded on data capture sheets that were subsequently compiled, collated in a computer spreadsheet program (Microsoft Office Excel 2007, Redmond, Wash.), and verified.

The ancillary production variables (ADG, days on feed [DOF], and daily DMI) were calculated for all animals that completed the feeding period. ADG and pen-level G:F were calculated using the following equations (Hannon et al., 2009):

$$\text{Live weight } ADG \text{ (kg)} = \frac{\text{Weight } (d28) - \text{Arrival weight } (d0)}{DOF}$$

$$DMI(\text{kg}) = \frac{\text{Daily pen feed allocation} - \text{Feed remaining at next feeding}}{\text{Number of calves in the pen}}$$

$$\text{Live weight } G{:}F = \frac{\text{Pen-level } ADG(\text{live weight})}{\text{Pen-level } DMI}$$

Animal health variables for pull rate, first and second re-pull rate, overall morbidity rate, morbidity rate attributable to specific disease syndromes (BRD, lameness, coccidiosis, and scrotal infection), first and second BRD relapse rate, study removal rate, and mortality rate between day 0 and day 28 were calculated using the following equations (Hannon et al., 2009):

$$\text{Pull rate } (\%) = \frac{\text{No. of calves pulled for treatment}}{\text{No. of calves on study}} \times 100\%$$

$$\text{First re-pull rate } (\%) = \frac{\text{No. of calves pulled a second time}}{\text{No. of calves pulled once}} \times 100\%$$

$$\text{Second re-pull rate } (\%) = \frac{\text{No. of calves pulled a third time}}{\text{No. of calves pulled a second time}} \times 100\%$$

$$\text{Overall morbidity rate } (\%) = \frac{\text{No. of calves treated for diease}}{\text{No. of calves on study}} \times 100\%$$

-continued $$BRD\ moridity\ rate\ (\%) = \frac{No.\ of\ calves\ with\ case\ definition\ for\ BRD}{No.\ of\ calves\ on\ study} \times 100\%$$

$$First\ BRD\ relapse\ rate\ (\%) = \frac{No.\ of\ first\ BRD\ relapses}{No.\ of\ calves\ treated\ for\ BRD} \times 100\%$$

$$Second\ BRD\ relapse\ rate\ (\%) = \frac{No.\ of\ second\ BRD\ relapses}{No.\ of\ first\ BRD\ relapses} \times 100\%$$

h. Statistics

In the absence of relevant preliminary data from studies testing a similar hypothesis to the present study, an estimate of the expected variance and magnitude of the effect of castration on health and performance of calves was made to determine an approximate sample size using previously published reports (Pinchak et al., 2004; Massey et al., 2011).

Health, performance, plasma meloxicam and behavioral data were analyzed using an analytical software program (SAS for Windows, Version 9.2, SAS Institute, Cary, N.C.). The GLIMMIX procedure of SAS (SAS Institute Inc., Version 9.2) was used for all computations. Pen served as the experimental unit for all outcomes. Least square mean estimates of the probability of outcome events (and the corresponding estimated standard errors) for each Sex-by-Trt combination was provided in the data scale. Pairwise comparisons were conducted to assess marginal effects or simple effects, depending on significance of the F-test statistic for main effects and interaction. Treatment means were partitioned using Tukey-Kramer or Bonferroni's method to adjust for multiple comparisons when the overall effect of sex (bull vs steer) or treatment (meloxicam vs. placebo) was significant (p<0.10). Statistical significance for multiple comparisons was designated a priori as ap-value≤0.05. Model assumptions were evaluated using externally studentized residuals and were considered to be appropriately met.

A general linear mixed model was fit to each performance response (DMI, ADG, G:F ratio) measured at the pen level. The linear predictor for the statistical model included the fixed effects of sex/gonadal status (bull vs. steer), treatment (meloxicam vs. placebo), time (day 14 and day 28), and all 2- and 3-way interactions. Random effects fit on the linear predictor included Lot as a blocking factor. Repeated observations within a pen were modeled using a compound symmetry residual variance-covariance structure. For DMI, the residual variance-covariance was expanded to accommodate heterogeneous variances at each time period. The Satterthwaite method was used to estimate degrees of freedom and Kenward Rogers was used for bias correction in standard error estimation. Newton-Raphson with ridging was the estimation algorithm implemented.

A generalized linear mixed model was fit to number of health events in a given pen using a binomial distribution whereby pen size defined the number of trials. Health outcomes included Pull, Morbidity and BRD. The linear predictor for the statistical model included the fixed effects of sex (bull vs. steer), treatment (meloxicam vs. placebo), and their 2-way interaction. Entry weight did not enhance model fit and thus, was excluded from the final model. The random effect of Lot was also fit in the linear predictor as a blocking factor to account for variability in health events between lots. Model parameters were estimated using Laplace integral approximation to maximum likelihood. Inference was conducted after checking for absence of overdispersion based on the Pearson chi-square/df fit statistic.

A generalized linear mixed model was fit to behavior scores recorded from 1 to 4 (1=calm, no movement; 2=restless shifting; 3=squirming, occasional shaking of the chute; 4=continuous vigorous movement and shaking of the chute, rearing, twisting, and struggling), assuming a categorical multinomial distribution of the response modeled with a cumulative logit link function. Behavioral outcomes were recorded at arrival, at castration and at revaccination 14 day after castration, and separate models were fit to each outcome. The linear predictor for the statistical model included the fixed effects of sex (bull vs. steer), treatment (meloxicam vs. placebo), and their 2-way interaction. The random effect of Lot was also fit in the linear predictor as a blocking factor. In addition, pen nested within gonadal status/sex and treatment was incorporated in the linear predictor to recognize pen as the experimental unit for these factors. Model parameters were estimated using Laplace integral approximation to maximum likelihood. Estimated cumulative probabilities for behavioral scores on each outcome were provided.

A general linear mixed model was also fit to the concentration of meloxicam measured 24 hours after drug administration in the meloxicam-treated animals. The linear predictor for the statistical model included the fixed effect of sex and the random blocking factor of Lot. Satterthwaite method was used to estimate degrees of freedom and Kenward Rogers was used for bias correction in standard error estimation. Estimation was conducted using the Newton-Raphson algorithm with ridging.

Kaplan-Meier plots for cumulative pull rate, crude morbidity, and BRD morbidity for bulls and steers were generated using GraphPad Prism Version 5.04 (GraphPad Software, La Jolla, Calif.). The endpoint of interest was survival time, which was defined as the time to first pull, first treatment, first treatment for BRD, or the end of the study in days. In the data set, the variable Group represented the treatment category (MEL or CONT), the variable Time represented the disease-free survival time, and the a variable Status was used as a censoring indicator, with the value 1 indicating an event time and the value 0 indicating a censored time. We identified GROUP as strata, and tested the null hypothesis that the 2 groups had equal survival curves using the log-rank (Mantel-Cox) test. If the p-value for the log-rank test was <0.05, this was evidence to reject the null hypothesis. The slope of the curve was used to compute a hazard ratio and its confidence interval using the Mantel Haenszel approach to compare the rate of an event occurring in the 2 treatments over time.

3. Results

After randomization, the mean (±EM) BW was 248.32±1.90 kg in the CONT-CAST group, 247.66±2.03 kg in the MEL-CAST group, 245.04±2.02 kg in the CONT-STR group, and 244.72±2.10 kg in the MEL-STR group, respectively. Ear notch samples were analyzed by antigen capture ELISA at the Kansas State University Veterinary Diagnostic Laboratory. All calves were confirmed negative for BVD virus. After day 28, 73 of 74 calves in the CONT-CAST group, 67 of 71 calves in the MEL-CAST group, 53 of 55 calves in the CONT-STR group, and 57 of 58 calves in the MEL-STR group completed the study. One calf in the CONT-STR group died from necrotizing diffuse phlebitis ofthe external iliac and femoral veins with associated thromboembolic pneumonia. Lameness accounted for removal of 1 calf from the CONT-CAST, CONT-STR, and MEL-STR groups, respectively, and 2 calves from the MEL-CAST group (Table 8). One calf was removed from the MEL-CAST group with chronic coccidiosis and another was removed with neurological symptoms.

TABLE 8

Study removal and mortality rate in calves receiving either lactose placebo (CONT; 1 mg/kg) or meloxicam (MEL; 1 mg/kg) suspended in water and administered per os, 24 h prior to processing.

| | Experimental group [no. (%)] | | | |
|---|---|---|---|---|
| | Bulls | | Steers | |
| | CONT-CAST | MEL-CAST | CONT-STR | MEL-STR |
| Number enrolled | 74 | 71 | 55 | 58 |
| Completed study | 73 | 67 | 53 | 57 |
| Study removal | 1 (1%) | 4 (6%) | 2 (4%) | 1 (2%) |
| Mortality rate | 0 | 0 | 1 (2%) | 0 |
| Reason for removal | | | | |
| Lameness | 1 (1%) | 2 (3%) | 1 (2%) | 1 (2%) |
| Chronic coccidiosis | 0 | 1 (1%) | 0 | 0 |
| Neurological symptoms | 0 | 1 (1%) | 0 | 0 |
| Pen death | 0 | 0 | 1 (2%) | 0 | a. Performance

Overall pen-level ADG in steers was greater than in the castrated calves ($p<0.001$) (Table 9). There was no evidence of an effect of meloxicam administration ($p=0.972$) on ADG. However, ADG tended to increase with days on feed ($p=0.076$). There was also a sex-by-treatment interaction on pen-level ADG over the feeding period. CAST calves had a 0.65±0.17 kg/d increase in ADG from d 15-d 28 compared to d1-d14 ($p=0.0011$). In contrast, STR calves had a 0.20±0.17 kg/d decrease in ADG over the corresponding period ($p=0.26$). Furthermore, STR calves had a 0.74±0.14 kg/d greater ADG between d1 and d14 ($p<0.001$) compared with CAST calves but CAST calves had a 0.11±0.14 kg/d greater ADG between d15 and d28 ($p=0.45$).

Pen-level DMI in the placebo and meloxicam-treated steers was greater than in the castrated calves ($p=0.016$) (Table 9). There was no evidence of an effect of meloxicam administration ($p=0.73$) on DMI. However, DMI was greater at d 28 compared with d 14 in both CAST and STR calves ($p<0.001$) irrespective of treatment.

Pen-level G:F in the steers was greater than in the castrated calves ($p<0.001$) (Table 9). There was no evidence of an effect of meloxicam administration ($p=0.73$) on G:F. However, there was a sex-by-treatment interaction on pen-level G:F between feeding periods. CAST calves had a 0.04±0.03 increase in G:F from d 15-d 28 compared to d1-d14 ($p=0.16$). In contrast, STR calves had a 0.12±0.03 kg/d decrease in G:F over the corresponding period ($p=0.0004$). Furthermore, STR calves had a 0.13±0.02 greater G:F between d1 and d14 ($p<0.001$) compared with CAST calves but CAST calves had a 0.02±0.02 greater G:F between d15 and d28 ($p=0.31$).

TABLE 9

Pen-level mean estimates (and estimated standard errors) for average daily gain (ADG), daily dry matter intake (DMI) and gain-to-feed ratio (G:F) during 28 days on feed in bulls and steers receiving either lactose placebo (1 mg/kg) or meloxicam (1 mg/kg) suspended in water and administered per os, 24 h prior to processing.

| | Sex | | | | | | | | P-values | | | | | |
|---|---|---|---|---|---|---|---|---|---|---|---|---|---|---|
| | Bulls | | | | Steers | | | | | | | | | |
| | Treatment | | | | | | | | | | | | | |
| | Placebo | | Meloxicam | | Placebo | | Meloxicam | | | | | | | |
| | Days on Feed | | | | | | | | | | | Sex * | Trt * | Sex * |
| | d1-14 | d15-28 | d1-14 | d15-28 | d1-14 | d15-28 | d1-14 | d15-28 | Sex | Trt | DOF | Sex * Trt | DOF | DOF | Trt * DOF |
| ADG (kg) | 0.78 (0.18) | 1.54 (0.18) | 0.95 (0.18) | 1.50 (0.18) | 1.72 (0.18) | 1.37 (0.18) | 1.51 (0.18) | 1.46 (0.18) | <.001 | 0.972 | 0.076 | 0.302 | 0.002 | 0.845 | 0.313 |
| DMI (kg) | 4.70 (0.22) | 6.95 (0.31) | 4.80 (0.22) | 7.01 (0.31) | 5.26 (0.22) | 7.39 (0.31) | 5.06 (0.22) | 7.23 (0.31) | 0.016 | 0.733 | <.001 | 0.352 | 0.726 | 0.981 | 0.849 |
| G:F | 0.16 (0.03) | 0.22 (0.03) | 0.19 (0.03) | 0.21 (0.03) | 0.32 (0.03) | 0.19 (0.03) | 0.30 (0.03) | 0.20 (0.03) | <.001 | 0.727 | 0.065 | 0.335 | <.001 | 0.949 | 0.326 | b. Health

Figure 8A:
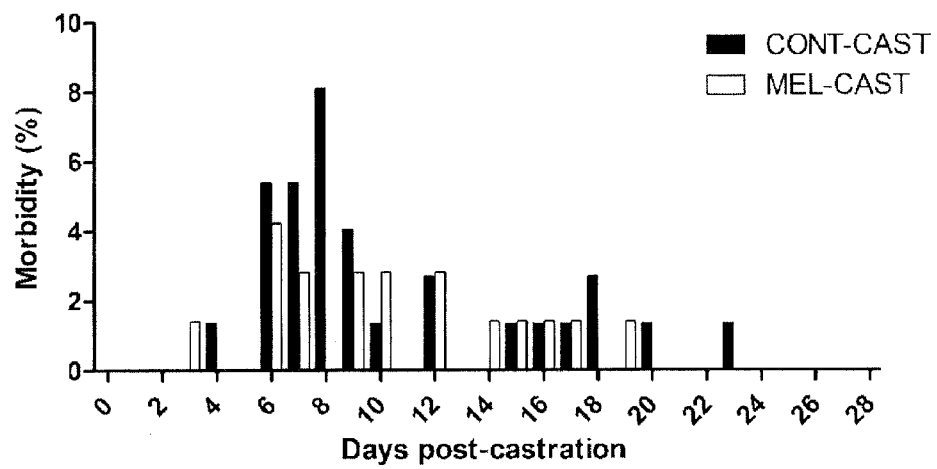
FIG. 8(a) is a graph of the morbidity distribution pattern in bulls administered lactose placebo (CONT) or meloxicam (MEL) 24 h prior to castration (CAST) in Example 4.
Figure 8B:
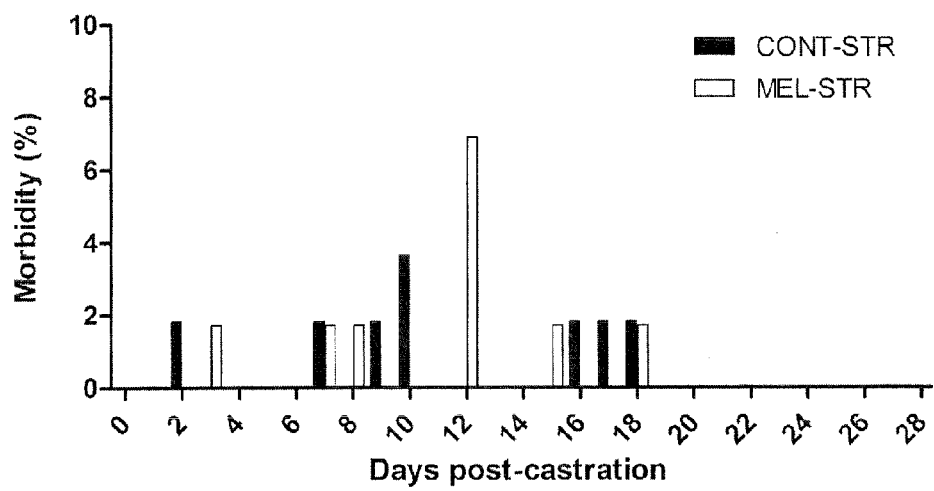
FIG. 8(b) is a graph of the morbidity distribution pattern in steers (STR) administered lactose placebo (CONT) or meloxicam (MEL) 24 h prior to processing without castration in Example 4.

The pen-adjusted first pull rate was greater in the CONT-CAST (45.19%) compared with the MEL-CAST (25.83%) calves ($p=0.038$) (Table 10). Pull rate in steers was similar between the two treatment groups ($p=0.78$). However, pull rate was higher in the CONT-CAST calves compared with the CONT-STR calves ($p=0.007$) but similar between the MEL-CAST and MEL-STR calves ($p=0.43$). Overall morbidity peaked at 8% on day 8 in the CONT-CAST group and at 4% on day 6 in the MEL-CAST group (FIG. 8($a$)). Overall morbidity rate peaked at 4% on day 10 in the CONT-STR group and at 7% on day 12 in the MEL-STR group (FIG. 8($b$)).

Overall morbidity rate tended to be greater in bull calves than steer calves ($p=0.08$), but the overall morbidity between treatment groups was similar ($p=0.28$). There was no difference in morbidity between CONT-CAST and MEL-CAST calves ($p=0.13$) or CONT-STR and MEL-STR calves ($P=0.87$). However, morbidity was greater in the CONT-CAST calves compared with the CONT-STR calves ($p=0.004$), but similar between the MEL-CAST and MEL-STR calves ($p=0.57$).

The incidence of BRD tended to be greater in bull calves than steer calves ($p=0.06$), but the overall morbidity attributable to BRD between treatment groups was similar ($p=0.31$).

The incidence of BRD was greater in CONT-CAST compared with MEL-CAST calves (p=0.003) but similar between CONT-STR and MEL-STR calves (p=0.67). Morbidity was greater in the CONT-CAST compared with CONT-STR calves (p=0.0006) but similar between the MEL-CAST and MEL-STR calves (p=0.68).

Figure 9A:
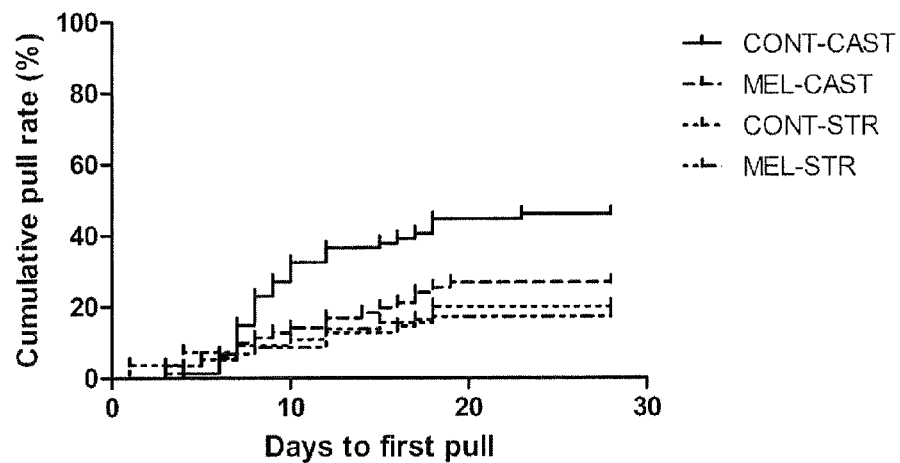
FIG. 9(a) shows a Kaplan-Meier survival curve depicting cumulative pull rate in calves administered lactose placebo (CONT) or meloxicam (MEL) 24 h prior to castration in Example 4.
Figure 9B:
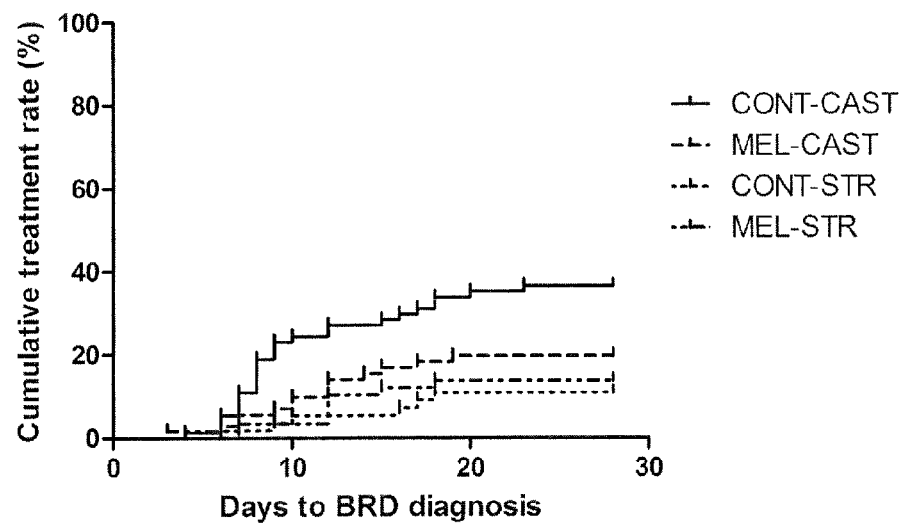
FIG. 9(b) shows a Kaplan-Meier survival curve depicting cumulative BRD treatment rate in calves administered lactose placebo (CONT) or meloxicam (MEL) 24 h prior to castration in Example 4.

The first re-pull rate was no different between bulls and steers (p=0.14) or between treatment groups (p=0.99). First BRD retreatment rate was also similar between sex (p=0.60) and treatment (p=0.70) (Table 11). There was also no difference between bulls and steers (p=0.66) or treatment groups (p=0.64) for calves pulled a third time. Similarly the third BRD treatment rate was similar between bulls and steers (p=0.37) and treatment groups (p=0.94).

curves for first pull rate, overall morbidity rate, and BRD morbidity rate (p=0.004) (FIGS. 9(a)-(b); Table 12). First pull rate was significantly greater in CONT-CAST calves than MEL-CAST calves (p=0.016) and CONT-STR calves (p=0.0029). BRD morbidity rate was significantly greater in CONT-CAST calves than MEL-CAST calves (p=0.0230) and CONT-STR calves (p=0.0009). Furthermore, survival curve comparisons for first pull rate and BRD morbidity rate indicated a significant hazard ratio between MEL-CAST and CONT-CAST calves (p=0.016) and CONT-CAST and CONT-STR calves (p=0.003). Other survival curve comparisons for first pull rate and. BRD morbidity rate did not differ. A hazard ratio tended (p=0.073) to occur for overall morbidity rate between MEL-CAST and CONT-CAST groups and a hazard ratio occurred between

TABLE 10

Estimated probabilities of health events (and estimated standard errors) adjusted for pen.

| | Experimental group Sex | | | | P-values | | |
| --- | --- | --- | --- | --- | --- | --- | --- |
| | Bulls | | Steers | | | | |
| | Treatment | | | | | | |
| | Placebo | Meloxicam | Placebo | Meloxicam | Sex | Trt | Sex * Trt |
| Population at risk | 74 | 71 | 55 | 58 | | | |
| Pulls (%) | 45.2[a,x] (11.1) | 25.8[y] (9.0) | 19.7[b] (6.0) | 17.1 (8.7) | 0.01 | 0.06 | 0.45 |
| Overall morbidity (%) | 35.0[a] (16.5) | 21.1 (12.1) | 13.3[b] (8.6) | 14.4 (10.8) | 0.07 | 0.28 | 0.36 |
| BRD morbidity (%) | 33.8[a,x] (15.4) | 17.2[y] (10.7) | 9.7[b] (5.8) | 12.6 (10.2) | 0.06 | 0.31 | 0.21 |

[a,b]Indicate differences between bulls and steer treated with placebo (p < 0.05). No evidence for differences was apparent amongst calves treated with meloxicam.
[x,y]Indicate differences in bulls treated with placebo vs. meloxicam (p < 0.05). No evidence for differences between placebo and meloxicam was apparent in steers.
Trt = Treatment group (meloxicam or placebo)

TABLE 11

Estimated probabilities of re-treatment health events (and estimated standard errors) adjusted for pen in bulls and steers

| | Experimental group Sex | | | | P-values | | |
| --- | --- | --- | --- | --- | --- | --- | --- |
| | Bulls | | Steers | | | | |
| | Treatment | | | | | | |
| | Placebo | Meloxicam | Placebo | Meloxicam | Sex | Trt | Sex * Trt |
| First re-pull rate (%) | 43.7 (14) | 52.6 (8) | 27.1 (16) | 69.9 (21) | 0.14 | 0.99 | 0.31 |
| First BRD relapse rate (%) | 33.3 (12) | 35.7 (14) | 33.3 (22) | 50.0 (20) | 0.60 | 0.70 | 0.70 |

Log-rank (Mantel-Cox) tests indicated that placebo-treated and meloxicam-treated calves had dissimilar survival CONT-CAST and CONT-STR groups (p=0.003). Other survival curve comparisons did not differ (p>0.05).

TABLE 12

Log-rank (Mantel-Cox) and Mantel Haenszel hazard ratio comparison between cumulative incidence of first pull, overall morbidity, and BRD morbidity.

| | Log-rank | | | | 95% CI | | |
| --- | --- | --- | --- | --- | --- | --- | --- |
| | chi square | P-value | Survival curve comparison | Hazard ratio | LOWER (HR) | UPPER (HR) | P-value |
| First pull rate | 16.73 | 0.0008 | CONT-CAST vs. MEL-CAST | 1.97 | 1.14 | 3.42 | 0.016 |
| | | | MEL-STR vs. CONT-STR | 1.18 | 0.50 | 2.79 | 0.71 |

TABLE 12-continued

Log-rank (Mantel-Cox) and Mantel Haenszel hazard ratio comparison between cumulative incidence of first pull, overall morbidity, and BRD morbidity.

| | Log-rank | | | | 95% CI | | |
| --- | --- | --- | --- | --- | --- | --- | --- |
| | chi square | P-value | Survival curve comparison | Hazard ratio | LOWER (HR) | UPPER (HR) | P-value |
| | | | MEL-CAST vs. MEL-STR | 1.59 | 0.76 | 3.32 | 0.244 |
| | | | CONT-CAST vs. CONT-STR | 2.48 | 1.37 | 4.51 | 0.0029 |
| Overall morbidity rate | 13.26 | 0.0041 | CONT-CAST vs. MEL-CAST | 1.73 | 0.95 | 3.16 | 0.073 |
| | | | MEL-STR vs. CONT-STR | 0.83 | 0.31 | 2.22 | 0.71 |
| | | | MEL-CAST vs. MEL-STR | 1.58 | 0.72 | 3.43 | 0.25 |
| | | | CONT-CAST vs. CONT-STR | 2.86 | 1.44 | 5.68 | 0.003 |
| BRD morbidity rate | 16.89 | 0.0007 | CONT-CAST vs. MEL-CAST | 2.06 | 1.11 | 3.82 | 0.023 |
| | | | MEL-STR vs. CONT-STR | 0.78 | 0.27 | 2.23 | 0.64 |
| | | | MEL-CAST vs. MEL-STR | 1.49 | 0.64 | 3.47 | 0.36 |
| | | | CONT-CAST vs. CONT-STR | 3.23 | 1.62 | 6.45 | 0.0009 | c. Behavior

Figure 10:
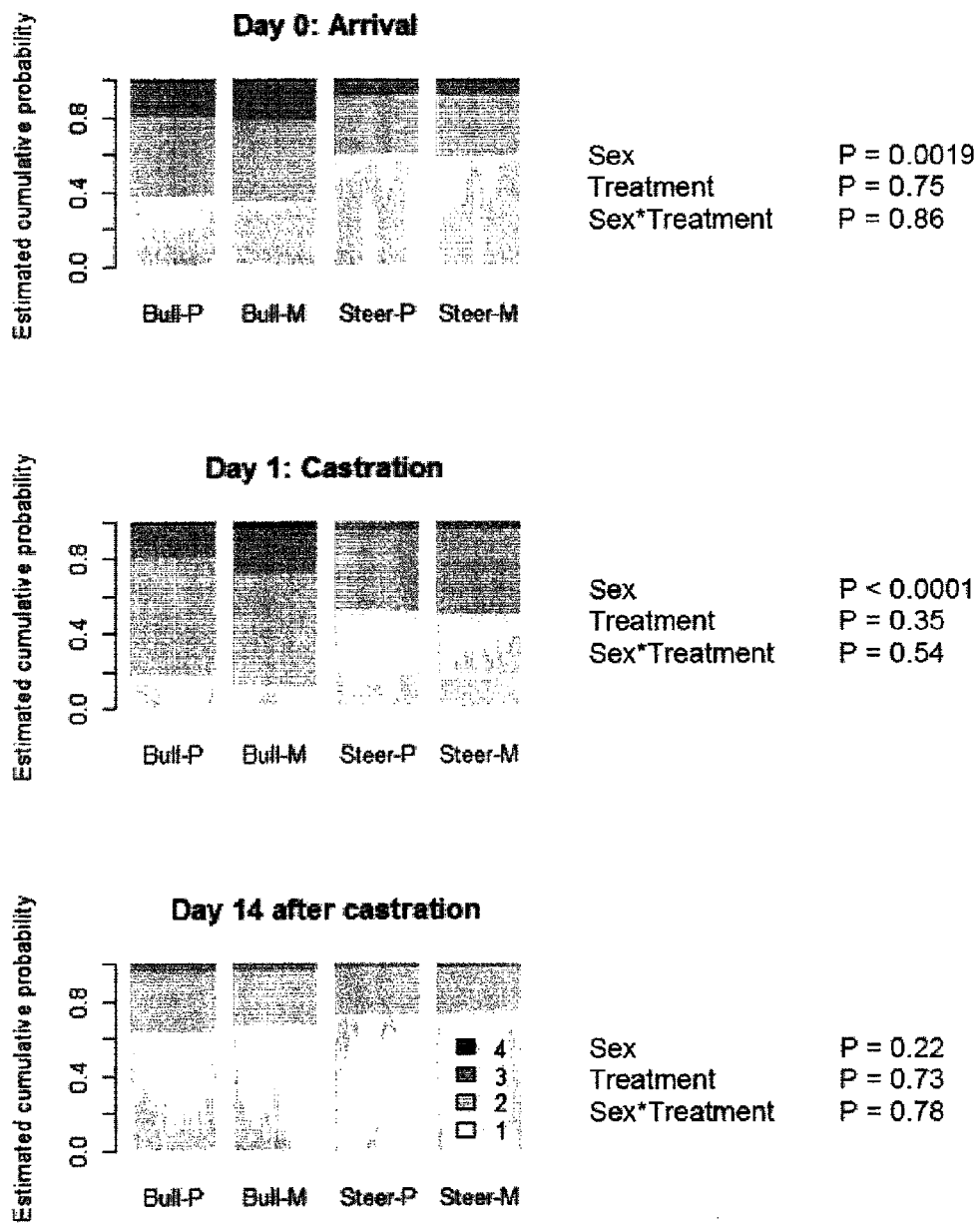
FIG. 10 depicts the estimated cumulative probabilities of temperament scores in bulls and steers at arrival (day 0), castration (day 1) and 14 d after castration.

On day 0, a greater percentage of steer calves received a temperament score of 1 compared with the bull calves (p=0.0019) at the time of dosing with meloxicam (FIG. 10). Temperament scores are: 1=calm, no movement; 2=restless shifting; 3=squirming, occasional shaking of the chute; 4=continuous vigorous movement and shaking of the chute, rearing, twisting, and struggling. There was no difference between treatment groups (p=0.75) or evidence of a sex-by-treatment interaction (p=0.86). Similarly at castration (d 1) there were more escape behaviors recorded in the bull calves compared with the steers (p<0.001) but no difference between treatment groups (p=0.34). There was no difference in temperament scores between sex (p=0.22) or treatment (p=0.73) at revaccination on day 14.

d. Meloxicam Concentrations

Figure 11:
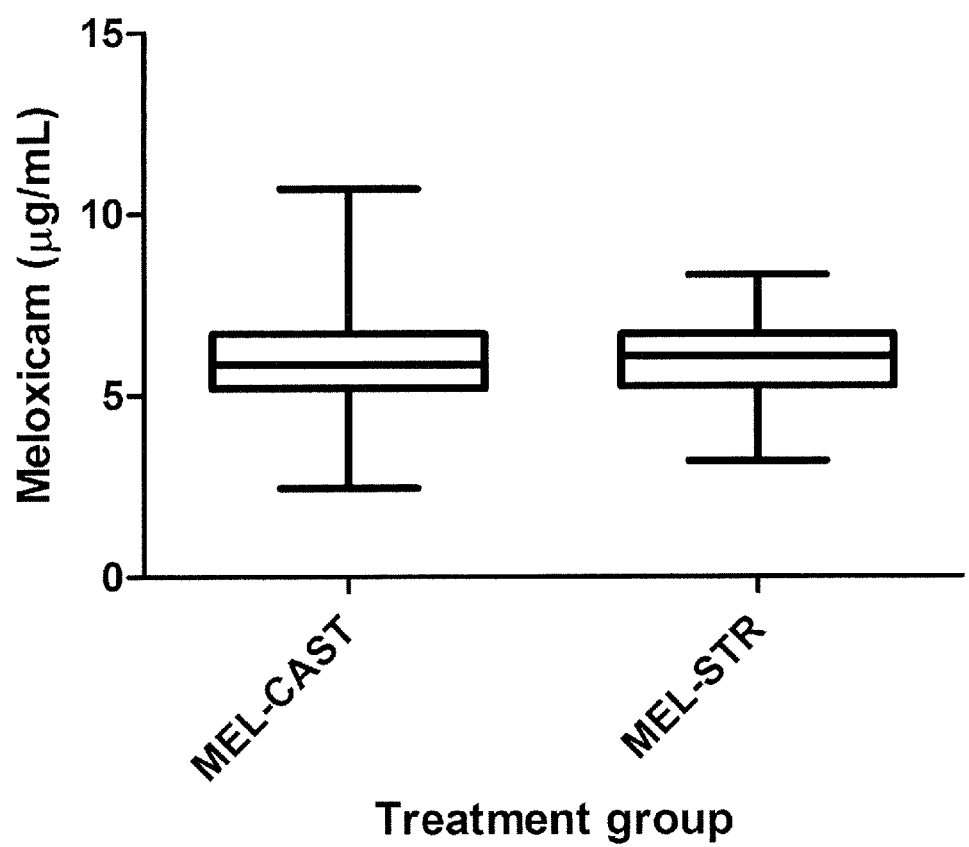
FIG. 11 is a box and whisker graph showing the median, 25th, and 75th percentile and range of plasma meloxicam concentrations at the time of castration in calves administered 1 mg/kg meloxicam, 24 h prior to castration (CAST) or simulated castration (STR) in Example 4.

The administered dose of meloxicam rounded down to the nearest whole tablet ranged from 0.89 to 1.00 mg/kg. Sorting and drug administration commenced at around 0800 h and was concluded by 1030 h and therefore lasted approximately 2 min. per calf. The mean (±SEM) plasma meloxicam concentration at the time of castration, approximately 24 h after treatment, was 6.01±0.07 μg/mL in bulls and 5.97±0.07 μg/mL in steers (p=0.70) (FIG. 11). No outward adverse events associated with NSAID administration (i.e. gastrointestinal bleeding, clotting deficits, or anorexia) were noted after PO administration of meloxicam.

In the present study, calves in the CONT-CAST group were at a greater risk of being identified as requiring treatment compared with CONT-STR calves. However, bull calves receiving meloxicam prior to castration were about 50% less likely to develop BRD as compared to placebo-treated castrated bulls. In addition, 59% of castrated calves were treated at least once compared with 33% of steers in this study. Of calves castrated on arrival, 23% were retreated. However, there was no evidence of a difference in steers treated with meloxicam, as compared with the untreated control steers. That is, meloxicam did not appear to decrease the incidence of BRD in the steers. These results indicate that oral meloxicam has an effect on the incidence of BRD in bull calves when castrated upon arrival at a feedlot. These results have implications for increasing the health and well-being of calves after castration. These findings also suggest that meloxicam administration prior to castration in post-weaning calves may reduce the number of animals identified as requiring treatment by feedlot personnel and the overall cumulative BRD morbidity rate. This may decrease the amount of antimicrobials needed to treat pneumonia in calves after castration and lessen the economic impact of BRD in livestock production systems.

Example 5

Pharmacokinetics of Oral Gabapentin Alone or Co-Administered with Meloxicam in Ruminant Beef Calves 1. Introduction The purpose of this study was to investigate the pharmacokinetics and oral bioavailability of gabapentin alone or co-administered with meloxicam in ruminant calves. If oral administration of gabapentin and meloxicam results in plasma concentrations at sufficient therapeutic levels, this may support clinical studies leading to the development of efficacious drug regimens to mitigate chronic pain associated with lameness in cattle and other ruminants.

2. Materials and Methods a. Study cattle

Six crossbred, castrated male beef calves were used in this experiment. The study was conducted in two phases separated by a 3-week washout period. Calves were acquired from a livestock commission company in Kansas and were 6-8 months old and weighed between 240 and 400 kg. On arrival at our facility, the calves received a single SC dose of a 7-way clostridial vaccine (Fortress 7, Pfizer), a modified-live vaccine IM against viral respiratory disease (Bovi-shield Gold 5, Pfizer), and a single injection of florfenicol (Nuflor, Intervet-Schering Plough) SC at 40 mg/kg. The protocol for this study was approved by the Institutional Animal Care and Use Committee at Kansas State University (Protocol No. 2472).

b. Housing and husbandry

Study animals were acclimated in group housing comprising 6 calves/pen for about 3 weeks prior to commencement of the study. The housing consisted of an outdoor concrete pad (9.75 m x 18.29 m) with a partial roof and straw bedding. Cattle were fed a typical receiving diet composed of cracked corn, oats, soybean meal, molasses, and a protein/vitamin/mineral supplement at 8 kg/head/day throughout the experiment. Prairie grass hay and water were offered ad libitum.

c. Drug administration

In the first study, whole gabapentin capsules were administered by stomach tube at 10 mg/kg (Gabapentin capsules, USP 100 mg and 400 mg; NDC 0228-2667; Actavis Elizabeth LLC; Lot #832J91) after which the tube was flushed with 1 L of water. In the second study, the contents of gabapentin capsules were co-administered with meloxicam tablets (15 mg; NDC 65862-098-01; Aurobindo Pharma; Lot # MX1509019-A) at 15 mg/kg and 0.5 mg/kg respectively. The oral dose was rounded to the nearest whole capsule or tablet. In the second study, the contents of the capsules and whole tablets were mixed with 50 mL of water to make a suspension that was administered within 5 minutes of mixing. The stomach tube was then flushed with 1 L of water prior to removal.

d. Collection of Blood Samples

In both studies, calves were restrained with a rope halter for blood collection. In the first study, blood samples for gabapentin determination were collected prior to drug administration (0h) and at 0.25, 0.5, 1, 2, 3, 4, 6, 8, 10, 12, and 24 h after administration. In the second study, blood samples for gabapentin and meloxicam determination were collected at 0, 1, 2, 3, 4, 5, 6, 8, 10, 12, 18, 24, 30, 36, and 48 h after administration. Blood was drawn via a jugular catheter into a collection syringe and immediately transferred to 6 mL evacuated tubes containing lithium heparin (Vacutainer, BD Diagnostics), then stored on ice for up to 30 min. before processing. Blood samples were centrifuged for 10 min. at 1,500 g. Plasma was then harvested, placed in cryovials, and frozen at −70° C. until analysis. All samples were analyzed within 60 days after sample collection.

e. Plasma Gabapentin and Meloxicam Analysis

Plasma concentrations of gabapentin and meloxicam were determined with HPLC (Shimadzu Prominence, Shimadzu Scientific Instruments) and mass spectrometry (API 2000, Applied Biosystems). Plasma samples or standards (100 μL) were added to 100 μL of internal standard (pregabalin 5 μg/mL in methanol) and 400 μL of methanol with 0.1% formic acid to precipitate the proteins. Quantitation was performed by calculating the ratios of gabapentin m/z 172.1→154.1 and meloxicam m/z 352.09→114.90 responses relative to the internal standard m/z 160.00→142.00 transition. The samples were vortexed for 5 seconds and centrifuged for 10 min. at 15,000 g. Supernatant (200 μL) was transferred to an injection vial with an injection volume of 25 μL. The mobile phase consisted of 100% B from 0 to 1 min. with a linear gradient of 50% B at 3 min., which was maintained until 6 min., followed by a linear gradient of 100% B at 6.5 min., with a total run time of 8 min. The solvent 'A' was acetonitrile and the solvent 'B' was 0.1% formic acid at a flow rate of 0.5 mL/min. Separation was achieved with a phenyl column (Hypersil Gold, 150×2.1, 5 μM, Thermo Scientific) maintained at 40° C.

The standard curve was linear from 0.05-10 μg/mL for gabapentin and 0.025-2.5 μg/mL for meloxicam and was accepted if the correlation coefficient exceeded 0.99 and predicted values were within 15% of actual values. The accuracy of the gabapentin assay was 97±10% and the coefficient of variation was 10% determined on replicates of 3 at 0.05, 0.1, 0.5, 5, and 10 μg/mL. The accuracy of the meloxicam assay was 100±9% and the coefficient of variation was 6% determined on replicates of 3 at 0.025, 0.05, 0.25, 1.0, and 2.5 μg/mL. The limits of detection was 0.05 and 0.025 μg/mL for gabapentin and meloxicam, respectively (defined as the lowest concentration on the standard curve with predicted concentrations within 15% of actual concentrations).

f. Pharmacokinetics Analysis

Pharmacokinetic analyses were performed with computer software (WinNonlin 5.2, Pharsight Corp). The variables calculated included the area under the curve from time 0 to infinity (AUC) using the linear trapezoidal rule, area under the first moment curve from time 0 to infinity (AUMC), plasma clearance per fraction of the dose absorbed (Cl/F), apparent volume of distribution (area method) per fraction of the doze absorbed (Vz/F), first-order rate constant (λz), terminal half-life ($t_{1/2}$), and mean residence time extrapolated to infinity (MRT). The maximum serum concentration (Cmax) and time to maximum serum concentration (Tmax) were determined directly from the data.

3. Results

Figure 12:
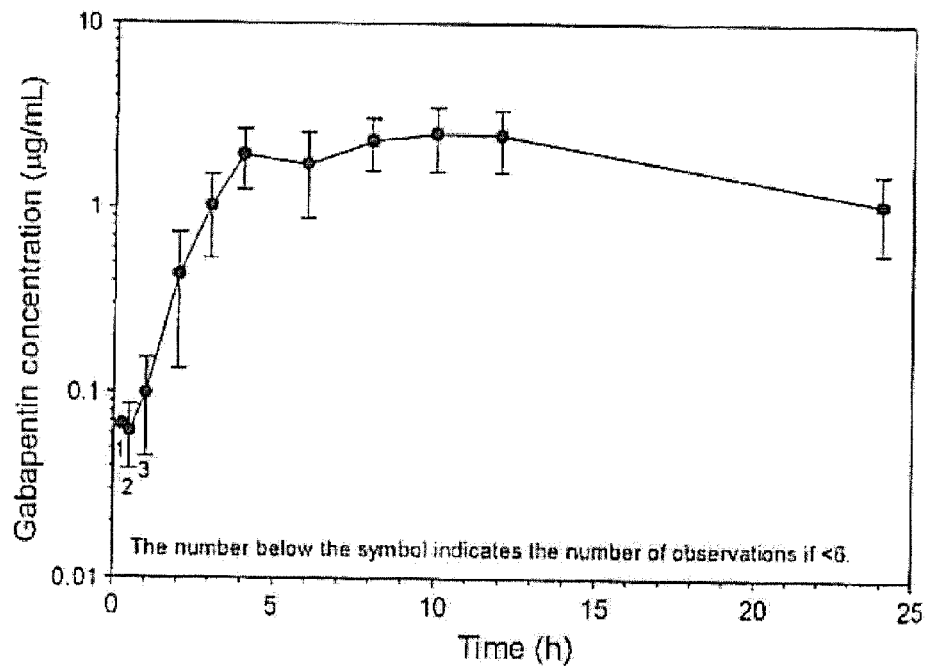
FIG. 12 is a graph of the mean (+SD) plasma concentration of gabapentin following single 10 mg/kg PO administration to calves from Example 5. The numbers in parenthesis are the number of observations above the limit of quantitation (LOQ) of the assay if the number of observations was less than 6.
Figure 13:
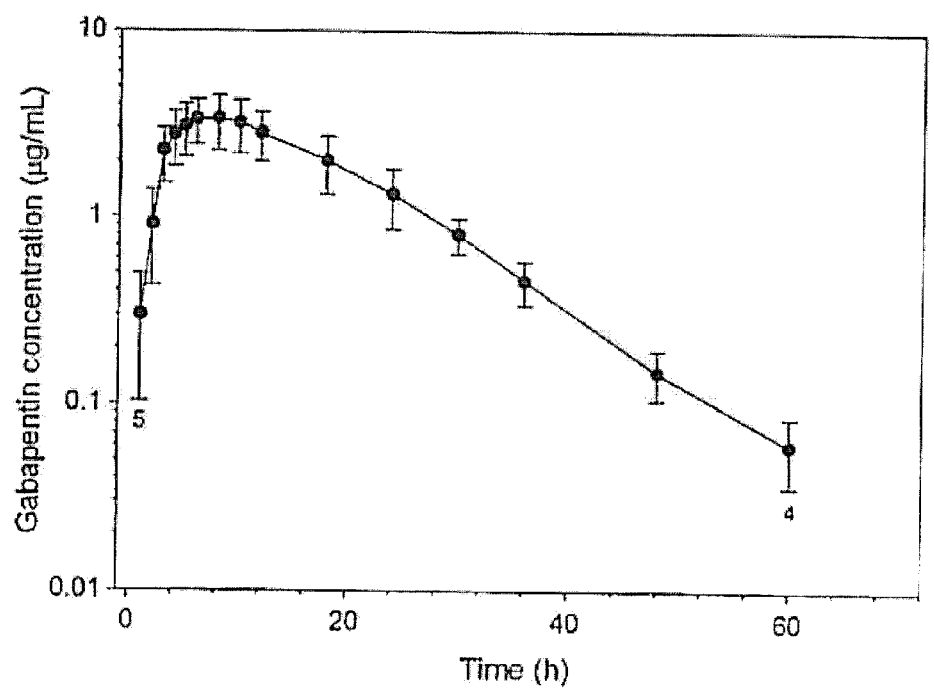
FIG. 13 is a graph of the mean (±SD) plasma concentrations of gabapentin following single 15 mg/kg PO administration with 0.5 mg/kg meloxicam in calves from Example 5. The numbers in parenthesis are the number of observations above the limit of quantitation (LOQ) of the assay if the number of observations was less than 6.

No adverse effects were noted after oral administration of gabapentin or co-administration of gabapentin and meloxicam. The average dose of gabapentin administered was 10.1 mg/kg body weight (range, 9.8-10.3 mg/kg) and 15.00 mg/kg (14.85-15.11 mg/kg) in the first and second study, respectively. FIGS. 12 and 13 show the mean (±SD) plasma concentration vs. time profile of gabapentin following 10 mg/kg and 15 mg/kg PO administration in calves, respectively. The mean pharmacokinetic parameters for gabapentin administered at 10 and 15 mg/kg are also summarized in Tables 13 and 14.

TABLE 13

Pharmacokinetic parameters of gabapentin after oral administration of whole capsules at 10 mg/kg with meloxicam at 0.5 mg/kg.

|  |  | Mean | SD | Min | Median | Max |
|---|---|---|---|---|---|---|
| Dose | mg/kg | 10.1 | 0.2 | 9.8 | 10.1 | 10.3 |
| AUC extrapolated | % | 27.78 | 11.11 | 16.8 | 24.4 | 46.2 |
| AUC | h * μg/mL | 59.73 | 23.45 | 22.5 | 61.9 | 87.1 |
| AUMC | h * h * μg/mL | 1273.15 | 797.84 | 341.9 | 1102.1 | 2565.9 |
| Cl/F | mL/min/kg | 3.42 | 2.01 | 1.9 | 2.8 | 7.3 |
| Cmax | μg/mL | 2.97 | 0.40 | 2.5 | 2.9 | 3.7 |
| T½ λz | h | 11.02 | 3.68 | 7.9 | 9.2 | 17.7 |
| λz | 1/h | 0.08 | 0.04 | 0.0 | 0.1 | 0.1 |
| MRT | h | 19.82 | 5.51 | 15.1 | 18.1 | 29.4 |
| Tmax | h | 9.33 | 2.73 | 4.0 | 10.0 | 12.0 |
| Vz/F | L/kg | 3.03 | 1.40 | 1.9 | 2.6 | 5.8 |

TABLE 14

Pharmacokinetic parameters of gabapentin after oral administration of gabapentin powder at 15 mg/kg with meloxicam at 0.5 mg/kg.

|  |  | Mean | SD | Min | Median | Max |
|---|---|---|---|---|---|---|
| Dose | mg/kg | 15.00 | 0.09 | 14.9 | 15.01 | 15.11 |
| AUC extrapolated | % | 1.63 | 1.46 | 0.6 | 1.1 | 4.4 |
| AUC | h * μg/mL | 70.29 | 19.31 | 37.05 | 71.03 | 95.26 |

TABLE 14-continued

Pharmacokinetic parameters of gabapentin after oral administration of gabapentin powder at 15 mg/kg with meloxicam at 0.5 mg/kg.

| | | Mean | SD | Min | Median | Max |
|---|---|---|---|---|---|---|
| AUMC | h * h * µg/mL | 1170.45 | 279.90 | 813.8 | 1127.2 | 1645.4 |
| Cl/F | mL/min/kg | 3.88 | 1.46 | 2.62 | 3.52 | 6.75 |
| Cmax | µg/mL | 3.57 | 1.04 | 1.7 | 3.7 | 4.6 |
| T½ λz | h | 8.12 | 2.11 | 6.9 | 7.4 | 12.4 |
| λz | 1/h | 0.09 | 0.02 | 0.056 | 0.094 | 0.101 |
| MRT | h | 17.05 | 2.55 | 14.9 | 16.2 | 22.0 |
| Tmax | h | 7.33 | 1.63 | 6.0 | 7.0 | 10.0 |
| Vz/F | L/kg | 2.93 | 2.11 | 1.68 | 2.13 | 7.22 |

The mean (±SD) Cmax, Tmax, and elimination half-life ($T_{1/2}\lambda_z$) for gabapentin (10 mg/kg) alone were 2.97 0.40 µg/mlL, 9.33±2.73 h, and 11.02±3.68 h, respectively. The mean (±SD) Cmax, Tmax, and elimination half-life ($T_{1/2}\lambda_z$) for gabapentin (15 mg/kg) co-administered with meloxicam were 3.57 1.04 µg/mL, 7.33±1.63 h, and 8.12±2.11 h, respectively.

The average dose of meloxicam administered was 0.51 mg/kg body weight (range, 0.49-0.52 mg/kg). The mean pharmacokinetic parameters for meloxicam are presented in Table 15.

TABLE 15

Pharmacokinetic parameters of meloxicam after oral administration of whole tablets at 0.5 mg/kg with gabapentin at 15 mg/kg.

| Parameter | Units | Mean | SD | Minimum | Median | Maximum |
|---|---|---|---|---|---|---|
| Dose | mg/kg | 0.51 | 0.01 | 0.49 | 0.50 | 0.52 |
| AUC extrapolated | % | 16.75 | 11.62 | 2.5 | 12.7 | 32.3 |
| AUC | hr * µg/mL | 90.45 | 20.08 | 69.9 | 84.4 | 119.3 |
| AUMC | hr * hr * µg/mL | 3530.82 | 1905.94 | 1702.0 | 2661.9 | 6004.1 |
| Cl/F | mL/min/kg | 0.1 | 0.02 | 0.070 | 0.099 | 0.119 |
| Cmax | µg/mL | 2.12 | 0.19 | 1.9 | 2.0 | 2.4 |
| T½ λz | hr | 20.47 | 9.22 | 8.4 | 17.6 | 33.2 |
| λz | 1/hr | 0.04 | 0.02 | 0.0209 | 0.0394 | 0.0823 |
| MRT | hr | 36.92 | 12.02 | 24.3 | 31.7 | 54.5 |
| Tmax | hr | 11.67 | 3.44 | 8.0 | 11.0 | 18.0 |
| Vz/F | L/kg | 0.16 | 0.04 | 0.087 | 0.156 | 0.218 |

Figure 14:
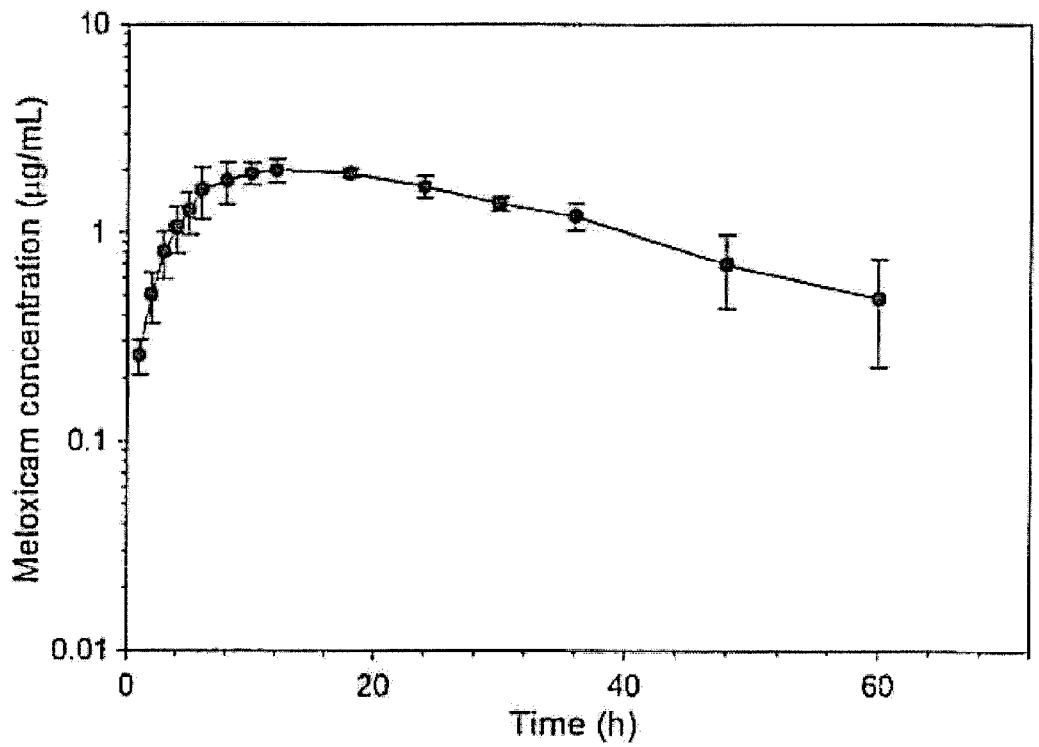
FIG. 14 is a graph of the mean (+SD) plasma concentrations of meloxicam following single 0.5 mg/kg PO administration with 15 mg/kg gabapentin in calves in Example 5.

FIG. 14 shows the mean (±SD) plasma concentration vs. time profile of meloxicam following a single 0.5 mg/kg PO administration in calves. A mean peak plasma concentration of 2.10 µg/mL (range 1.9-2.4 µg/mL) was recorded at 11.67 h (range 8-18 h), with an elimination half-life ($T_{1/2}\lambda z$) of 20.45 h (range, 8.40-33.20 h).

The results of the present study show that plasma concentrations of gabapentin in calves were maintained above 2 µg/mL, the reported minium effective concentration in humans, for up to 15 hours. Further, plasma meloxicam concentrations were maintained in calves above the effective concentration of 0.2 µg/mL reported in horses for up to 48 hours. The plasma elimination half-life of gabapentin in the present study (11.02±3.68 h) in calves was considerably longer than previously reported in other species.

Example 6

Effect of Oral Meloxicam and Gabapentin on Bovine Lameness

Introduction

This study examined the pharmacokinetics and analgesic effect of oral meloxicam administered alone or in combination with gabapentin using an experimental bovine lameness model.

2. Materials and Methods a. Experimental Animals

Eighteen male British×Continental beef calves aged 4-6 months and weighing 297-392 kg were used for this study. On arrival at our facility, the calves received a single SC dose of a 7-way clostridial vaccine (Fortress 7, Pfizer), a modified-live vaccine IM against viral respiratory disease (Bovi-shield Gold 5, Pfizer), and a single injection of florfenicol (Nuflor, Intervet-Schering Plough) SC at 40 mg/kg.

b. Housing and Husbandry

Study animals were acclimated in group housing comprising 6 calves/pen for about 12 weeks prior to commencement of the study. The housing consisted of an outdoor concrete pad (9.75 m×18.29 m) with a partial roof and straw bedding. Cattle were fed a typical receiving diet composed of cracked corn, oats, soybean meal, molasses, and a protein/vitamin/mineral supplement at 8 kg/head/day throughout the experiment. Prairie grass hay and water were offered ad libitum.

c. Jugular Catheterization

Approximately 24 hours prior to study commencement, all calves were individually restrained in a squeeze chute using a rope halter and the attached head gate. Following restraint, the area over the right jugular vein was clipped and disinfected using povidone iodine and 70% isopropyl alcohol swabs. The catheter site was infiltrated with approximately 0.5 ml of 2% lidocaine injection (Hospira Inc, Lake Forest, Ill.) and a small skin incision with a #22 blade was made to facilitate placement of a 14 G×140 mm catheter (Abbocath-T, Abbott Ireland, Sligo, Rep. of Ireland) which was sutured to the skin using 2-0 nylon suture (Burns Veterinary Supply, Inc. Westbury, N.Y.). Catheter patency was maintained using 3 ml heparin saline flush containing 3 USP units heparin sodium/ml 0.9% saline (Heparin Sodium Injection, USP, Baxter Healthcare, Deerfield, Ill.; Baxter Healthcare Corporation, Deerfield, Ill.). The catheters were removed immediately after the last blood collection.

d. Group Assignment and Lameness Induction

The calves were randomly assigned to receive a single oral (PO) administration of: (1) 0.5 mg/kg lactose monohydrate placebo (PLBO) (n=6); (2) 0.5 mg/kg meloxicam (MEL) (n=6); or (3) 0.5 mg/kg meloxicam combined with 15 mg/kg gabapentin (MEL-GABA) (n=6) at the start of a 9-day acclimatization period (Period 1). Calves were then assigned to one of 3 pens with 2 calves/treatment group/pen. During the acclimatization period, baseline data were collected once daily for 5 days. Blood samples for drug concentration were also collected once daily for 4 days.

After acclimatization, lameness was induced as previously described (Kotschwar et al, 2009). More specifically, chemical synovitis/arthritis was induced with an injection of 20 mg amphotericin B (X-Gen Pharmaceuticals, Inc, Big Flats, N.Y.) into the left hind distal interphalangeal joint of each calf (Period 2). All calves were first restrained in a chute with a head gate as conducted through the acclimatization period, and the hind leg was restrained with ropes at the fetlock and stifle. After restraint, the appropriate hindlimb lateral digit pastern region was prepared with close clipping of hair (No. 40 clipper blade) and aseptic skin preparation using povidone iodine scrub and 70% isopropyl alcohol swabs, followed by injection of the amphotericin B. Amphotericin B is a polyene antibiotic that produces a controlled, mild to moderately severe synovitis/arthritis of short duration. After the sterile needle was inserted, correct placement into the distal interphalangeal joint was verified by aspiration of synovial fluid back into the syringe. Continued position within the distal interphalangeal joint was verified periodically throughout the injection by ease of injection followed by back-flow of synovial fluid and amphotericin B into the syringe. This admixture was then fully injected into the distal interphalangeal joint to complete the procedure.

Rescue analgesic therapy options for unresolved lameness after final data collection included flunixin meglumine at 2.2 mg/kg intravenously (IV) once daily, butorphanol tartrate at 0.05 mg/kg SC once daily, morphine at 0.1 mg/kg SC once daily, and lidocaine 2%, with a total dose of 100 mg intraarticular once.

e. Drug Treatment

At 4 hours after lameness induction, calves received the same assigned treatments administered PO in Period 1 except these were repeated once daily for 4 days. At the time of treatment, changes in gait were evaluated using contact force, contact area, contact pressure, impulse and stride length measured with a pressure mat. At the same time visual lameness scores were recorded on a 5-point scale by a masked observer and blood samples for drug determination were collected. Animal activity was assessed continuously with pedometers. Drug concentrations were determined by HPLC-mass spectrometry.

f. Blood Sample Collection

Twenty milliliters of whole blood for drug concentration in treated calves was collected into syringes using the pre-placed jugular catheter immediately prior to drug or placebo administration, in Period 1, and again at 0 16, 24, 48, 72 and 96 hours thereafter. In Period 2, blood samples were collected at 0, 16, 24, 48, 72, 84, 96, 108, 120, 132, 144 and 168 hours after first administration. Immediately after obtaining the blood sample, 3 ml of heparin saline flush, as described above, was used to maintain patency of the catheter. The vacutainer tubes were stored on ice for no more than 60 minutes pending sample processing. Thereafter, blood samples were centrifuged at 1,600 g for 15 minutes at 0° C. Plasma was pipetted from their respective tubes and placed in cryovials identified with calf ID, date, timepoint sample, and treatment group. The samples were stored at −40° C. prior to sample analysis. All samples were analyzed within 60 days of sample collection.

g. Plasma Gabapentin and Meloxicam Analysis

Plasma concentrations of gabapentin and meloxicam were determined with HPLC (Shimadzu Prominence, Shimadzu Scientific Instruments) and mass spectrometry (API 2000, Applied Biosystems). Plasma samples or standards (100 μL) were added to 100 μL of internal standard (pregabalin 5 μg/mL in methanol) and 400 μL of methanol with 0.1% formic acid to precipitate the proteins. Quantitation was performed by calculating the ratios of gabapentin m/z 172.1→154.1 and meloxicam m/z 352.09→114.90 responses relative to the internal standard m/z 160.00→142.00 transition. The samples were vortexed for 5 seconds and centrifuged for 10 min. at 15,000 g. Supernatant (200 μL) was transferred to an injection vial with an injection volume of 25 μL. The mobile phase consisted of 100% B from 0 to 1 min. with a linear gradient of 50% B at 3 min., which was maintained until 6 min., followed by a linear gradient of 100% B at 6.5 min., with a total run time of 8 min. The solvent 'A' was acetonitrile and the solvent 'B' was 0.1% formic acid at a flow rate of 0.5 mL/min. Separation was achieved with a phenyl column (Hypersil Gold, 150×2.1, 5 μM, Thermo Scientific) maintained at 40° C.

The standard curve was linear from 0.05-10 μg/mL for gabapentin and 0.025-2.5 μg/mL for meloxicam and was accepted if the correlation coefficient exceeded 0.99 and predicted values were within 15% of actual values. The accuracy of the gabapentin assay was 97±10% and the coefficient of variation was 10% determined on replicates of 3 at 0.05, 0.1, 0.5, 5, and 10 μg/mL. The accuracy of the meloxicam assay was 100±9% and the coefficient of variation was 6% determined on replicates of 3 at 0.025, 0.05, 0.25, 1.0, and 2.5 μg/mL. The limits of detection was 0.05 and 0.025 μg/mL for gabapentin and meloxicam, respectively, (defined as the lowest concentration on the standard curve with predicted concentrations within 15% of actual concentrations).

h. Pharmacokinetics Analysis

Pharmacokinetic analyses were performed with computer software (WinNonlin 5.2, Pharsight Corp). The variables calculated included the area under the curve from time 0 to infinity (AUC) using the linear trapezoidal rule, area under the first moment curve from time 0 to infinity (AUMC), plasma clearance per fraction of the dose absorbed (Cl/F), apparent volume of distribution (area method) per fraction of the doze absorbed (Vz/F), first-order rate constant (λz), terminal half-life ($t_{1/2}$), and mean residence time extrapolated to infinity (MRT). The maximum serum concentration (Cmax) and time to maximum serum concentration (Tmax) were determined directly from the data.

i. Pressure Mat Analysis

A commercially available floor mat-based pressure/force measurement system (MatScan, Tekscan, Inc., South Boston, Mass.) was used to record and analyze the affected feet of each calf. The pressure mat was calibrated daily and each time the computer software was engaged using a known mass to ensure accuracy of the measurements at each time point. Videosynchronization was used to ensure consistent gait between and within calves for each time point. Using research grade software (HUGEMAT Research 5.83, Tekscan, Inc., South Boston, Mass.), contact pressure, contact area, and stance phase duration in the affected feet were measured. Surface area was calculated by area only of the loaded or "contact" sensing elements inside the measurement box. Contact pressure was calculated as force on the loaded sensing elements inside the measurement box divided by the contact area.

j. Activity Measurement

Step counts were deternned using electronic pedometers (Sportline Step Count Pedometer, Sportline Inc, Yonkers, N.Y.) attached to the right hind limb. Pedometers were housed in a plastic casing attached to the limb using flexible bandage (Vetrap Bandaging Tape, 3M, St. Paul, Minn.).

k. Clinical Evaluation

The degree of lameness was scored using a 1 to 5 scale adapted from Sprecher (Sprecher et al., 1997) (Table 16). Lameness scores were determined twice daily to document presence of lameness and to visually score severity of lameness. To eliminate inter-observer variation, all lameness scores were assigned by one blinded veterinarian (DEA) with training and expertise in bovine lameness assessment. Intra-observer variability was assessed periodically by randomly selecting calves for repeated assessment to ensure consistency of scoring. All lameness examinations were performed on even, non-sloped concrete floors free of obstructions and debris. Each lameness score was determined by watching the calf walk a minimum of 20 meters in a straight line, turn, and walk 20 meters back to the starting point.

TABLE 16

Sprecher lameness scoring system

| Lameness Score | Clinical Description |
|---|---|
| 1 | Normal-Stands and walks normally, with all feet placed with purpose |
| 2 | Mildly lame-Stands with flat back, but arches when walks, gait is slightly abnormal |
| 3 | Moderately lame-Stands and walks with an arched back, and short strides with one or more legs |
| 4 | Lame-Arched back standing and walking, with one or more limbs favored but at least partially weight bearing |
| 5 | Severely lame-Arched back, refuses to bear weight on one limb, may refuse or have great difficulty moving from lying position |

3. Results

Figure 15:
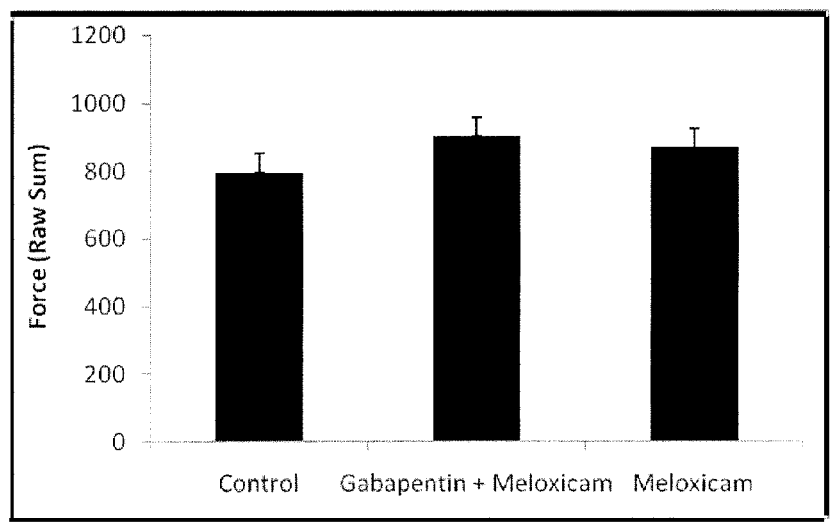
FIG. 15 is a chart of the mean (±SEM) contact force in calves with induced lameness after treatment with a placebo, meloxicam, or meloxicam and gabapentin from Example 6.
Figure 16:
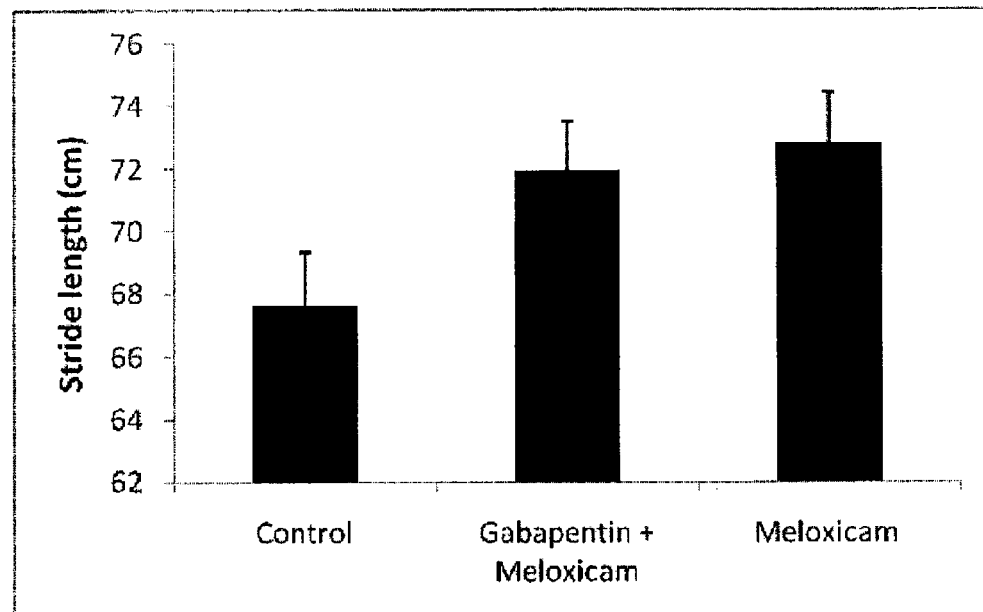
FIG. 16 is a chart of the mean (±SEM) stride length in calves with induced lameness after treatment with a placebo, meloxicam, or meloxicam and gabapentin from Example 6.
Figure 17:
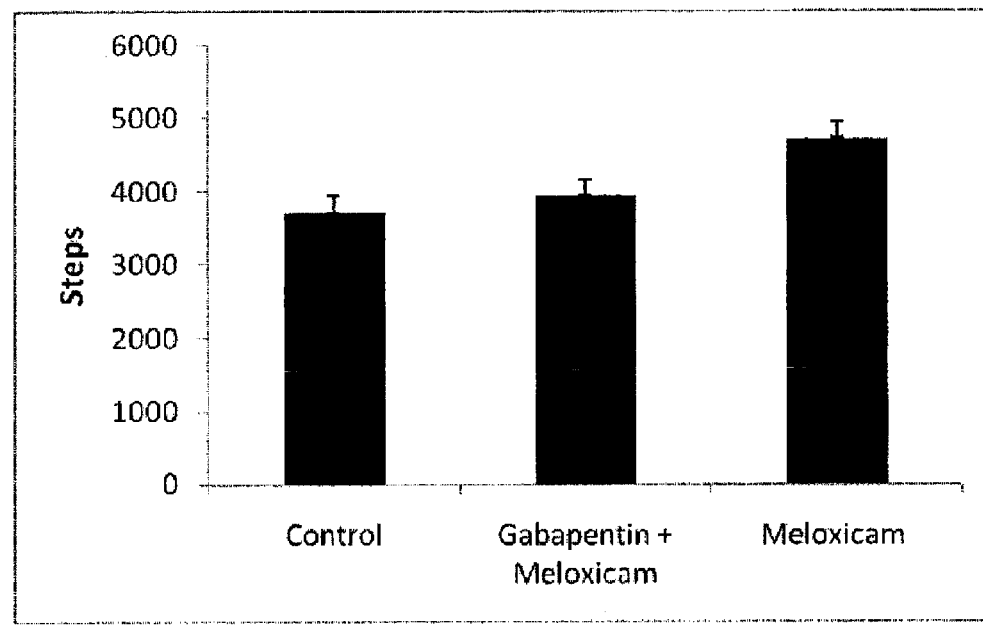
FIG. 17 is a chart of the number of steps taken by calves with induced lameness after treatment with a placebo, meloxicam, or meloxicam and gabapentin from Example 6.

Repeated measures outcomes were compared statistically using a random effects-mixed model and pharmacokinetic (PK) data were analyzed using non-compartmental analysis. In Period 1 the mean (±SD) Cmax, Tmax and $t_{1/2}$ λz were 3.98±0.96 µg/mL, 16 h and 8.57±0.95 h, respectively, for gabapentin, and 2.70±0.35 µg/mL, 18.67±4.13 h and 27.55±6.84 h, respectively for meloxicam. In Period 2, the mean (±SD) Cmax, Caverage and $t_{1/2}$, λz were 3.97±1.49 µg/mL, 2.94±1.22 µg/mL and 9.45±0.63 h, respectively, for gabapentin, and 4.69±1.05 µg/mL, 3.81±0.96 µg/mL and 25.44±6.84 h, respectively, for meloxicam. Mean (±SEM) contact force was less in PLBO calves (795.02±56.37 kg) compared with the MEL-GABA calves (903.88±54.00 kg) (n=0.042) and the MEL calves (869.80±54.96 kg) (p=0.20) (FIG. 15). Mean (±SEM) stride length was shorter in the PLBO calves (67.65±1.67 cm) compared with the MEL-GABA calves (71.96±1.53 cm) (p=0.05) and the MEL calves (72.82±1.59 cm) (p=0.02) (FIG. 16). MEL-treated calves took more steps over the course of the study (4,667.87±166.64 steps) than the MEL-GABA calves (3,939.19±207.50 steps) (p=0.02) and the PLBO calves (3,703.71±233.88 steps) (p=0.007) (FIG. 17). Significantly more PLBO calves had a visual lameness score of 3 and 4 compared to the MEL and MEL+GABA calves (p=0.03). The results of this study suggest that MEL administered alone or in combination with GABA reduced the severity of lameness in calves following induction of lameness with amphotericin B. These findings have important implications for the management of chronic/pathological pain in cattle.

Example 7

Pharmacokinetics of Oral Melonicam in Ruminant and Pre-Ruminant Calves

1. Introduction

The pharmacokinetics of oral meloxicam has not been studied in pre-ruminant calves. Due to differences in diet as well as differences in gastrointestinal, hepatic, and renal function, meloxicam may exhibit a different pharmacokinetic profile in pre-ruminant vs. ruminant calves. The current study was conducted in two parts. Experiment #1 was conducted to directly compare pharmacokinetic differences between ruminant and pre-ruminant calves when meloxicam was delivered into the rumen via gavage at a dose of 0.5 mg/kg body weight. Experiment #2 was conducted to determine the pharmacokinetic profile of oral meloxicam in pre-ruminant calves when the dose was suckled in milk replacer, and thus would likely bypass the rumen. Oral meloxicam was administered at 0.5 mg/kg to six ruminant calves via gavage (RG); to six pre-ruminant calves via gavage (PRG); and to six pre-ruminant calves via suckling in milk-replacer (PRF). Plasma drug concentrations, determined over 120 h post-administration, were analyzed by compartmental and non-compartmental methods. The rate of drug absorption was faster (P<0.01) in PRF (0.237±0.0478 h$^{-1}$) than RG calves (0.0815±0.0188 h$^{-1}$), while absorption PRG calves (0.153±0.128 h$^{-1}$) was not different from other groups. Cmax was lower (P=0.03) in PRF (1.27±0.430 µg/mL) than PRG calves (2.20±0.467 µg/mL), while Cmax of RG calves (1.95±0.955 µg/mL) was not different from other groups. V/F was higher in PRF calves (365±57 mL/kg) than either PRG (177±63 mL/kg, P<0.01) or RG (232±83 mL/kg, P=0.01) calves. The observations were likely due to differences in bioavailability, physiological maturity, and timing of the drug delivery into different compartments of the ruminant gastrointestinal tract. Results suggest that the bioavailability of meloxicam is decreased when administered into the abomasum with milk-replacer.

2. Materials and Methods

This study was approved by the Institutional Animal Care and Use Committee at Kansas State University (KSU).

a. Animals and Housing

Experiment #1: Weaned and non-weaned male Holstein calves were obtained from Kansas dairy herds and acclimated for 4 weeks prior to study initiation. All calves were black and white Holsteins except one pre-ruminant (#31), which was a red and white Holstein. Six weaned calves, 4-7 months old, and weighing 95-168 kg at time of study were classified as full ruminants and were group-housed on an outdoor concrete pad (9.8 m×18.3 m) with a partial roof over straw bedding. Six unweaned calves, 6-8 weeks old and weighing 62-89 kg at time of study were classified as pre-ruminants and were similarly housed nearby in individual contiguous enclosures (1.6 m×5.3 m) constructed with wire panels. Ruminant calves were maintained on water and grass hay ad libitum and supplemented with a typical receiving diet composed of cracked corn, oats, soybean meal, molasses and a protein/vitamin/mineral supplement at 6-8 kg/head/day. Pre-ruminant calves were primarily maintained on a bueketfed milk replacer diet (Maxicare, Land O'Lakes, Minn.) with ad libitum water (in a bucket) and calf starter ration (Herd Maker Supreme B90, Land O'Lakes. Minn.) throughout the acclimation period and the during the study.

Upon arrival, study animals were identified with numeric ear tags, vaccinated (Bovishield Gold, Pfizer Inc., NY, NY), and administered oxytetracycline (Noromycin 300 LA, Norbrook Laboratories, County Down, Northern Ireland) IM, 9 mg/kg body weight. All calves were surgically castrated 1-2 weeks after arrival and allowed to heal for a minimum of 10 days prior to the study.

At study initiation, the mean (±SD) weights of the ruminant and pre-ruminant groups were 129.2±32.3 kg and 75.5±9.3 kg respectively. Weights for dose calculation were determined by weighing the calves 24 hours prior to treatment administration.

Experiment #2: Six Holstein bull calves, 18-28 days of age, with mean (±SD) weight of 46.4±10.5 kg, born at the KSU Dairy Unit, were maintained in their accustomed individual housing units (1.2 m×4 m) comprised of a covered hutch with attached outside exercise area. Diet consisted primarily of bottle-and-nipple-fed milk replacer (Mother's Pride, Ridley Inc, Mankato, Minn.) supplemented by ad libitum water (in a bucket) and starter ration (Super Krunch 22% Calf Starter, Ridley Inc, Mankato, Minn.), with daily consumption recorded as above.

b. Experimental Design

Experiment #1 was a parallel design with rumen development classification as the explanatory variable, and with pharmacokinetic parameters as the response variables. All calves received meloxicam, PO, at a target dose of 0.5 mg/kg.

Approximately 24 hours prior to study commencement, calves were restrained with a head gate and halter for intravenous catheter placement. The area over the jugular vein was clipped and surgically prepared with alternating scrubs of 70% isopropyl alcohol and povidone iodine. The catheter site was infiltrated with 2% lidocaine injection, 1 mL s.c., (Hospira Inc, Lake Forest, Ill.) prior to making a stab incision with a #22 scalpel blade. Using sterile technique, a 14 G×130 mm extended use catheter (MILACATH®, MILA International, Florence, Ky.) with injection plug (SURFLOW®, Terumo, Somerset, N.Y.) was inserted into the right jugular vein and sutured to the skin using #3 nylon suture (BRAUNAMID®, Braun, Bethleham, Pa.). Catheter patency was maintained by flushing with 3 mL of a heparin saline solution containing 3 USP units heparin sodium/mL saline (Heparin Sodium Injection, Baxter Healthcare, Deerfield, Ill.). Neither food nor water was withheld at any time during the study; pre-ruminants were bucket-fed their usual quantity of milk replacer 30 minutes prior to dosing.

Meloxicam was administered orally at 0.5 mg/kg (Meloxicam tablets 15 mg (NDC 60505-2554-1), Apotex Corp, Weston, Fl; Lot # JD9485). The dose was rounded to the nearest whole tablet and was based upon body weight obtained 24 hours prior to study. Tablets were crushed and mixed in 50 mL of tap water within 5 minutes of administration. After passing a stomach tube with the aid of a Frick speculum, one operator blew air into the tube while another listened through a stethoscope placed over the rumen to assure placement within the gastrointestinal (GI) tract. The drug suspension was delivered through the stomach tube and then chased with 300 mL of water. Air was then blown through the tube to empty all fluid contents into the GI tract prior to removal.

Approximately 6 mL of blood was collected through the catheter port at 0 and 30 minutes and at 1, 2, 3, 4, 5, 6, 8, 10, 12, 18, 24, 36, 48, 60, 72, 96 and 120 hours after administration. Prior to blood sampling, calves were temporarily restrained with a rope halter and the catheter cap cleaned with 70% isopropyl alcohol. The heparin lock solution was flushed from the catheter before each collection by twice drawing 5 mL of blood into the syringe and then returning it to the calf through the catheter. Blood drawn into the syringe on the third pull was immediately transferred to a lithium heparin vacutainer tube (BD Diagnostics, Franklin Lakes, N.J.). Samples were stored on ice prior to centrifugation for 10 minutes at 1,500×g within 30 minutes of collection. Plasma was then pipetted into cryovials and frozen at −70° C. until analysis.

Experiment #2: With the exception of the dose delivery method, the second experiment was carried out as described above. The crushed tablets were suspended in the morning ration of rehydrated milk replacer and offered to the calves in nipple bottles as they were accustomed to feeding. Following consumption of the contents, the bottle was rinsed with 100 mL of water and reoffered to the calves. Dose and rinse water were readily consumed by all calves within 5 minutes of feeding initiation.

c. Plasma Drug Analysis

Plasma concentrations of meloxicam (m/z 352.09>114.90) were determined with HPLC (Shimadzu Prominence, Shimadzu Scientific Instruments, Columbia, Md., USA) and mass spectrometry (API 2000, Applied Biosystems, Foster City, Calif., USA). Plasma samples or standards (100 μL) were added to 100 μL of internal standard (piroxicam 0.5 μg/mL in methanol, m/z 332.12→95.10) and 300 μL of methanol with 0.1% formic acid to precipitate the proteins. The samples were vortexed for 5 seconds and centrifuged for 10 minutes at 10,000×g. The supernatant, 200 μL, was transferred to an injection vial with the injection volume set to 10 μL. The mobile phase consisted of A: acetonitrile and B: 0.1% formic acid at a flow rate of 0.4 mL/min. The mobile phase consisted of 85% B from 0-0.5 minutes with a linear gradient to 50% B at 2.5 minutes which was maintained until 3 minutes, followed by a linear gradient to 85% B at 4 minutes with a total run time of 5 minutes. Separation was achieved with a C8 column (Supelco Discovery C8, 50 mm×2.1 mm×5 μm, Sigma-Aldrich, St. Louis, Mo., USA) maintained at 40 C. With a limit of quantification of 0.025 μg/mL, the standard curve was linear from 0.025 μg/mL to 10 μg/mL and was accepted if the correlation coefficient exceeded 0.99 and predicted values were within 15% of the actual values. The accuracy of the assay was 103±7% of the actual value and the coefficient of variation was 7% determined on replicates of 5 each at 0.025, 0.5, and 5 μg/mL.

d. Pharmacokinetic and Statistical Analysis

Noncompartmental (NCA) and compartmental (CA) pharmacokinetic analyses were performed with computer software (WinNonlin 5.2, Pharsight Corporation, Mountain View, Calif., USA). Maximum serum meloxicam concentration (Cmax) and time to maximum serum concentration (Tmax) were obtained directly from the data. The parameters calculated with NCA included the plasma clearance per fraction of dose absorbed (Cl/F); the first order elimination rate constant ($\lambda_z$); and terminal half-life ($t_{1/2}$ $\lambda z$). The observed area under the curve extrapolated to infinity ($AUC_{NF}$) was calculated using the trapezoidal rule to calculate AUC to the last observed concentration ($C_{last}$), then adding the extrapolated portion beyond that point as follows:

$$AUC_{INF} = AUC_{last} + \frac{C_{last}}{\lambda_z}$$

The apparent volume of distribution per fraction of the dose absorbed based on the terminal phase ($V_z/F$) was calculated by the following equation:

$$\frac{V_z}{F} = \frac{Dose}{\lambda_z \times AUC_{INF}}$$

The fit of compartmental models was compared by inspection of residuals, the Akaike Information Criterion, and the Schwarz Bayesian Criterion (Gabrielsson & Weiner, 2009). A one-compartment model with no lag time, with weighting of 1/(predicted-C)$^2$ was determined to best fit the data. The parameters estimated through compartmental modeling of mean data included the absorption rate constant ($K_{01}$): the elimination rate constant ($K_{10}$); and apparent volume of distribution per fraction of the dose absorbed (V/F). The data were fit to the following one-compartment model with no lag time and with weighting of 1/(predicted-C)$^2$:

$$C_t = \left[\frac{DFK_{01}}{V(K_{01} - K_{10})}\right][e^{-K_{10}t} - e^{-K_{01}t}]$$

where $C_t$ is plasma concentration at time, t; and D is administered dose.

Statistical analyses were performed using IMP (SAS Institute Inc, Cary, N.C.); P-values of A.05, were considered statistically significant. The normality assumption was tested for each variable set with the Shapiro-Wilk W test. Group means from the normally distributed variables, AUC, T max, $\lambda_z$, and dose were compared by one-way analysis of variance. When significant differences were detected, pairwise comparisons were performed using the Tukey-Kramer HSD method to protect the experiment-wide level of significance. Means of the non-normally distributed variables, Cl/F, Cmax, $t_{1/2}$,$V_z$/F, $K_{01}$, $K_{10}$ were compared using a Kruskal-Wallis nonparametric one-way analysis of variance. When significant differences were detected between means within the group, pairwise comparisons were performed with the Wilcoxon two-level nonparametric test to determine which pairs were different.

Upon initial inspection of the data, the pharmacokinetics of meloxicam in Calf#31 in the PRG group appeared to be different from the rest of the PRG group. For that reason all statistical analyses were performed both with, and without, Calf #31. Although the PK parameters, Cl/F, $\lambda_z$, AUC$_{INF}$, Cmax, MRT and $t_{1/2}\lambda z$ for Calf #31 were group extremes which biased the mean, the exclusion of that calf's data did not result in a change in the outcome of significance tests, so data were not excluded.

e. Plasma Chemistry Analysis

Experiment #1: Archived plasma obtained from calves at the pre-study timepoint in the first experiment was submitted to the Kansas State University Diagnostic Laboratory for analysis of albumin, globulin, and total protein. Analysis was performed using an automated, software-controlled system (Cobas 6000 analyzer, Roche Diagnostics, Switzerland).

3. Results

Figure 18:
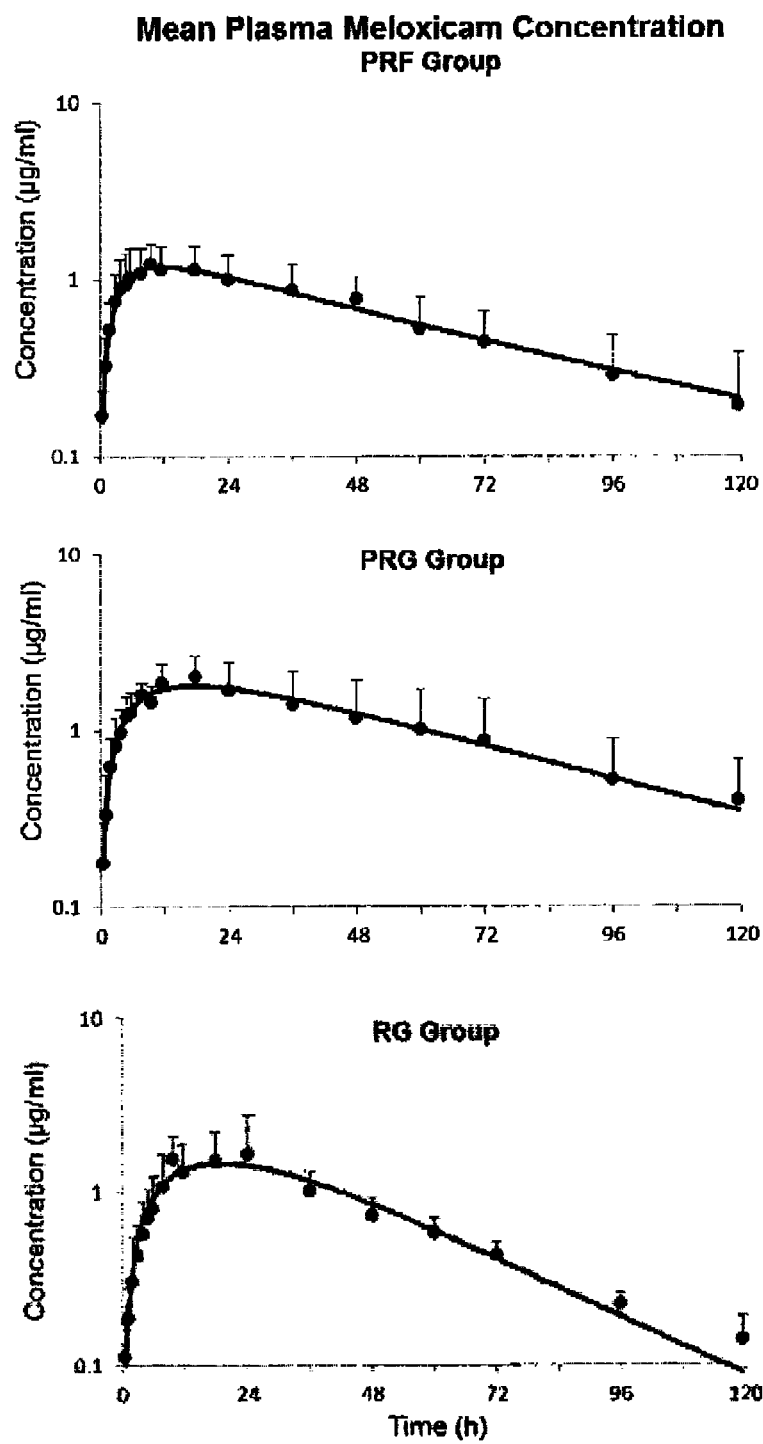
FIG. 18 are graphs of the plasma meloxicam concentration (mean±SD) following single 0.5 mg/kg PO administration to ruminant calves via gavage (RG), pre-ruminant calves via gavage (PRG) and pre-ruminant calves via feeding in milk replacer (PRF). Solid lines represent group mean concentration fit to a one compartment model, with weighting of 1/(predicted y)$^2$.
Figure 19:
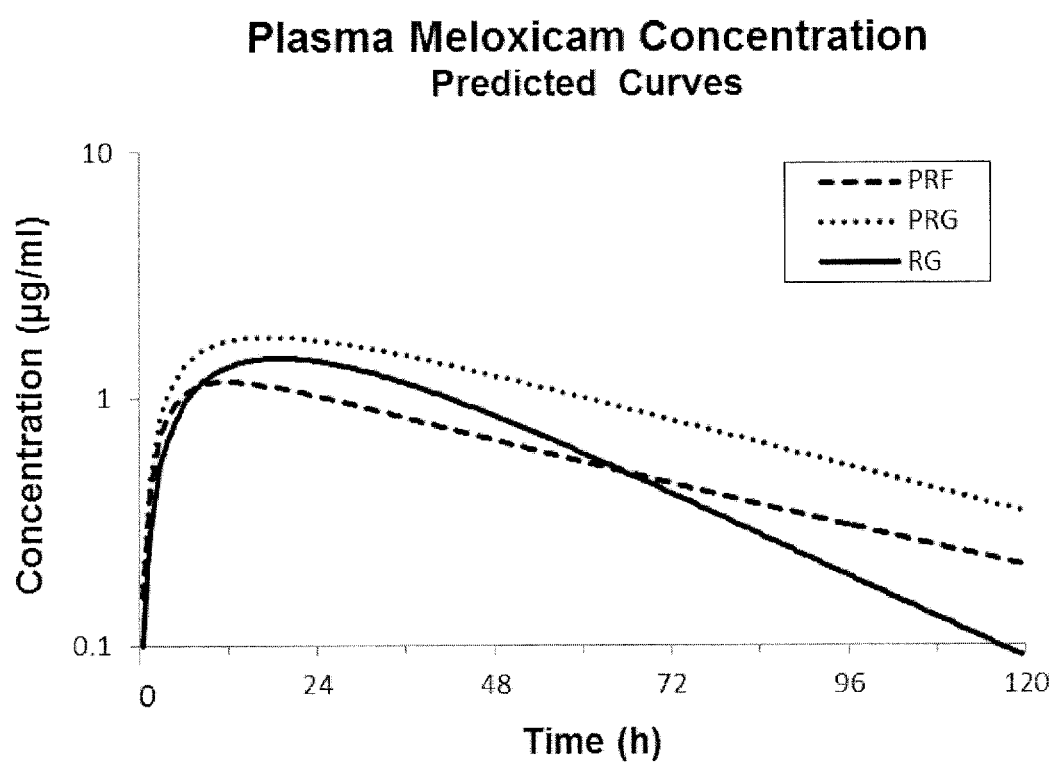
FIG. 19 is a graph of the group mean concentration fit to a one compartment model, with weighting of 1/(predicted y)$^2$ of plasma meloxicam concentration following a single 0.5 mg/kg PO administration to ruminant calves via gavage (RG), pre-ruminant calves via gavage (PRG) and pre-ruminant calves via feeding in milk replacer (PRF).

All calves in the first experiment were determined to have normal levels of plasma proteins. There was not a significant difference between the dose (mean±SD; range) of meloxicam administered to calves within the groups: PRF (0.530≅0.131, 0.350-0.650 mg/kg), PFG (0.509±0.007; 0.497-0.518 mg/kg), and RG (0.515±0.018; 0.5-0.545 mg/kg). There were quantifiable levels of meloxicam in the plasma of all calves at the first timepoint, 30 minutes after dosing. The model-predicted time-concentration curve with observed mean (±SD) concentration for each group is shown in FIG. 18. The figure highlights the greater variation in plasma concentration observed among the PRG calves than in the other groups. In Calf #31, of the PRG group, the plasma concentration of meloxicam was below the limit of quantification by 96 h. For comparison, the predicted curves are overlayed without SD bars in FIG. 19. Summary estimates of pharmacokinetic parameters obtained through NCA are presented in Table 17.

TABLE 17

Pharmacokinetic parameters obtained from non-compartmental analysis of meloxicam after single 0.5 mg/kg PO administration in pre-ruminant calves dosed via ingested milk (PRF) or via gavage (PRG) and ruminant calves via gavage (RG).

| Parameter | Group | Mean | SD | Minimum | Median | Maximum |
|---|---|---|---|---|---|---|
| AUC$_{INF}$ | PRF | 85.4 | 46.6 | 49.6 | 69.7 | 179.0 |
| (h * µg/mL) | PRG | 151.0 | 80.2 | 39.6† | 193.0 | 218.0 |
|  | RG | 86.7 | 28.9 | 54.2 | 83.0 | 137.0 |
| Cl/F | PRF | 6.92 | 2.10 | 3.66 | 7.26 | 9.74 |
| (mL/h/kg) | PRG | 5.28 | 4.52 | 2.34 | 2.63 | 13.10† |
|  | RG | 6.45 | 1.92 | 3.80 | 6.45 | 9.28 |
| C$_{max}$ | PRF | 1.27$^a$ | 0.430 | 0.726 | 1.29 | 1.79 |
| (µg/mL) | PRG | 2.20$^b$ | 0.467 | 1.630† | 2.37 | 2.65 |
|  | RG | 1.95$^{ab}$ | 0.955 | 1.020 | 1.85 | 3.74 |
| $\lambda z$ | PRF | 0.0206 | 0.0051 | 0.0118 | 0.0209 | 0.0254 |
| (h$^{-1}$) | PRG | 0.0256 | 0.0229 | 0.0106 | 0.0169 | 0.0713† |
|  | RG | 0.0238 | 0.0045 | 0.0188 | 0.0238 | 0.0304 |
| MRT | PRF | 58.4 | 17.5 | 42.4 | 52.9 | 91.4 |
| (h) | PRG | 63.5 | 29.4 | 20.5† | 70.5 | 98.8 |
|  | RG | 50.3 | 8.3 | 41.1 | 49.5 | 59.8 |
| t½ $\lambda z$ | PRF | 36.0 | 11.7 | 27.3 | 33.3 | 58.5 |
| (h) | PRG | 40.0 | 19.8 | 9.7† | 41.2 | 65.3 |
|  | RG | 29.9 | 5.6 | 22.8 | 29.1 | 37.0 |
| T$_{max}$ | PRF | 14.3 | 6.7 | 6.0 | 14.0 | 24.0 |
| (h) | PRG | 17.0 | 7.0 | 6.0 | 18.0 | 24.0 |
|  | RG | 17.3 | 6.3 | 10.0 | 18.0 | 24.0 |

TABLE 17-continued

Pharmacokinetic parameters obtained from non-compartmental analysis of meloxicam after single 0.5 mg/kg PO administration in pre-ruminant calves dosed via ingested milk (PRF) or via gavage (PRG) and ruminant calves via gavage (RG).

| Parameter | Group | Mean | SD | Minimum | Median | Maximum |
|---|---|---|---|---|---|---|
| Vz/F | PRF | 337▲ | 78 | 289 | 313 | 495 |
| (mL/kg) | PRG | 211● | 75 | 140 | 185 | 340 |
|  | RG | 281●▲ | 103 | 156 | 304 | 407 |

Within a column superscripts not containing the same letter denote a significant difference between associated parameter means ($p < 0.05$). Similarly, symbols denote a nearly significant difference ($p = 0.055$).
†Pharmacokinetic values for Calf #31 in the PRG group which are extremes.

The only significant difference revealed by NCA occurred between the two pre-ruminant groups. Cmax was lower (p=0.03) in PRF (1.27±0.430 µg/mL) than PRG calves (2.20±0.467 µg/mL), while Cmax of RG calves (1.95±0.955 µg/mL) was not different from other groups. There was a difference (p=0.055) in Vz/F of the PRF calves (337±78 mL/kg) and the PRG calves (211±75 mL/kg). Noncompartmental pharmacokinetic parameters associated with Calf #31 in the PRG group represented the group minima for $AUC_{INF}$, Cmax, MRT and $t1/2\lambda z$ and the group maxima for Cl/F and $\lambda z$.

Summary estimates of the pharmacokinetic parameters obtained by fitting the data to a one-compartment model are presented in Table 18.

TABLE 18

Pharmacokinetic parameters obtained from fitting a one-compartmental model, with no lag time, and with weighting of $1/(\text{predicted Y})^2$ to data obtained from administering oral meloxicam, 0.5 mg/kg, to pre-ruminant calves dosed via ingested milk (PRF) or via gavage (PRG) and ruminant calves via gavage (RG).

| Parameter | Group | Mean | SD | Minimum | Median | Maximum |
|---|---|---|---|---|---|---|
| AUC | PRF | 87.0 | 46.2 | 49.0 | 74.2 | 178 |
| (h * µg/mL) | PRG | 149.0 | 79.0 | 38.8† | 186.0 | 220 |
|  | RG | 86.2 | 26.4 | 53.6 | 85.4 | 129 |
| Cl/F | PRF | 6.80 | 2.16 | 3.65 | 7.29 | 9.74 |
| (mL/h/kg) | PRG | 5.34 | 4.56 | 2.31 | 2.74 | 13.40† |
|  | RG | 6.44 | 1.89 | 4.01 | 6.30 | 9.37 |
| $K_{01}$ | PRF | $0.2370^a$ | 0.0478 | 0.1770 | 0.2370 | 0.294 |
| ($h^{-1}$) | PRG | $0.1530^{ab}$ | 0.1280 | 0.0449 | 0.0898 | 0.341 |
|  | RG | $0.0815^b$ | 0.0188 | 0.0525 | 0.0792 | 0.104 |
| $K_{10}$ | PRF | 0.0188 | 0.0059 | 0.0112 | 0.0211 | 0.0253 |
| ($h^{-1}$) | PRG | 0.0310 | 0.0275 | 0.0119 | 0.0219 | 0.0858† |
|  | RG | 0.0289 | 0.0064 | 0.0213 | 0.0285 | 0.0373 |
| V/F | PRF | $365^a$ | 57 | 295 | 353 | 438 |
| (mL/kg) | PRG | $177^b$ | 63 | 106 | 174 | 283 |
|  | RG | $232^b$ | 83 | 130 | 235 | 322 |

Within a column, superscripts not containing the same letter denote a significant difference between associated parameter means ($p < 0.05$).
†Pharmacokinetic values for Calf #31 in the PRG group which are extremes.

Estimates of V/F were significantly different between the PRF group (365±57 mL/kg) and both the PRG (177±63 mL/kg, p<0.01) and the RG (232±83 mL/kg, p=0.01) groups. Whereas compartmental modeling revealed a significant difference (p<0.01) between the rate of absorption in the PRF (0.237±0.0478 $h^-$) and RG (0.0815±0.0188 $h^{-1}$) groups, there was no difference between the $K_{01}$ estimates for either of those groups and that of the PRG group (0.153±0.128 $h^{-1}$). Compartmental pharmacokinetic parameters associated with Calf #31 in the PRG group represented the group maxima for Cl/F and $K_0$ and the minimum for $AUC_{INF}$.

4. Discussion

Between the two experiments described in this study, we examined the pharmacokinetics of meloxicam in 1) ruminant calves dosed orally via gavage, 2) pre-ruminant calves dosed orally via gavage, and 3) pre-ruminant calves dosed orally by mixing the drug in the usual ration of milk replacer. The pharmacokinetic parameters of oral meloxicam in the ruminant calves in the current study were similar to those reported in Example 1.

In the first experiment, no significant difference was found between the PK parameters of ruminant and pre-ruminant calves when meloxicam was mixed with water and delivered via gavage into the rumen. In the second experiment, when the dose was delivered to pre-ruminant calves through suckling a suspension of drug in milk replacer, and thus directly entering the abomasum, Cmax was lower and V/F was higher than in the gavaged pre-ruminants. In comparison with the gavaged ruminant calves, the PRF group estimate of V/F was higher and $K_{01}$ was faster. These differences between the suckled group and the gavaged groups were likely due largely to differences in bioavailability created by the delivery of drug into different stomach compartments and by a probable food-drug interaction with milk-replacer in the PRF calves. Other possible contributing factors include differences in age and physiology.

Upon analyzing the results of the first experiment in this study, there were no significant differences apparent between the PRG and RG groups. It was noted, however, that the $t_{1/2}$ of meloxicam was much shorter in Calf #31 (9.73 h) in the PRG group than the group mean (40 h). Since meloxicam is highly bound to plasma albumin, and thus its availability for renal excretion is limited, it was initially considered that the relatively short elimination half-life of meloxicam in Calf #31 might be due to low levels of albumin in the bloodstream. Analysis of plasma taken immediately prior to dosing, however, revealed no evidence of hypoalbuminemia.

It was also considered that the shorter drug half-life in that particular calf may have been due to the calf reflexively closing the reticular groove during dosing and causing the drug to bypass the rumen. To test this hypothesis, the second experiment was conducted to evaluate the pharmacokinetics of meloxicam in calves when the dose was delivered in a manner likely to be delivered directly to the abomasum. The minimum $t_{1/2}$ value observed in the PRF group however, was 27.3 h, which was similar to the minimum observed in the RG group of 22.8 h, so it was considered unlikely that the short $t_{1/2}$ observed in Calf #31 was due to the drug simply bypassing the rumen. The reason for the shorter $t_{1/2}$ in that calf was not definitively determined, though a possible explanation could be increased metabolic enzyme activity in that individual. This supposition is supported by Calf #31 exhibiting the group minimum Cmax, the group maximum Cl/F, yet the Vz/F was not an extreme value.

Of note, Calf #31 was the only Holstein of red color in the study. The red color in the Holstein breed is a recessive trait, with black being the dominant color. Thus a red Holstein carries two copies of the gene for red color, whereas a black Holstein may carry two copies of the gene for black color, or may carry one for each color (Specht, 2009). It is not known if there was a genetic association between the coat color of Calf #31 and what appeared to be an increased rate of drug metabolism. It would be of interest to perform an IV/PO crossover pharmacokinetic study with meloxicam and equal numbers of red and black Holstein calves to discern if a difference exists between the two color stains. As shown in Table 19, the pharmacokinetics of meloxicam in black Holstein calves in an IV/PO randomized crossover study (Example 1) were of similar range to those in the current study.

TABLE 19

Selected pharmacokinetic parameters from Examples 1 and 7.

| Example | Parameter (Units) | Dose (mg/kg) | Route | Mean | SD | Minimum | Median | Maximum |
|---|---|---|---|---|---|---|---|---|
| 1 | Cl (mL/h/kg) | 0.5 | IV | 6.1 | 0.4 | 4.8 | 6.0 | 7.2 |
| 1 | Cl/F (mL/h/kg) | 1.0 | PO | 6.4 | 0.6 | 3.6 | 6.6 | 7.8 |
| 5 | Cl/F (mL/h/kg) | 0.5 | PO | 6.0 | 1.2 | 4.2 | 6.0 | 7.1 |
| 1 | t½ λz (h) | 0.5 | IV | 20.4 | 0.7 | 17.8 | 20.6 | 22.8 |
| 1 | t½ λz (h) | 1.0 | PO | 28.6 | 3.6 | 20 | 26.3 | 43.3 |
| 5 | t½ λz (h) | 0.5 | PO | 20.5 | 9.2 | 8.4 | 17.6 | 33.2 |
| 1 | Vz (ml/kg) | 0.5 | IV | 102 | 6 | 80 | 100 | 120 |
| 1 | Vz/F (ml/kg) | 1.0 | PO | 246 | 20 | 202 | 234 | 321 |
| 5 | Vz/F (ml/kg) | 0.5 | PO | 160 | 40 | 87 | 156 | 218 |

When meloxicam was given orally to 6 beef calves of mixed breed origins, the ranges for Cl/F, Vz/F, and $t_{1/2}$ λz were similar to those seen with black Holstein calves, with the exception of a minimum $t_{1/2}$λz value of 8.4 h which is similar to that of the red Holstein (Calf #31, 9.7 h) in the current study. Therefore, Calf #31, while initially appearing to be a possible outlier, likely represents a population of calves with increased metabolism in a skewed distribution.

PK data from the PRF group was statistically compared to that of the PRG and RG groups, although they were conducted in trials approximately one month apart in separate facilities. And although the PRF and PRO groups both had immature rumen development and were consuming regular feedings of milk replacer, the PRF calves were 18 to 28 days of age whereas the PRG calves were 6-8 weeks of age. Furthermore, the milk replacer fed to the pre-ruminant groups was of two different brands.

There was greater variability in pharmacokinetic parameter estimates between individuals within each of the pre-ruminant groups than between individuals within the ruminant group. This increased variability within the pre-ruminant groups may have been due to a combination of factors such as amount of starter ration and/or milk replacer consumed on the day of dosing, the presence of undiagnosed enteric pathology, differences in maturation of the hepatic metabolic enzyme system, differences in rumen maturity, and closure kinetics of the reticular groove while consuming the dose in milk replacer. (De Backer & Debackere, 1979; Marriner, 1979; Nouws, 1992).

We claim:

1. A method of improving the performance of a ruminant or pre-ruminant animal following processing, comprising:
   orally administering to said animal an effective amount of meloxicam or a pharmaceutically acceptable salt thereof; and subjecting said animal to processing, wherein said animal has improved performance after said processing wherein said processing is selected from the group consisting of dehorning, castration, branding, and combinations thereof.

2. The method of claim 1, wherein said animal is a bovine.

3. The method of claim 1, wherein said meloxicam or pharmaceutically acceptable salt thereof is administered to said animal in an amount sufficient to provide a level of meloxicam of from about 0.1 mg/kg body weight to about 5 mg/kg body weight of said animal.

4. The method of claim 1, wherein said meloxicam or pharmaceutically acceptable salt thereof is in the form of a tablet, capsule, liquid, granule, top-dress, suspension, bolus, drench, or solution.

5. The method of claim 1, wherein said meloxicam is administered to said animal up to about 72 hours before said processing.

6. The method of claim 1, wherein said improved performance is selected from the group consisting of increased weight gain, decreased incidence of respiratory illness, and increased activity.

7. The method of claim 1, wherein said ruminant or pre-ruminant animal has horns or horn buds, said processing comprising:
   dehorning said animal, wherein said animal has increased weight gain after said dehorning.

8. The method of claim 7, wherein said dehorning is selected from the group consisting hot iron, knife, scoop, spoon, cup, and tube dehorning.

9. The method of claim 7, wherein said animal is a bovine, and said animal has an average daily weight gain of at least about 0.75 kg/day, as calculated over a 10-day period after said dehorning.

10. The method of claim 1, wherein said animal is subjected to processing without the use of a local anesthetic.

11. The method of claim 10, wherein said local anesthetic is selected from the group consisting of a cornual nerve block, lidocaine, Procaine, and sedative analgesia.

12. The method of claim 1, comprising administering said meloxicam or pharmaceutically acceptable salt thereof to said animal without any other adjunctive therapy.

13. The method of claim 12, wherein said adjunctive therapy is selected from the group consisting of an antibiotic, hormonal implant, ionophore, growth promotants, and vaccine.

14. A method of administering meloxicam or a pharmaceutically acceptable salt thereof for respiratory illness in a ruminant or pre-ruminant male animal following castration, comprising:
    administering to said animal an effective amount of meloxicam or a pharmaceutically acceptable salt thereof; and
    castrating said animal, wherein said animal remains free of a respiratory illness.

15. The method of claim 14, wherein said animal remains free of respiratory illness for at least about 28 days after said castrating.

16. The method of claim 14, wherein said animal does not have a respiratory illness prior to said administering.

17. The method of claim 14, wherein said meloxicam or pharmaceutically acceptable salt thereof is administered to said animal in an amount sufficient to provide a level of meloxicam of from about 0.1 mg/kg body weight to about 5 mg/kg body weight of said animal.

18. The method of claim 14, wherein said meloxicam or pharmaceutically acceptable salt thereof is orally administered to said animal.

19. A method of treating pathological pain in a ruminant or pre-ruminant animal, comprising orally administering an effective amount of a compound selected from the group consisting of meloxicam or the pharmaceutically acceptable salts thereof, gabapentin or the pharmaceutically acceptable salts thereof, and combinations thereof, to a ruminant or pre-ruminant animal having pathological pain, wherein said pathological pain is leg lameness.

20. The method of claim 19, further comprising co-administering said meloxicam and said gabapentin to said animal.

21. The method of claim 19, wherein said animal has a first clinical lameness score based upon the Sprecher lameness scoring system prior to said administering, said animal having a second clinical lameness score after said administering, wherein said second lameness score is decreased as compared to said first lameness score.

22. The method of claim 19, wherein said animal has a first stride length prior to said administering and a second stride length after said administering, said second stride length being greater than said first stride length.

23. The method of claim 19, said animal placing a first amount of force of said lame leg prior to said administering, wherein after said administering said animal places a second amount of force on said lame leg, said second amount of force being greater than said first amount of force.

24. The method of claim 19, comprising administering said compound to said animal without any other adjunctive therapy.

* * * * *